(12) United States Patent
Oka et al.

(10) Patent No.: US 11,890,318 B2
(45) Date of Patent: Feb. 6, 2024

(54) METHODS AND COMPOSITIONS FOR MODULATING APPETITE AND INTAKE OF SODIUM

(71) Applicant: California Institute of Technology, Pasadena, CA (US)

(72) Inventors: Yuki Oka, Pasadena, CA (US); Sangjun Lee, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 753 days.

(21) Appl. No.: 16/738,380

(22) Filed: Jan. 9, 2020

(65) Prior Publication Data
US 2020/0222500 A1 Jul. 16, 2020

Related U.S. Application Data

(60) Provisional application No. 62/792,257, filed on Jan. 14, 2019.

(51) Int. Cl.
*A61K 38/17* (2006.01)
*C12N 15/86* (2006.01)
*A61K 9/00* (2006.01)

(52) U.S. Cl.
CPC ........ *A61K 38/1709* (2013.01); *A61K 9/0019* (2013.01); *C12N 15/86* (2013.01); *C12N 2750/14143* (2013.01)

(58) Field of Classification Search
CPC .......... C12N 15/86; C12N 2750/14143; A61K 9/0019; A61K 38/1709
See application file for complete search history.

(56) References Cited

U.S. PATENT DOCUMENTS

| | | |
|---|---|---|
| 2012/0232133 A1 | 9/2012 | Balazs et al. |
| 2015/0296756 A1 | 10/2015 | Kohtz |
| 2016/0000126 A1 | 1/2016 | Oka et al. |

OTHER PUBLICATIONS

Thesis by Eleanor Clotilde Sandhu, Institute of Clinical Sciences, Imperial College London, issue date Oct. 2016.*
Lee et al. (Nature, 2019 vol. 568: 93-97).*
Huang et al. (J Comp Neurol. 2021 vol. 529: 657-693).*
Gasparini et al. (Am J Physiol Regul Integr Comp Physiol. 2021 vol. 320: R342-R361).*
Wright et al. (Semin Dial. 2010, vol. 23:415-421).*
Geerling et al., "Genetic identity of thermosensory relay neurons in the lateral parabrachial nucleus," American Journal of Physiology-Regulatory, Integrative and Comparative Physiology 2015, 310, R41-R54.
International Search Report and Written Opinion dated May 7, 2020 in PCT Application PCT/US2020/012869.
Allen et al., "Thirst-associated preoptic neurons encode an aversive motivational drive," Science 2017, 357(6356), 1149-1155.

(Continued)

*Primary Examiner* — Terra C Gibbs
(74) *Attorney, Agent, or Firm* — Sheppard, Mullin, Richter & Hampton LLP

(57) ABSTRACT

Disclosed herein include methods and compositions for modulating sodium appetite and/or intake. In some embodiments, the sodium appetite of a subject is reduced. Also disclosed include methods for identifying modulators for sodium appetite and/or intake.

6 Claims, 37 Drawing Sheets
(35 of 37 Drawing Sheet(s) Filed in Color)

(56) References Cited

OTHER PUBLICATIONS

Anderman et al., "Towards a Wiring-Diagram Understanding of Appetite Control," Neuron 2017, 95(4), 757-778.
Augustine et al., "Hierarchical neural architecture underlying thirst regulation," Nature 2018, 555(7695), 204-209.
Augustine et al., "Peripheral and central nutrient sensing underlying appetite regulation," Trends Neurosci. 2018, 41(8), 526-539.
Berndt et al., "Structural foundations of optogenetics: Determinants of channelrhodopsin ion selectivity," PNAS 2016, 113(4), 822-829.
Betley et al., "Neurons for hunger and thirst transmit a negative-valence teaching signal," Nature 2015, 521(7551), 180-185.
Beutler et al., "Dynamics of gut-brain communication underlying hunger," Neuron. 2017, 96(2), 461-475.
Callaway et al., "Monosynaptic Circuit Tracing with Glycoprotein-Deleted Rabies Viruses," The Journal of Neuroscience 2015, 35(24), 8979-8985.
Carrell et al., "A Novel Procedure for the Synthesis of Libraries Containing Small Organic Molecules," Angew. Chem. Int. Ed. Engl. 1994, 33(20), 2059-2061.
Chandrashekar et al., "The cells and peripheral representation of sodium taste in mice," Nature 2010, 464(7286), 297-301.
Chen et al., "Sensory detection of food rapidly modulates arcuate feeding circuits," Cell 2015, 160(5), 829-841.
Cho et al., "An Unnatural Biopolymer," Science 1993, 261(5126), 1303-1305.
Denton et al., "The Selective Appetite for Na+ Shown by Na+-Deficient Sheep," J. Physiol. 1961, 157, 97-116.
Dewitt et al., "'Diversomers': An Approach to nonpeptide, nonligomeric chemical diversity," Proc. Natl. Acad. Sci. USA 1993, 90, 6909-6913.
Dicara et al., "Role of gustation in sodium appetite," Physiological Psychology 1974, 2(1), 43-44.
Erb et al., "Recursive deconvolution of combinatorial chemical libraries," Proc. Natl. Acad. Sci. USA 1994, 91(24), 11422-11426.
Faraco et al., "Dietary salt promotes neurovascular and cognitive dysfunction through a gut-initiated TH17 response," Nat Neurosci. 2018, 21(2), 240-249.
Gallop et al., "Applications of Combinatorial Technologies to Drug Discovery. 1. Background and Peptide Combinatorial Libraries," Journal of Medicinal Chemistry 1994, 37(9), 1233-1251.
Geerling et al., "Aldosterone-sensitive neurons in the nucleus of the solitary tract: bidirectional connections with the central nucleus of the amygdala," The Journal of Comparative Neurology 2006, 497(4), 646-657.
Geerling et al., "Central regulation of sodium appetite," Exp Physiol 2008, 93(2), 177-209.
Geerling et al., "FoxP2 expression defines dorsolateral pontine neurons activated by sodium deprivation," Brain Res. 2011, 1375, 19-27.
Geerling et al., "Sodium Deprivation and Salt Intake Activate Separate Neuronal Subpopulations in the Nucleus of the Solitary Tract and the Parabrachial Complex," The Journal of Comparative Neurology 2007, 504, 379-403.
Heck et al., "Salt Taste Transduction Occurs through an Amiloride-Sensitive Sodium Transport Pathway," Science 1984, 223(4634), 403-405.
Houghten et al., "Generation and use of synthetic peptide combinatorial libraries for basic research and drug discovery," Nature 1991, 354, 84-86.
Hull et al., "Principles of behavior: an introduction to behavior theory," Appleton-Century, Oxford 1943.
Hurley et al., "The biopsychology of salt hunger and sodium deficiency," Pflugers Arch. 2015, 467(3), 445-456.
Jarvie et al., "HSD2 neurons in the hindbrain drive sodium appetite," Nature Neuroscience 2017, 20(2), 167-169.
Johnson et al., "The Neuroendocrinology of Thirst and Salt Appetite: Visceral Sensory Signals and Mechanisms of Central Integration," Frontiers in Neuroendocrinology 1997, 18, 292-353.

Lam et al., "A new type of synthetic peptide library for identifying ligand-binding activity," Nature 1991, 354(7), 82-84.
Lee et al., "Chemosensory modulation of neural circuits for sodium appetite," Nature 2019, 568, 93-97. https://doi.org/10.1038/s41586-019-1053-2.
Leib et al., "The forebrain thirst circuit drives drinking through negative reinforcement," Neuron 2017, 96(6), 1272-1281.
Lerner et al., "Intact-Brain Analyses Reveal Distinct Information Carried by SNc Dopamine Subcircuits," Cell 2015, 162(3), 635-647.
Lin, "A User's Guide to Channelrhodopsin Variants: Features, Limitations and Future Developments," Exp Physiol. 2011, 96(1), 19-25.
Matsuda et al., "Distinct neural mechanisms for the control of thirst and salt appetite in the subfornical organ," Nature Neuroscience 2017, 20(2), 230-241.
Milan et al., "Salt intake and hypertension therapy," Journal of nephrology 2002, 15(1), 1-6.
Nachman et al., "Roles of Taste and Postingestional Factors in the Satiation of Sodium Appetite in Rats," Journal of Comparative and Physiological Psychology 1966, 62(2), 280-283.
Oka et al., "High salt recruits aversive taste pathways," Nature 2013, 494(7438), 472-475.
Oka et al., "Thirst driving and suppressing signals encoded by distinct neural populations in the brain," Nature 2015, 520(7547), 349-352.
Paxinos et al., "The mouse brain in stereotaxic coordinates," Second Edition, Academic Press 2001.
Peng et al., "Sweet and bitter taste in the brain of awake behaving animals," Nature 2015, 527(7579), 512-515.
Petreanu et al., "Channelrhodopsin-2-assisted circuit mapping of long-range callosal projections," Nature Neuroscience 2007, 10(5), 663-668.
Resch et al., "Aldosterone-Sensing Neurons in the NTS Exhibit State-Dependent Pacemaker Activity and Drive Sodium Appetite via Synergy with Angiotensin II Signaling," Neuron 2017, 96, 190-206.
Richter, "Increased salt appetite in adrenalectomized rats," American Journal of Physiology 1936, 115, 155-161.
Roth, "DREADDs for Neuroscientists," Neuron 2016, 89(4), 683-694.
Rowland et al., "Sodium Appetite: Species and Strain Differences and Role of Renin-Angiotensin-Aldosterone System," Appetite 1988, 11, 143-178.
Sadio et al., "A Mouse Intra-Intestinal Infusion Model and its Application to the Study of Nanoparticle Distribution," Front. Physiol. 2016, 7(579), in 7 pages.
Sakai et al., "Salt appetite is suppressed by interference with angiotensin II and aldosterone," The American Physiological Society 1986, 251, R762-R768.
Smith et al., "Salt Appetite, and the Influence of Opioids," Neurochem Res 2018, 43, 12-18.
Songyang et al., "SH2 Domains Recognize Specific Phosphopeptide Sequences," Cell 1993, 72, 767-778.
Stein et al., "Area Postrema Projects to FoxP2 neurons of the Pre-Locus Coeruleus and Parabrachial Nuclei: Brainstem Sites Implicated in Sodium Appetite Regulation," Brain Res. 2010, 1359, 116-127.
Sternson et al., "Three Pillars for the Neural Control of Appetite," Annu. Rev. Physiol. 2017, 79, 401-423.
Stuber et al., "Lateral Hypothalamic Circuits for Feeding and Reward," Nat Neurosci. 2016, 19(2), 198-205.
Su et al., "Nutritive, Post-ingestive Signals Are the Primary Regulators of AgRP Neuron Activity," Cell Reports 2017, 21, 2724-2736.
Tye et al., "Neural Circuit Motifs in Valence Processing," Neuron 2018, 100(2), 436-452.
Ueno et al., "Mouse intragastric infusion (iG) model," Nat Protoc. 2012, 7(4), 771-781.
Wolf et al., "Multiple Factors in the Satiation of Salt Appetite," Behavioral Neuroscience 1984, 98(4), 661-673.
Wright et al., "Gene therapy for the eye," British Journal of Ophthalmology 1997, 81, 620-623.

(56) References Cited

OTHER PUBLICATIONS

Zardetto-Smith et al., "Role of the central nucleus of the amygdala and bed nucleus of the stria terminalis in experimentally-induced salt appetite," Brain Research 1994, 645, 123-134.

Zimmerman et al., "Thirst neurons anticipate the homeostatic consequences of eating and drinking," Nature 2016, 537(7622), 680-684.

Zuckerman et al., "Discovery of Nanomolar Ligands for 7-Transmembrane G-Protein-Coupled Receptors from a Diverse N-(Substituted)glycine Peptoid Library," J Med Chem. 1994, 37(17), 2678-2685.

* cited by examiner

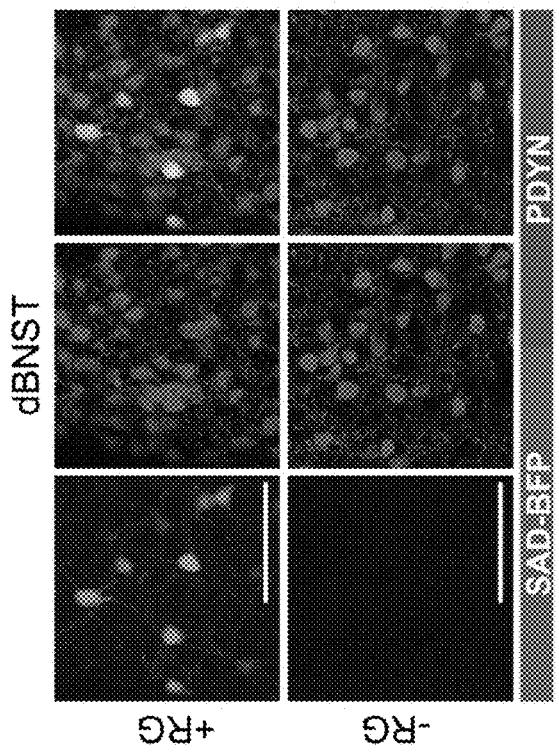
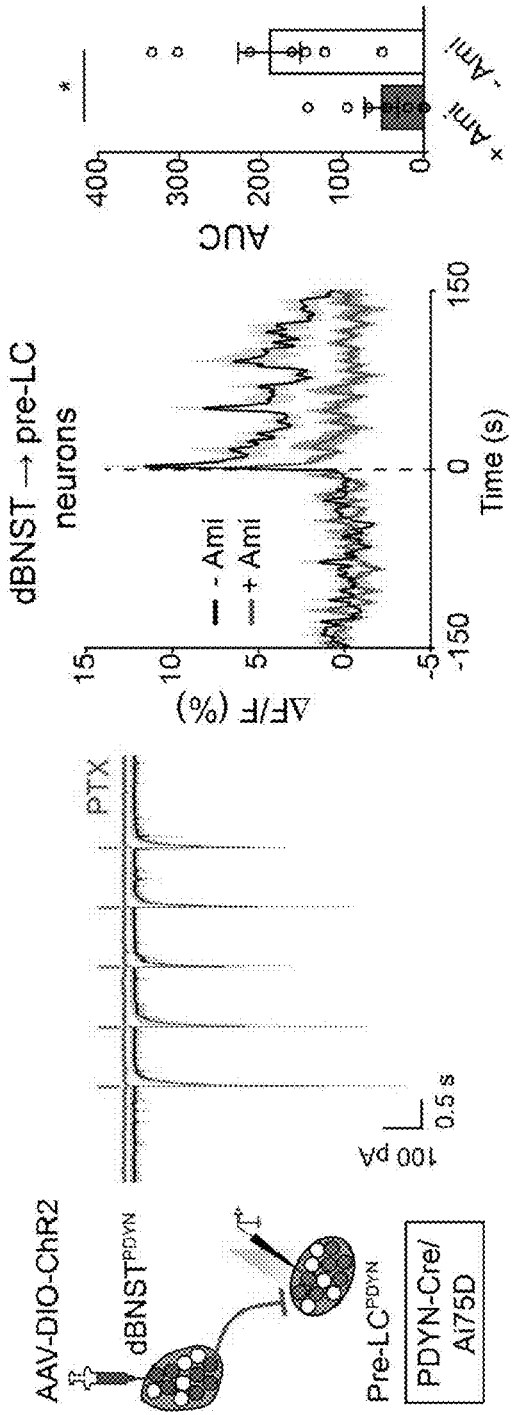
FIG. 5D
FIG. 5E
FIG. 5F

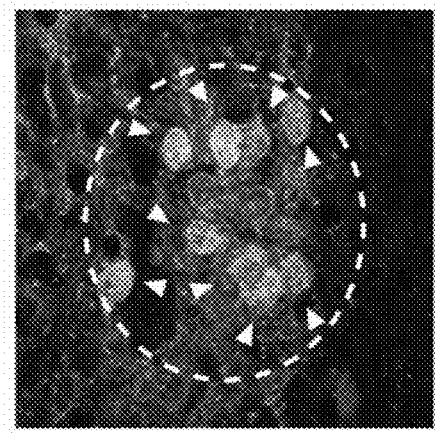
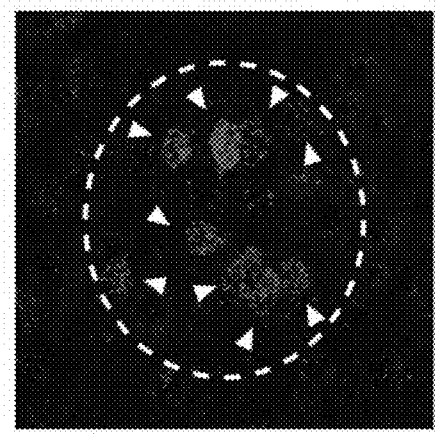
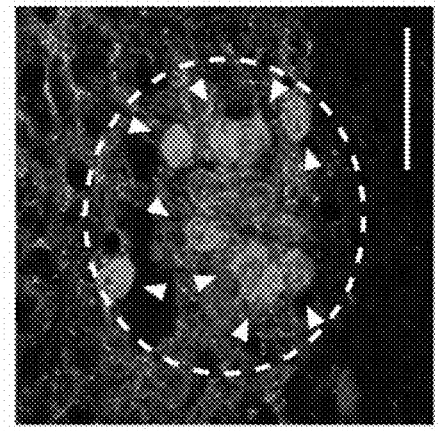
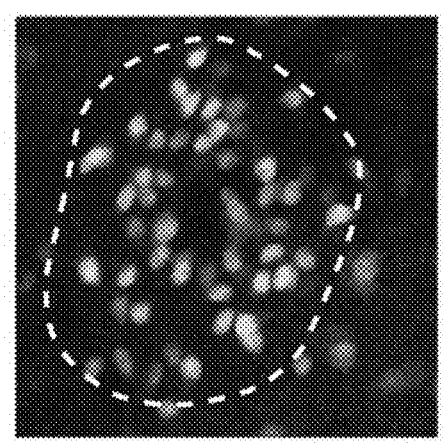
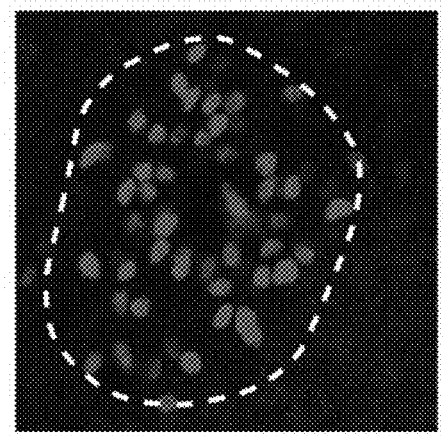
FIG. 6D
FIG. 6E

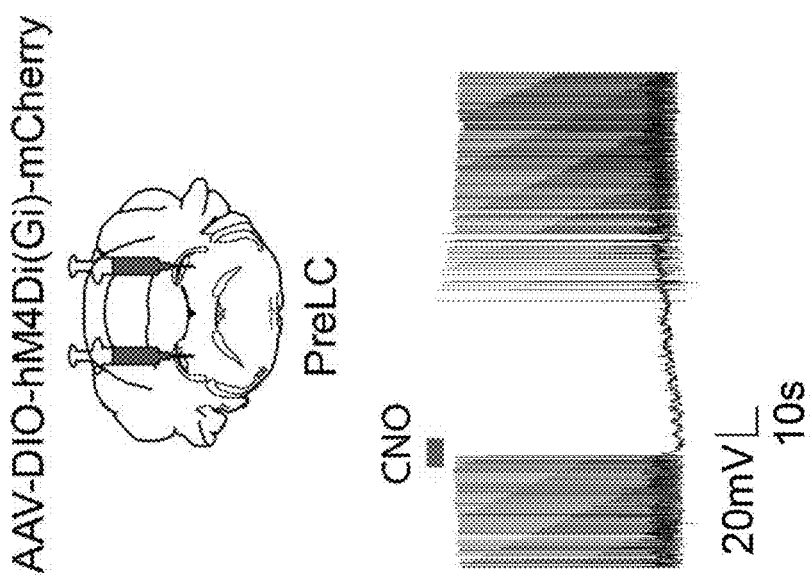
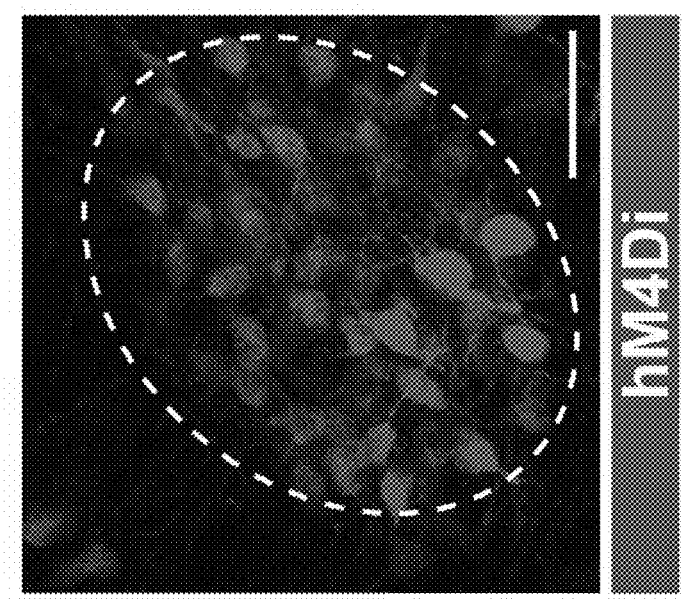
*FIG. 8E*  *FIG. 8F*

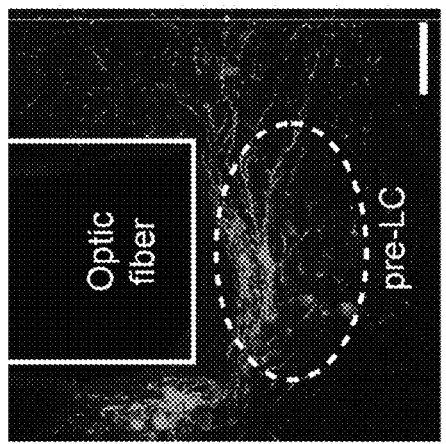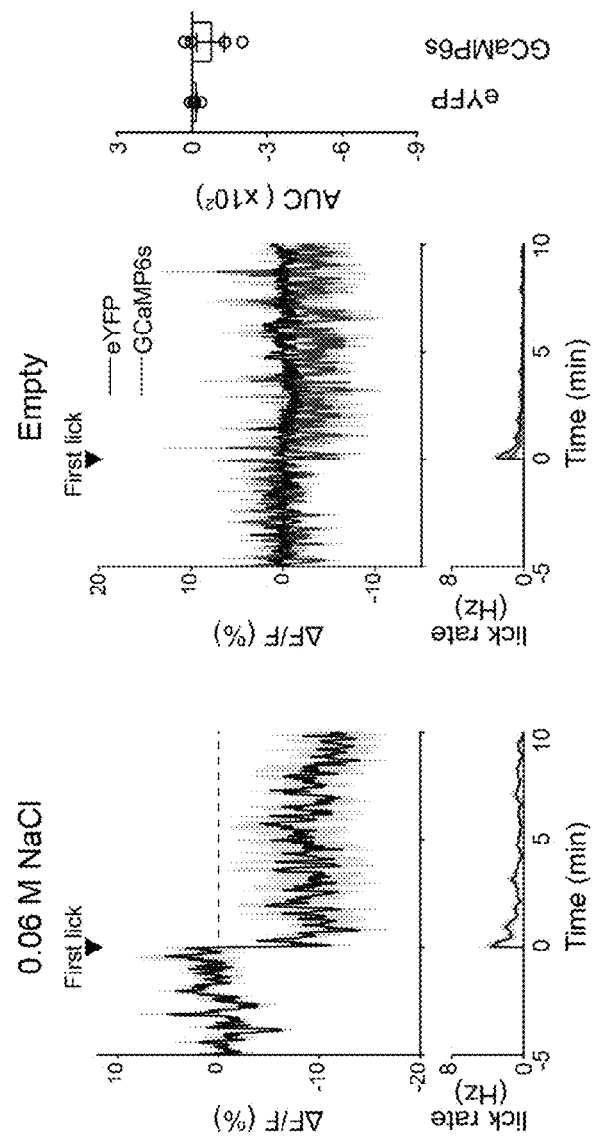
FIG. 10A
FIG. 10B
FIG. 10C

METHODS AND COMPOSITIONS FOR MODULATING APPETITE AND INTAKE OF SODIUM

RELATED APPLICATIONS

The present application claims priority under 35 U.S.C. § 119(e) to U.S. Provisional Application No. 62/792,257, filed on Jan. 14, 2019. The content of this related application is herein expressly incorporated by reference in its entirety.

STATEMENT REGARDING FEDERALLY SPONSORED R&D

This invention was made with government support under Grant No. MH113030 & NS109997 awarded by the National Institutes of Health. The government has certain rights in the invention.

BACKGROUND

Field of the Application

The present application relates generally to methods and compositions for modulating sodium appetite and/or intake, and identification of modulators for sodium appetite and/or intake.

Description of the Related Art

Sodium is the main cation in the extracellular fluid that regulates various physiological functions. Sodium-depletion in the body elevates the hedonic value of sodium taste, which drives animals toward sodium consumption. Conversely, oral sodium detection rapidly promotes satiation of sodium appetite, suggesting that chemo sensory signals have a central role in sodium appetite and its satiety. However, the neural basis of chemo sensory-based appetite regulation remains poorly understood. There is still a need for identifying modulators for sodium appetite and/or intake, as well as developing methods and composition for modulating sodium appetite and/or intake in subjects in need thereof.

SUMMARY

Disclosed herein include a method of reducing sodium appetite in a subject in need thereof. The method, in some embodiments, comprises: inhibiting a plurality of prodynorphin (PDYN)-positive neurons in the pre-locus coeruleus (pre-$LC^{PDYN}$ neurons) of the subject, thereby reducing sodium appetite in the subject. For example, the method can comprise determining sodium intake in the subject before inhibiting the plurality of pre-$LC^{PDYN}$ neurons of the subject, after inhibiting the plurality of pre-$LC^{PDYN}$ neurons of the subject, or both.

The method can be used to reduce the sodium appetite to various extent. For example, the sodium appetite of the subject can be reduced by at least 50%, at least 60%, at least 70%, at least 80%, or more. In some embodiments, reducing sodium appetite in the subject comprises reducing sodium ingestion for the subject. In some embodiments, at least 50% of the plurality of pre-$LC^{PDYN}$ neurons express forkhead box protein P2 (FOXP2). In some embodiments, inhibiting the plurality of pre-$LC^{PDYN}$ neurons of the subject comprises oral contact of sodium without sodium ingestion in the subject. Inhibiting the plurality of pre-$LC^{PDYN}$ neurons of the subject, in some embodiments, comprises stimulating a plurality of GABAergic neurons in the bed nucleus of the stria terminalis (BNST), central amygdala, or both of the subject. The plurality of GABAergic neurons can be, for example, in BNST, central amygdala, or both of the subject comprises PDYN-positive neurons. In some embodiments, inhibiting the plurality of pre-$LC^{PDYN}$ neurons of the subject comprises inhibiting a plurality of HSD2 neurons in the nucleus of solitary tract ($NTS^{HSD2}$ neurons) in the subject.

In some embodiments, inhibiting the plurality of pre-$LC^{PDYN}$ neurons of the subject comprises optogenetic inhibition or chemogenetic inhibition. In some embodiments, inhibiting the plurality of pre-$LC^{PDYN}$ neurons of the subject comprises inhibiting the plurality of pre-$LC^{PDYN}$ neurons by a stimulatory conditional ion modulator.

In some embodiments, inhibiting the plurality of pre-$LC^{PDYN}$ neurons comprises: administering a nucleic acid encoding a stimulatory conditional ion modulator to the subject, wherein the stimulatory conditional ion modulator is activated in response to a stimulus or agonist; and applying an agonist or stimulus of the stimulatory conditional ion modulator to the subject, causing the activation of the stimulatory conditional ion modulator, thereby inhibit the pre-$LC^{PDYN}$ neurons. The stimulatory conditional ion modulator can, for example, comprise a chloride conducting channelrhodopsin (ChloC). In some embodiments, the stimulus comprises an optical stimulus. The agonist can be, for example, clozapine-N-oxide.

In some embodiments, the nucleic acid is administered to the subject in an adeno-associated viral (AAV) vector. The method, in some embodiments, further comprises identifying a subject as a subject in need of reducing sodium appetite. The subject can be, for example, a subject suffering from a kidney disorder, kidney damage, a cardiovascular disease, high blood pressure, overweight, edema, left ventricular hypertrophy, stroke, or a combination thereof. The kidney disorder can be, for example, a chronic kidney disease or kidney failure. In some embodiments, inhibiting the plurality of pre-$LC^{PDYN}$ neurons lasts for at least five minutes in total.

Also disclosed herein includes a method of stimulate sodium appetite in a subject in need thereof. The method, in some embodiments, comprises: stimulating a plurality of prodynorphin (PDYN)-positive neurons in the pre-locus coeruleus (pre-$LC^{PDYN}$ neurons) of the subject, thereby increasing sodium appetite in the subject. The method can comprise, for example, determining sodium intake in the subject before stimulating the plurality of pre-$LC^{PDYN}$ neurons of the subject, after stimulating the plurality of pre-$LC^{PDYN}$ neurons of the subject, or both. The method can increase the sodium appetite of the subject to various extent. For example, the sodium appetite of the subject can be increased by at least 20%, at least 30%, at least 40%, at least 50%, at least 60%, at least 70%, or more.

In some embodiments, stimulating the plurality of pre-$LC^{PDYN}$ neurons of the subject comprises inhibiting a plurality of GABAergic neurons in the bed nucleus of the stria terminalis (BNST), central amygdala, or both of the subject. The plurality of GABAergic neurons in BNST, central amygdala or both of the subject can, for example, comprise PDYN-positive neurons. In some embodiments, stimulating the plurality of pre-$LC^{PDYN}$ neurons of the subject comprises stimulating a plurality of HSD2 neurons in the nucleus of solitary tract ($NTS^{HSD2}$ neurons) in the subject. Stimulating the plurality of pre-$LC^{PDYN}$ neurons of the subject can comprise, for example, optogenetic or chemogenetic stimulation. The subject can be, for example, a subject suffering from hyponatremia, excessive sweating, or a combination thereof.

Further disclosed herein include a method of identifying a modulator for sodium appetite. The method, in some embodiments, comprises: (a) contacting a candidate compound with a plurality of prodynorphin (PDYN)-positive neurons in the pre-locus coeruleus (pre-LC$^{PDYN}$ neurons) of a subject; (b) selecting the candidate compound as a modulator of the pre-LC$^{PDYN}$ neurons if the candidate compound alters an eletrophysiological response in the pre-LC$^{PDYN}$ neurons; (c) assessing the change in valence toward sodium of the subject in response to the administration of the selected candidate compound; and (d) identifying the candidate compound as a modulator for sodium appetite if the candidate compound changes the valence toward sodium of the subject compared to a control. The eletrophysiological response can be measured by, for example, a $Ca^{2+}$ influx assay, a patch clamp assay, a calcium mobilization assay, a calcium imaging assay, an electrical signal detection assay, an assay based on fluorescent calcium sensor GCaMP6s, or a combination thereof.

In some embodiments, contacting the candidate compound with the plurality of pre-LC$^{PDYN}$ neurons comprises administering the candidate compound to the subject via injection. The modulator can be, for example, a suppressor for sodium appetite and step (d) comprises identifying the candidate compound as a suppressor for sodium appetite if the candidate compound reduces valence toward sodium of the subject compared to a control. In some embodiments, the modulator is an enhancer for sodium appetite and step (d) comprises identifying the candidate compound as an enhancer for sodium appetite if the candidate compound enhances valence toward sodium of the subject compared to a control. The candidate compound can be a small molecule, a peptide, a nucleic acid, or a combination thereof.

BRIEF DESCRIPTION OF THE DRAWINGS

The patent or application file contains at least one drawing executed in color. Copies of this patent or patent application publication with drawing(s) will be provided by the Office upon request and payment of the necessary fee.

FIG. 1A: c-Fos expression in sated (control), water-deprived, sodium-depleted, or sodium-repleted (rescue) animals. Quantified data are shown (n=4 mice for rescue, n=5 mice for other conditions). FIG. 1B: Sodium-depletion activates pre-LC excitatory neurons (n=5 mice). D+ denotes double-positive. FIG. 1C: c-Fos expression fully overlaps with PDYN-positive neurons visualized in PDYN/Ai1 10 transgenic mice (n=5 mice). FIG. 1D: Representative image of optic fiber placement in the pre-LC. FIG. 1E: Photostimulation of pre-LC$^{PDYN}$ neurons triggered ingestion of NaCl solution (0.5 M, n=10 mice) compared to water (n=10 mice) or empty spout (n=4 mice). FIG. 1F: Photostimulated mice showed robust licking behavior toward rock salt (n=4 for −Sodium and n=8 for the rest). Raster plots of 3 out of 8 mice are shown. FIG. 1G: A scheme of photostimulation and sodium presentation (left panel). The number of licks for 30 min was quantified (right panel, n=8 mice). FIG. 1H: Photoinhibition of pre-LC$^{PDYN}$ neurons by iC++ significantly reduced sodium intake (n=7 mice). Scale bar, 50 μm. $*P<0.05$, $P<0.01$ and $*P<0.001$ by Kruskal-Wallis, Friedman test (Dunn's multiple comparison), or two-tailed Wilcoxon test.

Data presented as mean±s.e.m. Box plots show median, quartiles (boxes), and range (whiskers).

Figure 2A:
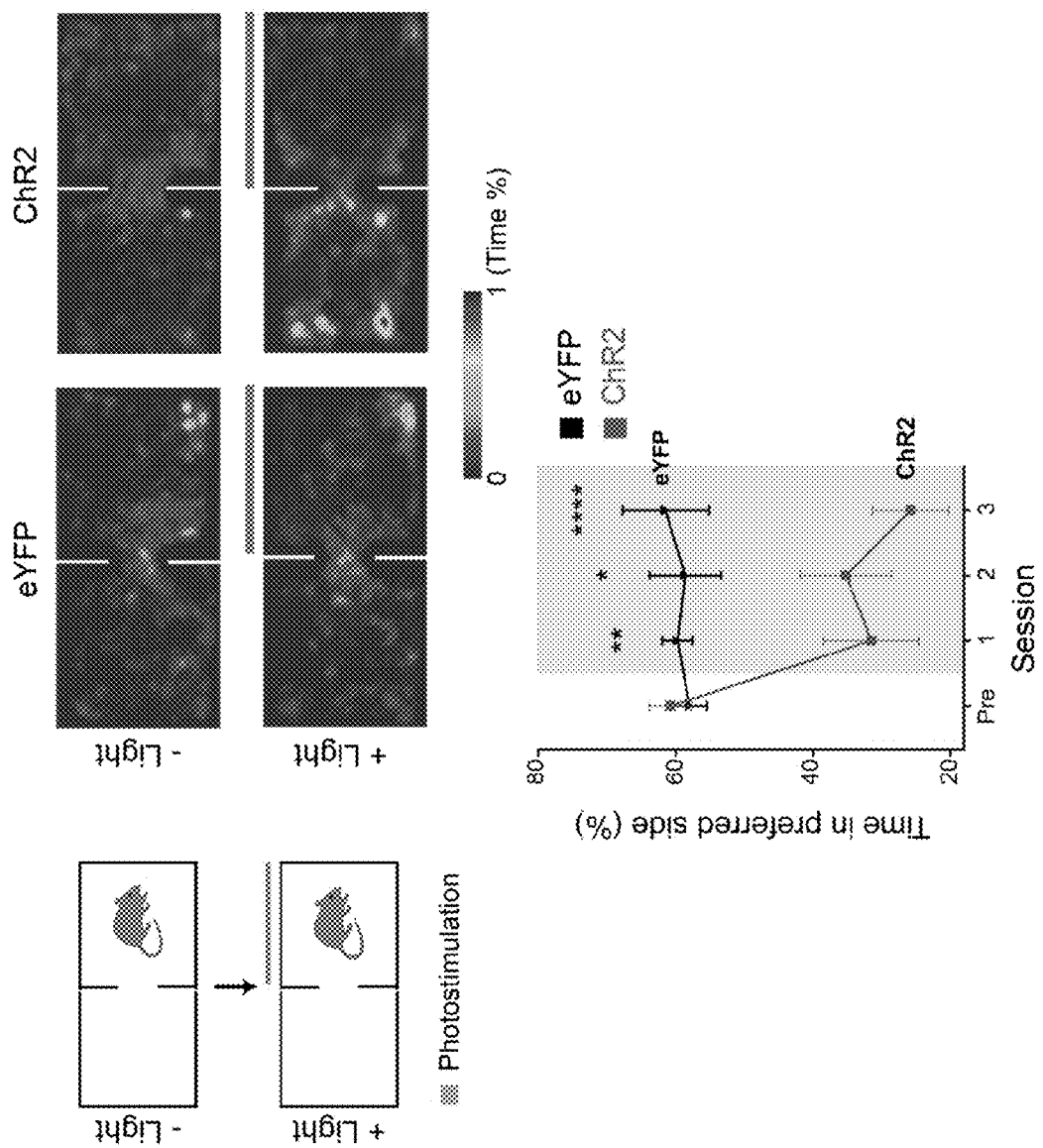
Figure 2B:
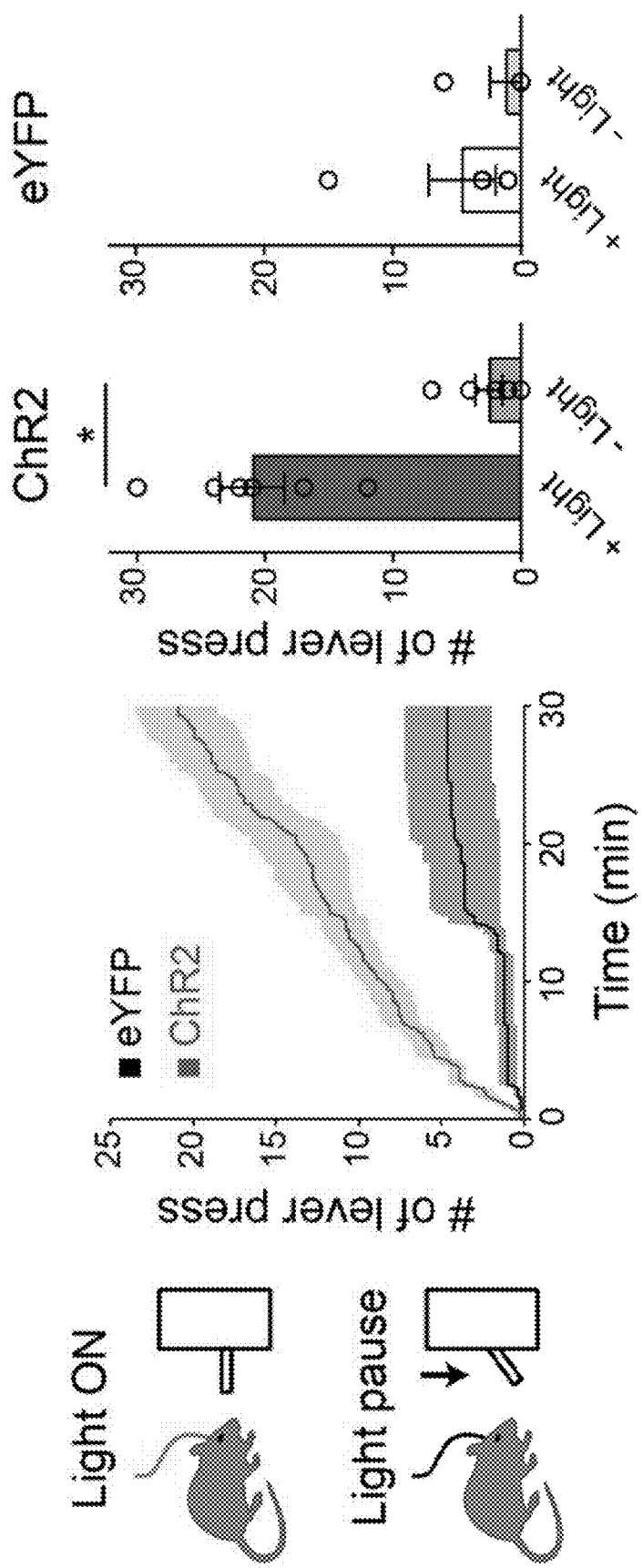

FIGS. 2A-B. Activation of pre-LC$^{PDYN}$ neurons drives an aversive motivational signal. FIG. 2A: Two-chamber real-time place preference assay (left panel). Place preference of a representative animal with or without photostimulation (middle panel). Blue bars indicate the side with light. Quantified data are shown (n=8 mice for eYFP, n=10 mice for ChR2). FIG. 2B: Negative reinforcement assay. Animals were continuously photostimulated (20 Hz) in the chamber, which was paused for 20 sec by each lever press. Cumulative and a total number of lever press were quantified (n=5 and 6 mice for eYFP and ChR2). $*P<0.05$, $P<0.01$, $**P<0.0001$ by two-way repeated measures ANOVA (Sidak's multiple comparisons test) or two-tailed Wilcoxon test. Data presented as mean±s.e.m.

Figure 3A:
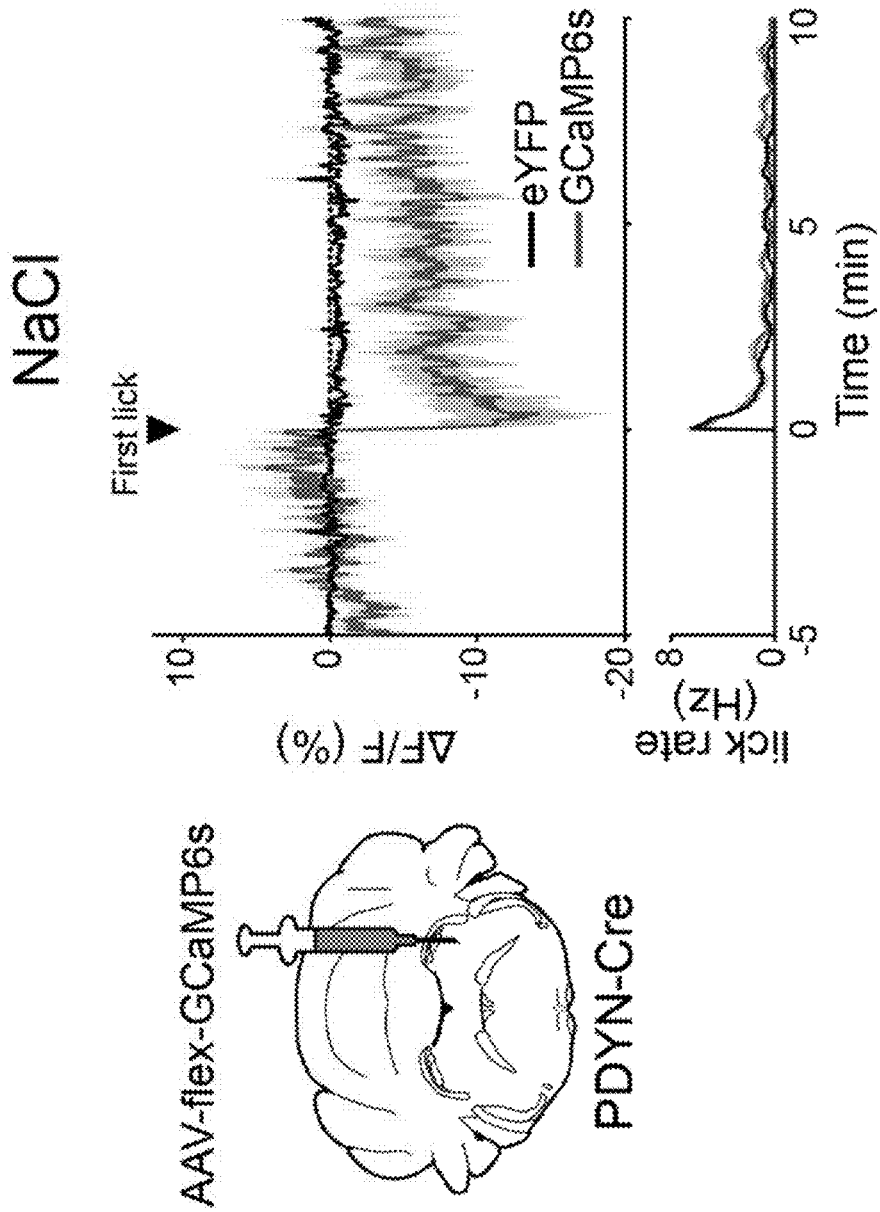
Figure 3C:
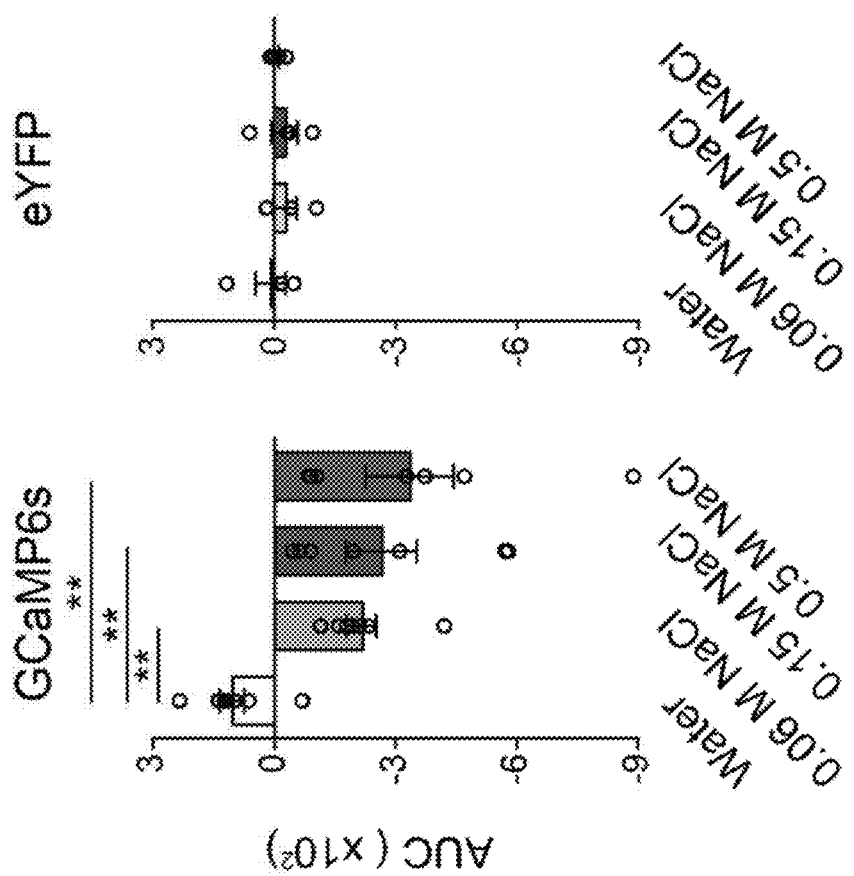
Figure 3B:
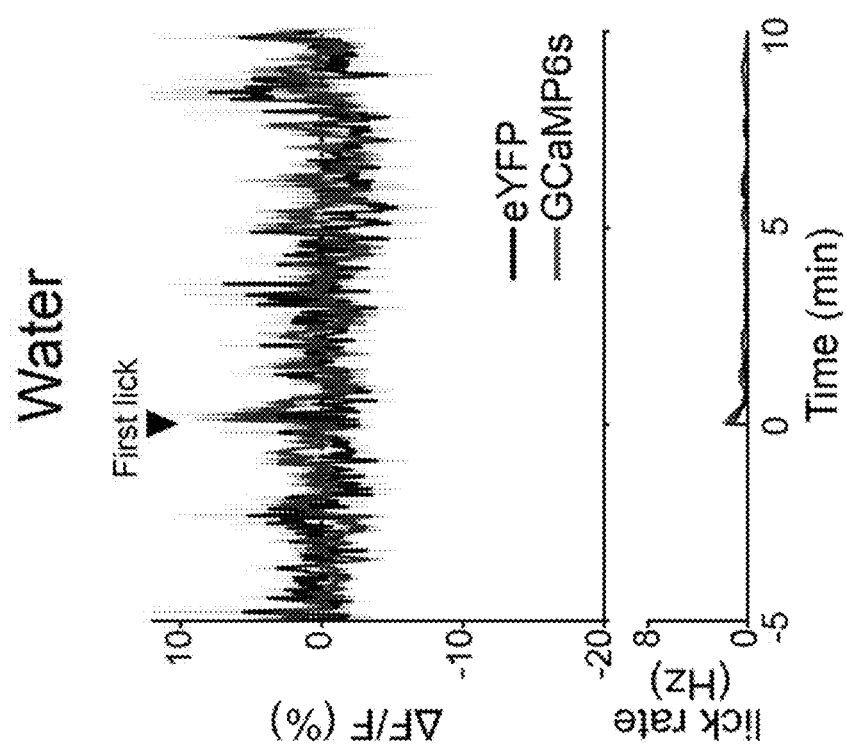
Figures 3D, 3E:
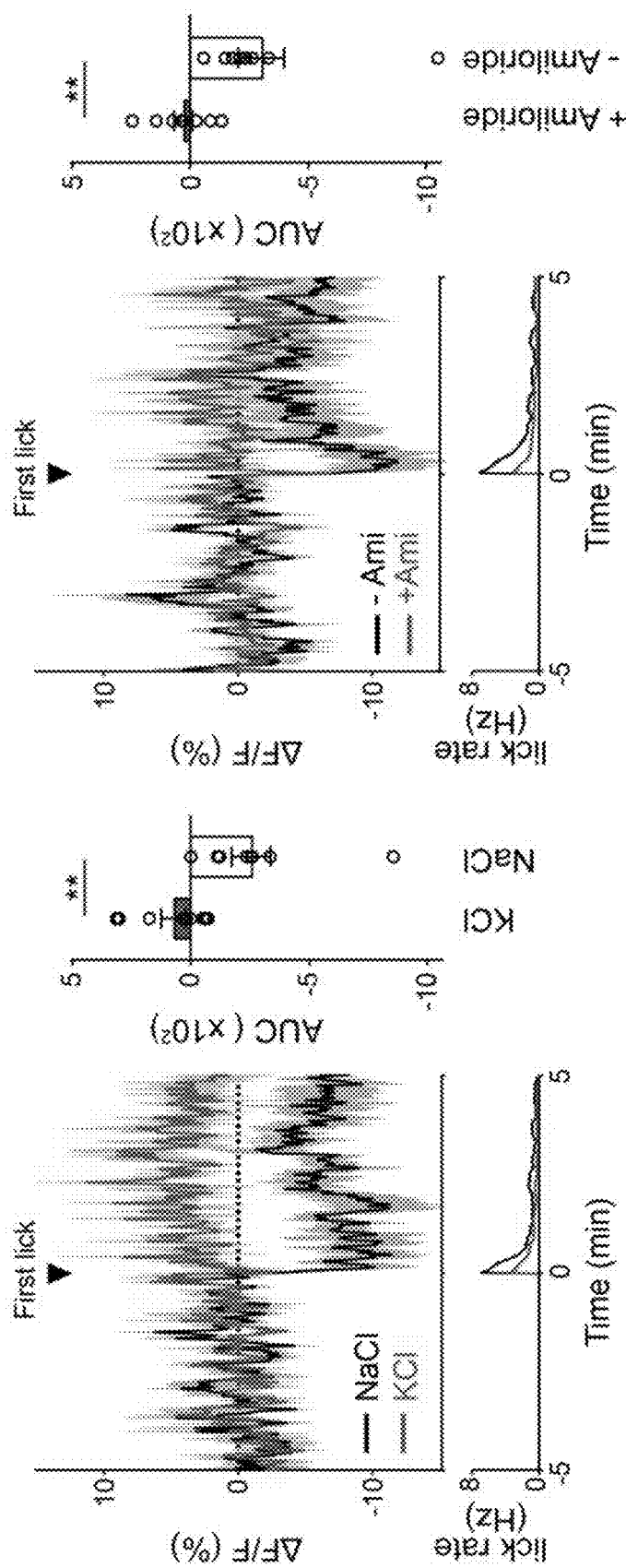
Figure 3F:
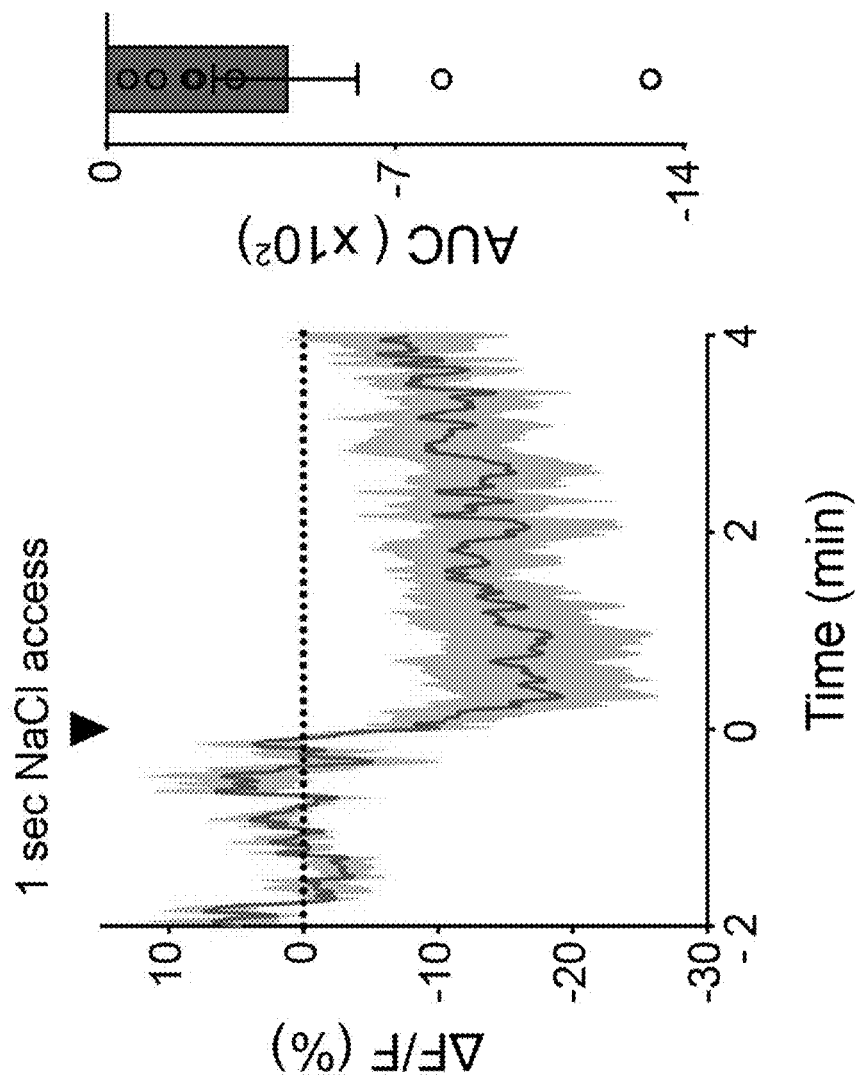

FIGS. 3A-F. Sodium appetite neurons are rapidly modulated by sodium taste signals. FIG. 3A: Photometry recording of GCaMP6s signals from pre-LC$^{PDYN}$ neurons (n=7 mice for eYFP and GCaMP6s). FIG. 3B: No suppression was observed when the animals licked water (n=4 and 8 mice for eYFP and GCaMP6s). FIG. 3C: Fluorescent change (AUC) was calculated upon consumption of water and NaCl solutions (n=4, 7, and 7 mice for eYFP, 0.06 M, and 0.15 M NaCl, respectively). FIG. 3D: Ingestion of KCl did not affect pre-LC$^{PDYN}$ neuron activity (n=9 mice). FIG. 3E: Blocking the ENaC by amiloride eliminated inhibition (n=9 mice). FIG. 3F: A brief NaCl intake for 1 sec induced persistent suppression (n=7 mice). $**P<0.01$ by Kruskal-Wallis test (Dunn's multiple comparison) or two-tailed Wilcoxon test. Data presented as mean±s.e.m.

Figure 4A:
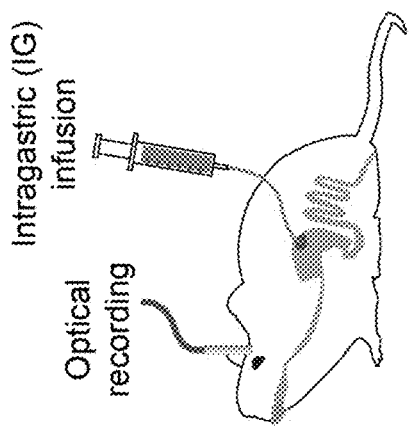
Figure 4B:
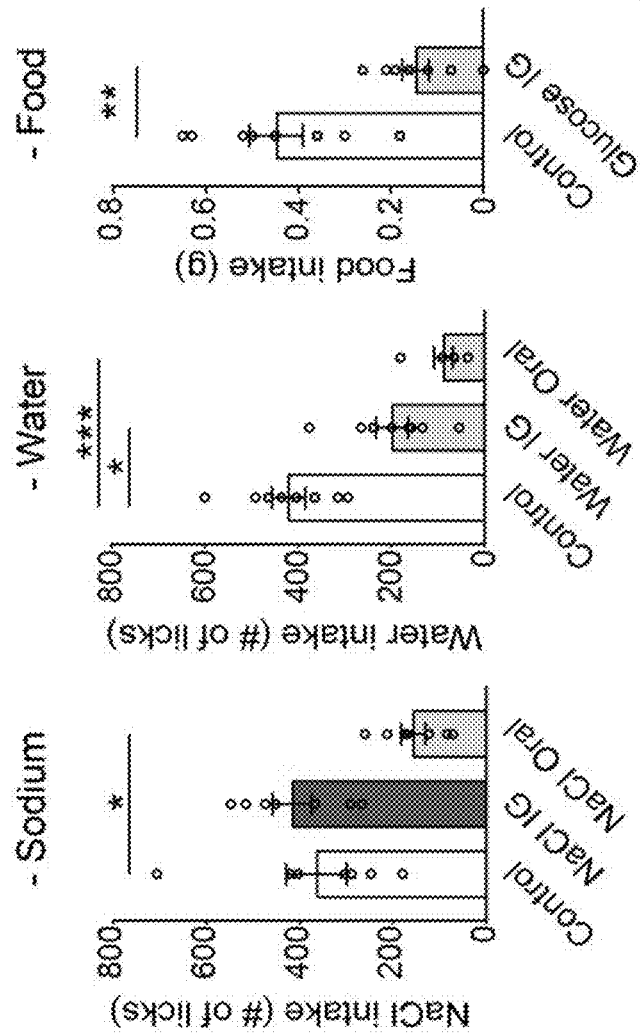
Figures 4C, 4D:
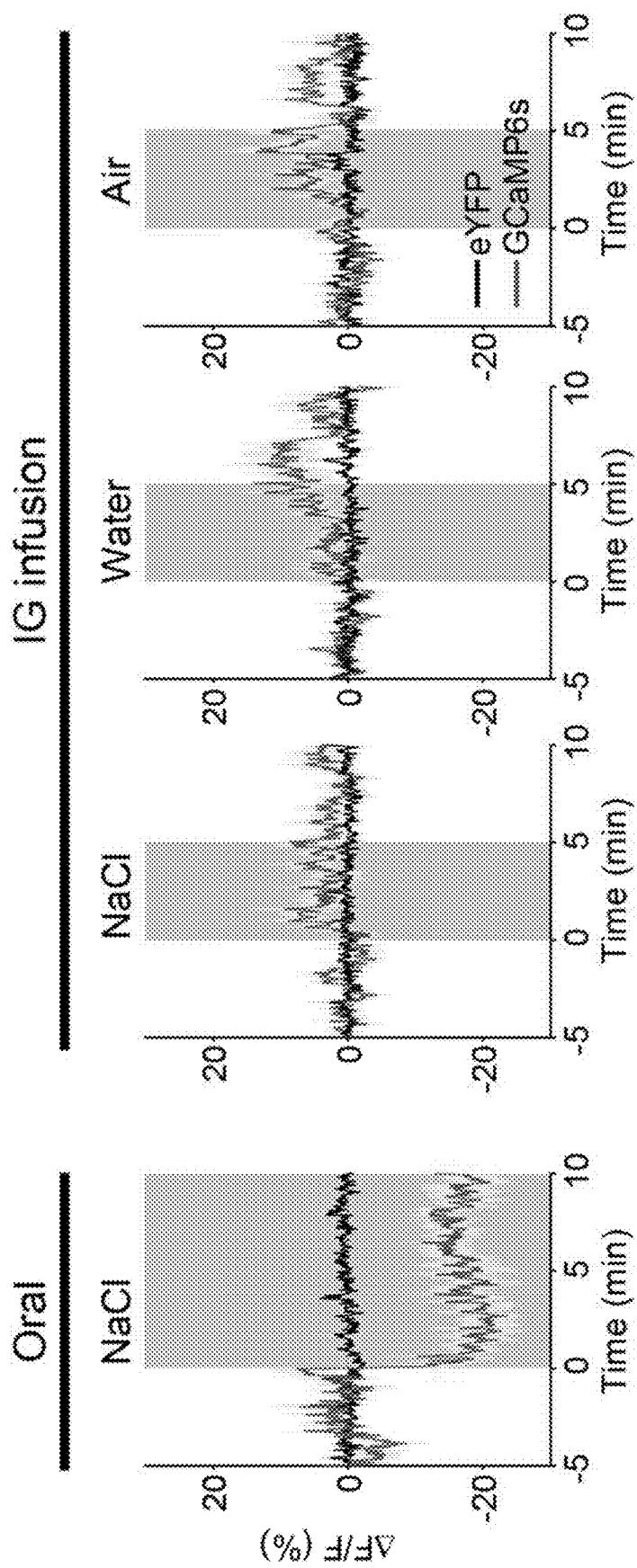
Figure 4E:
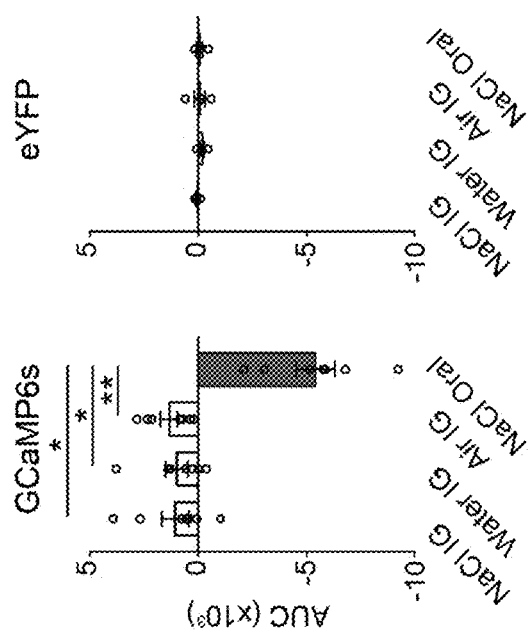

FIGS. 4A-E. Oral sodium detection promotes satiety of sodium appetite by suppressing pre-LC$^{PDYN}$ neurons. FIG. 4A: Simultaneous optical recording of pre-LC$^{PDYN}$ neurons and intragastric (IG) infusion. FIG. 4B: The effects of gastric infusion of sodium, water, and glucose (5M) on subsequent ingestive behaviors for 10 min (n=7 mice for NaCl, n=6 mice for water oral, n=8 mice for controls, water IG and glucose IG). FIG. 4C: Oral sodium consumption suppressed pre-LC$^{PDYN}$ neuron s activity (n=4 and 7 mice for eYFP and GCaMP6s). FIG. 4D: However, fluorescence signals were not affected by IG infusion of NaCl, water, or air. FIG. 4E: Quantification of FIGS. 4C and 4D. $*P<0.05$, $P<0.01$ and $*P<0.001$ by Friedman, Kruskal-Wallis test (Dunn's multiple comparison), or two-tailed Wilcoxon test. Data presented as mean±s.e.m.

Figure 5A:
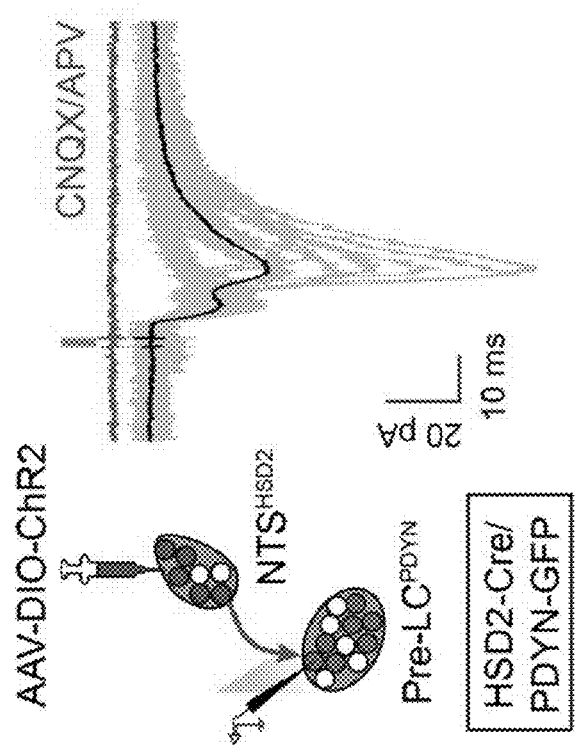
Figure 5B:
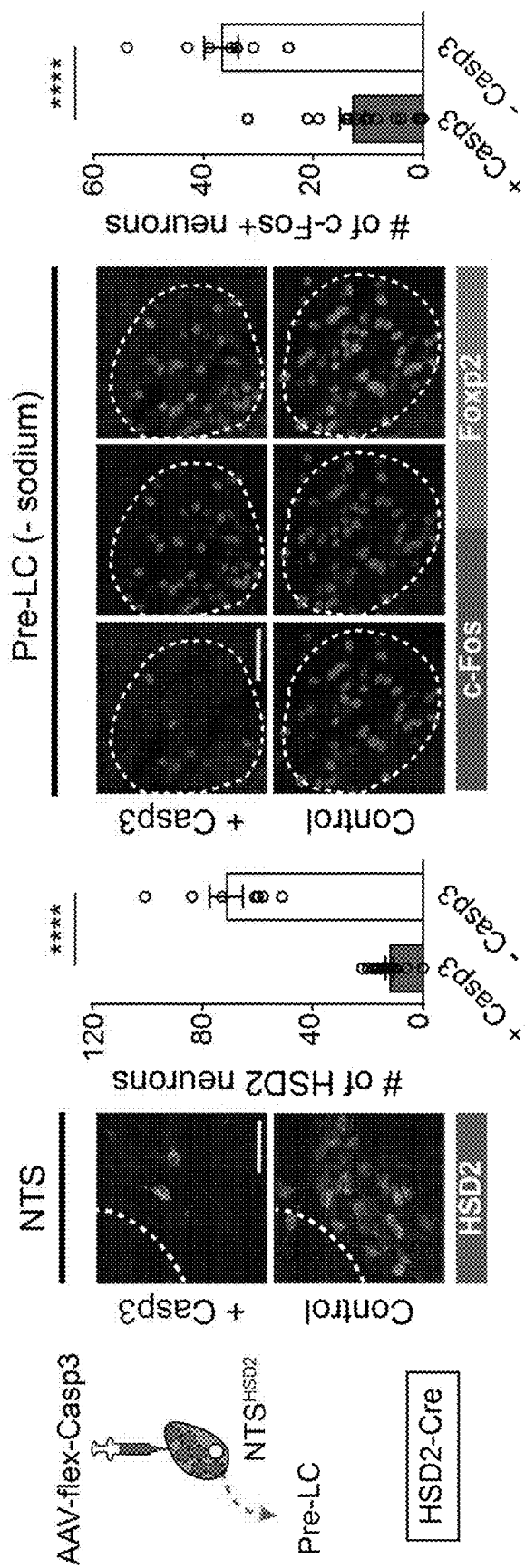
Figure 5C:
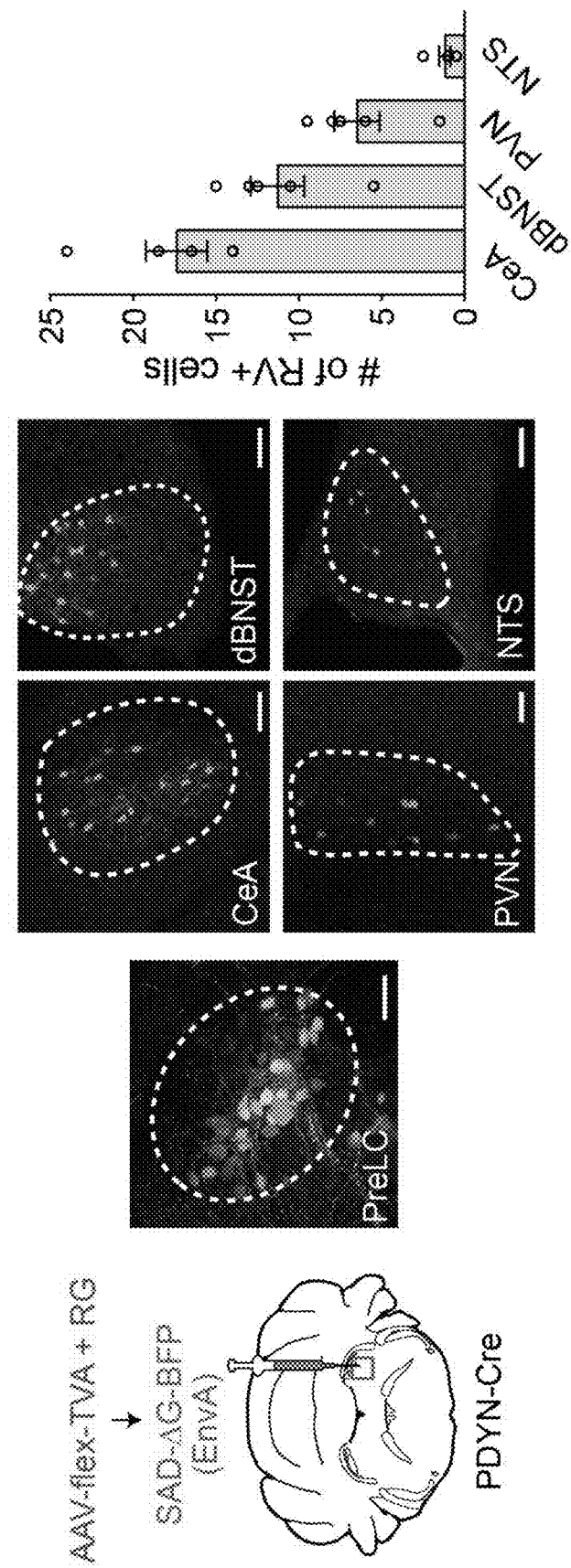

FIGS. 5A-F. Pre-LC$^{PDYN}$ neurons receive both homeostatic and sensory inputs. FIG. 5A: NTS$^{HSD2}$ neurons send monosynaptic inputs to pre-LC$^{PDYN}$ neurons (23/38 neurons) with an EPSC latency 6.3 msec. FIG. 5B: Ablation of NTS$^{HSD2}$ by AAV-flex-Casp3 (left panels) drastically reduced the pre-LC activity under sodium depletion (right panels, n=18 from 9 mice for +Casp3, and n=8 from 4 mice for −Casp3). Pre-LC$^{PDYN}$ neurons were visualized by Foxp2 immunostaining. FIG. 5C: Monosynaptic rabies tracing from pre-LC$^{PDYN}$ neurons (left panel). Representative images of the pre-LC, CeA, dBNST, PVN, and NTS (middle panels), and the number of SAD-positive neurons (right panel) was quantified (n=5 mice). FIG. 5D: Monosynaptic dBNST$^{PDYN}$→pre-LC$^{PDYN}$ projections. A magnified image from c showing that SAD-AG-BFP overlaps with PDYN expression in the dBNST (upper panels, 71.7±6.8%, n=5). Control tracing experiments without RG are shown (bottom panels). FIG. 5E: Monosynaptic inhibitory connections of dBNST$^{PDYN}$→pre-LC$^{PDYN}$ (28/44 neurons) with an IPSC latency of 7 msec. FIG. 5F: GCaMP6s was retrogradely delivered to dBNST→pre-LC neurons by infecting CAV- Cre in the pre-LC and AAV-flex-GCaMP6s in the dBNST. Shown are calcium responses of dBNST→pre-LC neurons toward sodium with or without amiloride (n=7 mice). Scale bar, 50 µm. *$P<0.05$, ****$P<0.0001$ by two-tailed Wilcoxon or two-tailed Mann-Whitney test. Data presented as mean±s.e.m.

Figure 6B:
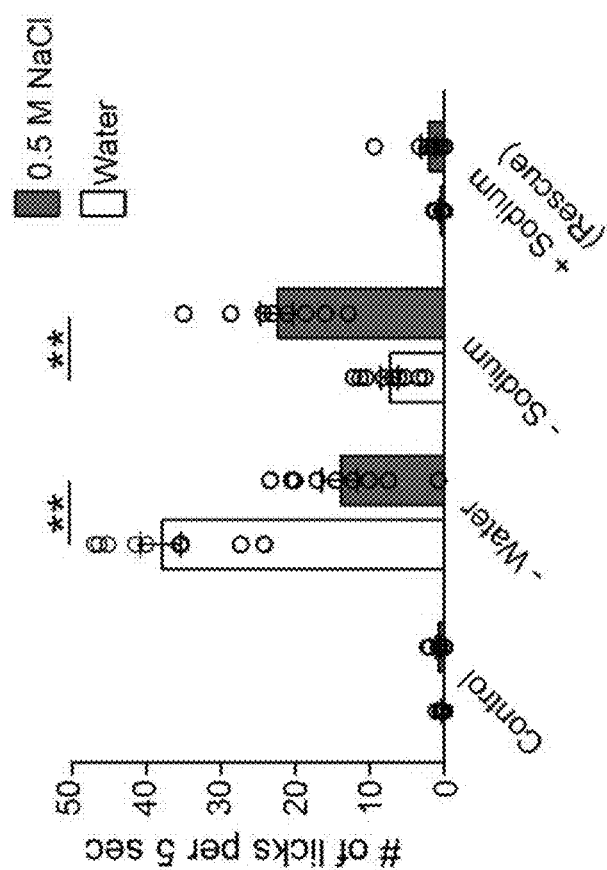
Figure 6A:
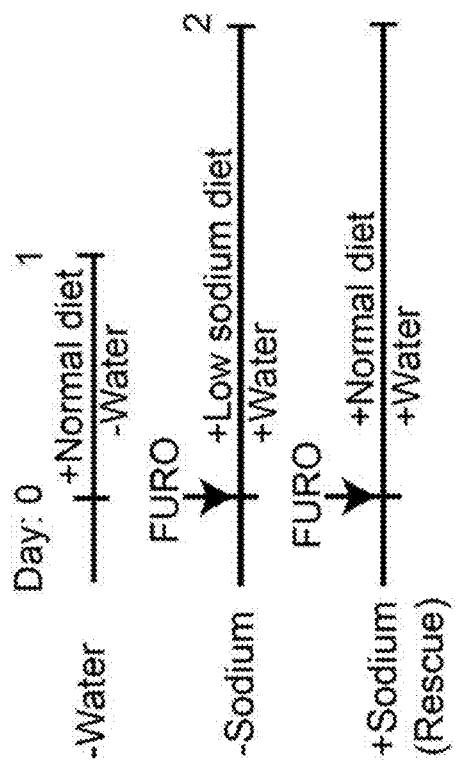
Figure 6C:
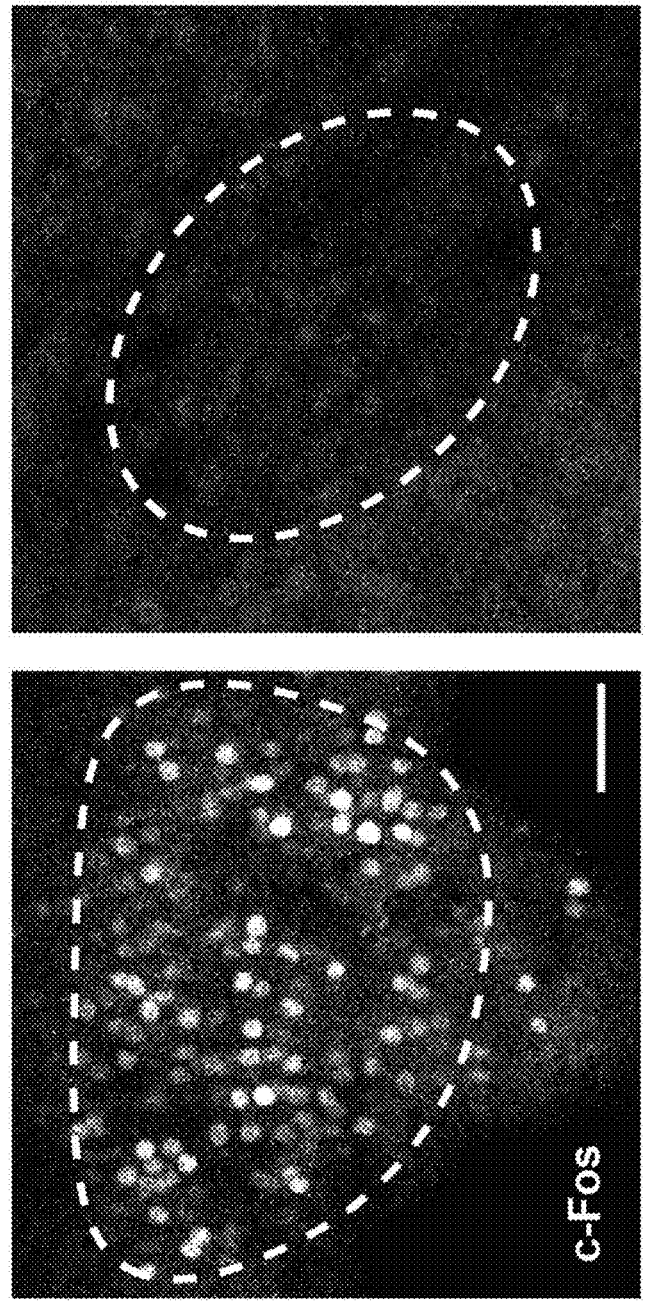

FIGS. 6A-E. Behavioral paradigms for sodium appetite induction and histological analysis of the pre-LC. FIG. 6A: Experimental protocols for inducing thirst and sodium appetite. Intraperitoneal injection of furosemide (50 mg/kg body weight) was used to induce sodium appetite. FIG. 6B: Sodium-depleted animals showed a strong preference for sodium while water-deprived animals preferred water over sodium (n=9 mice). FIG. 6C: Water-deprivation for 48 hrs induced robust c-Fos expression in the subfornical organ. However, it did not activate the pre-LC (one out of 4 mice). FIG. 6D: Fluorescence in situ hybridization (FISH) showing that PDYN-Cre expression (visualized in Ai3 transgenic line, green) overlaps with endogenous PDYN transcripts in the pre-LC (red, one out of 2 mice). FIG. 6E: Pre-LC$^{PDYN}$ neurons also overlap with Foxp2 expression, a known marker in the pre-LC (93.8±1.1%, n=3 mice). Scale bar, 50 µm. **$P<0.01$ by two-tailed Wilcoxon test. Data presented as mean±s.e.m.

Figure 7A:
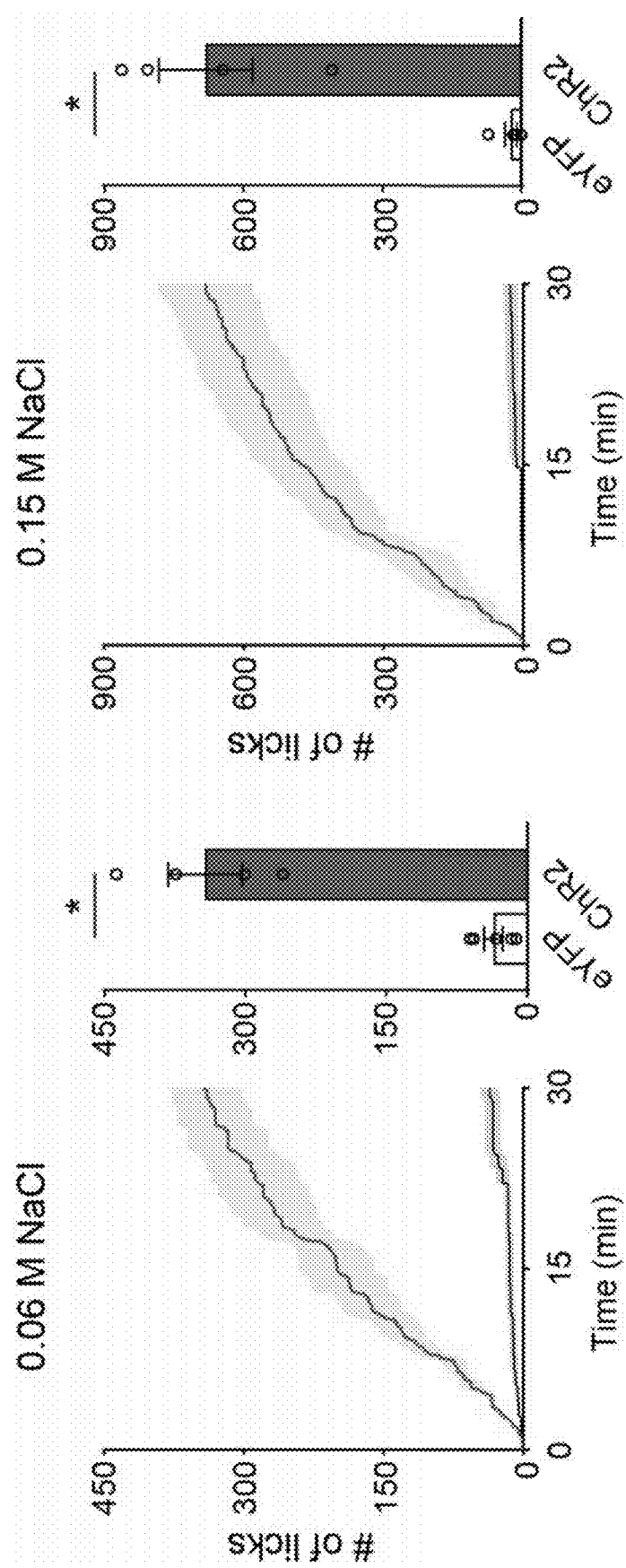
Figure 7B:
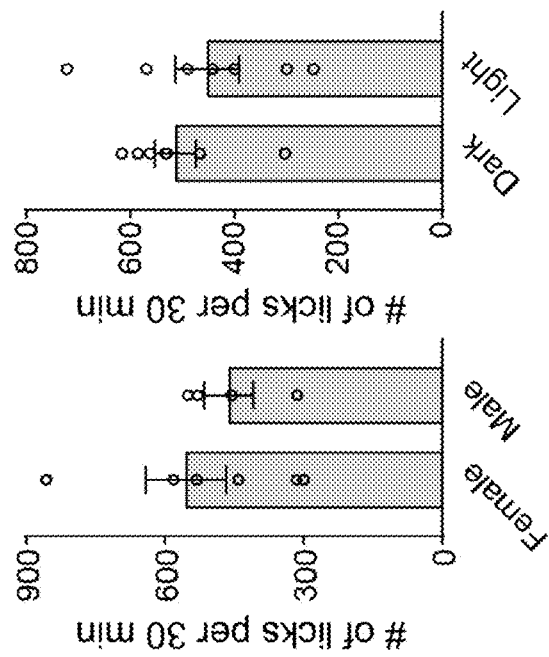
Figure 7C:
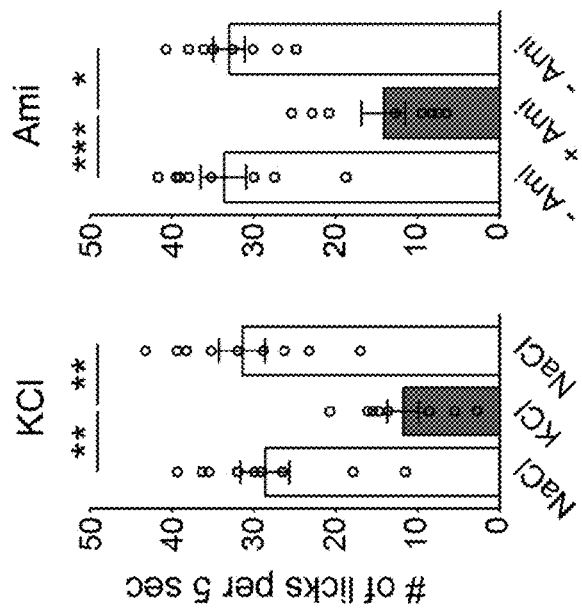
Figure 7D:
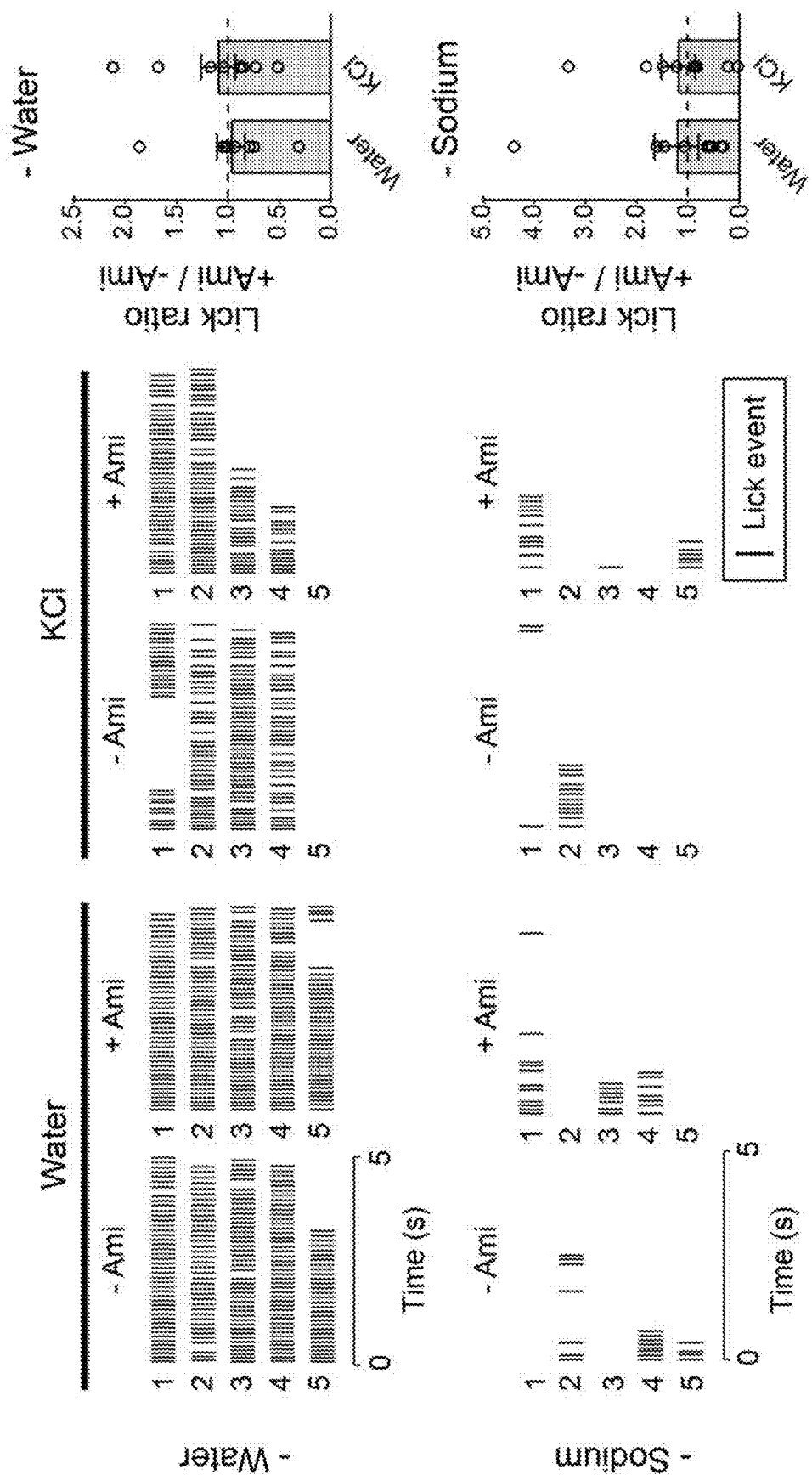

FIGS. 7A-D. Sodium appetite induced by the photostimulation of pre-LC$^{PDYN}$ neurons. FIG. 7A: Photo stimulation of pre-LC$^{PDYN}$ neurons increased intake of a lower concentration of NaCl (0.06 M and 0.15 M, n=5 mice for eYFP, n=4 mice for ChR2). FIG. 7B: Photo stimulation triggered sodium appetite in both sexes (left panel, n=7 for female, n=4 mice for male), at any time of the day (right panel, n=7 mice). Data were partially reanalyzed from FIGS. 1E and 1G. FIG. 7C: Pre-LC$^{PDYN}$-stimulated animals preferred NaCl over KCl (left panel, n=9 mice). NaCl consumption was reduced in the presence of amiloride (right panel, n=8 mice). 0.5 M solutions were used for NaCl and KCl. FIG. 7D: Representative plots showing lick events during the 5-sec of water or KCl access (left panels). The effect of amiloride on water and KCl intake was quantified under water-deprivation and sodium-depletion (right panels). The total number of licks from 5 trials with amiloride was averaged and divided by that without amiloride (n=9 mice). *$P<0.05$, $P<0.01$, *$P<0.001$ by two-tailed Mann-Whitney test or Friedman test (Dunn's multiple comparison). Data presented as mean±s.e.m.

Figure 8B:
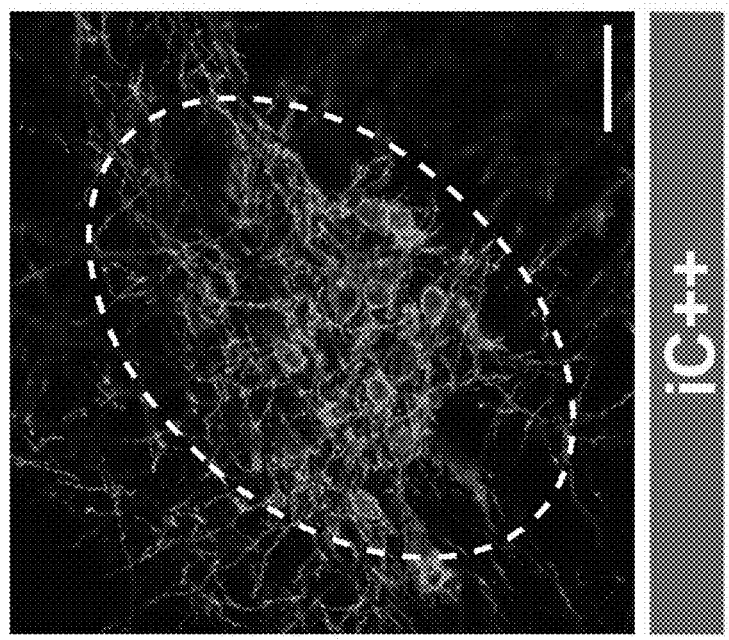
Figure 8A:
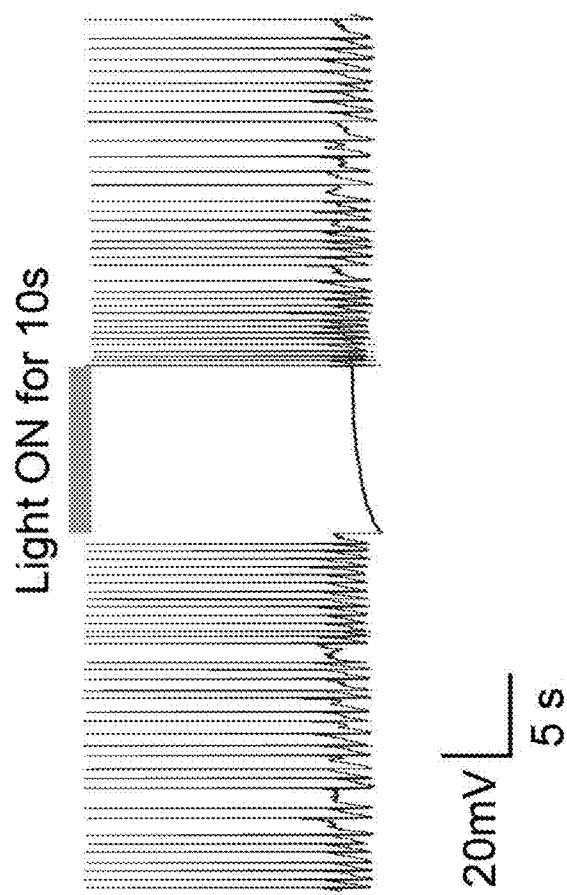
Figures 8C, 8D:
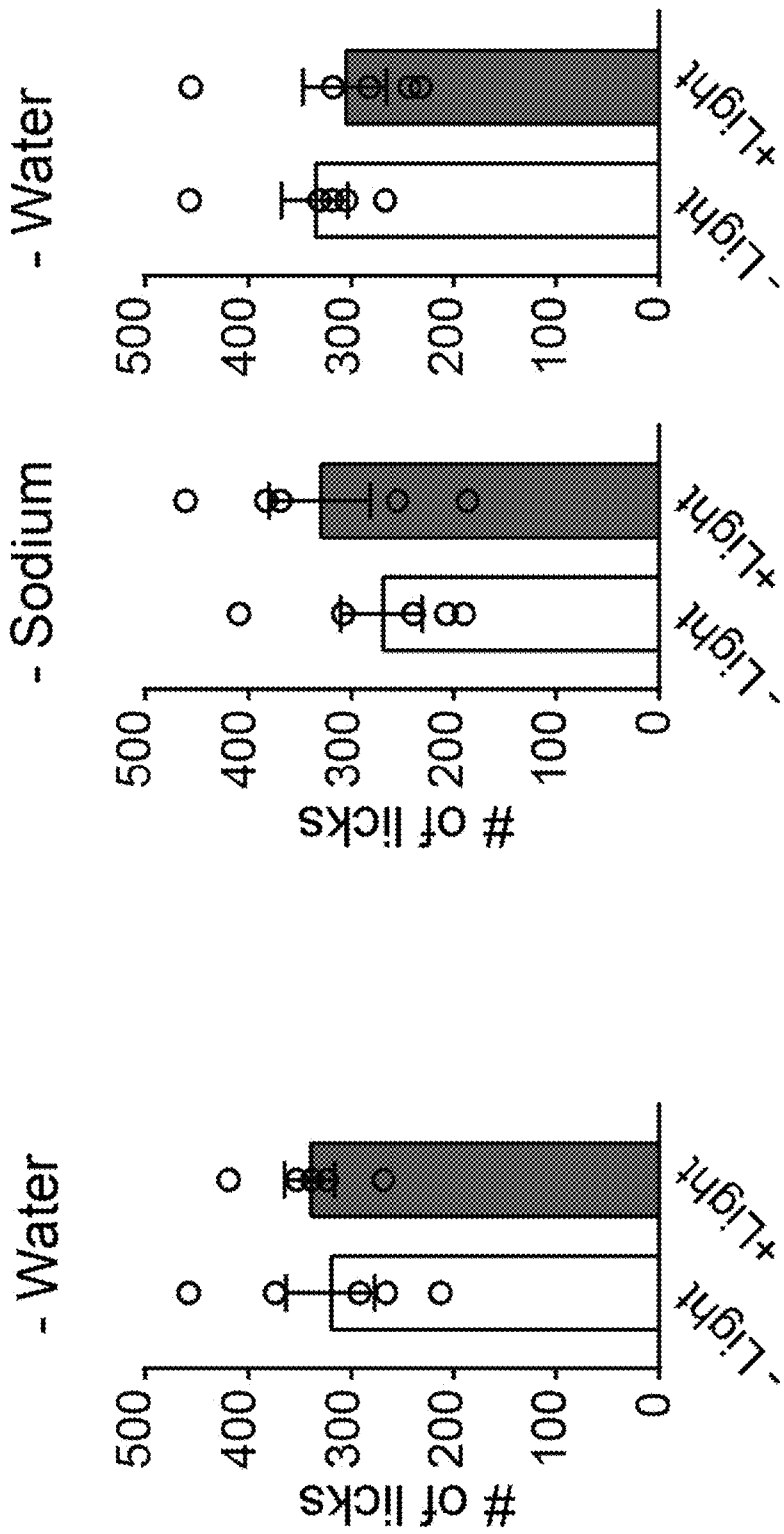
Figure 8H:
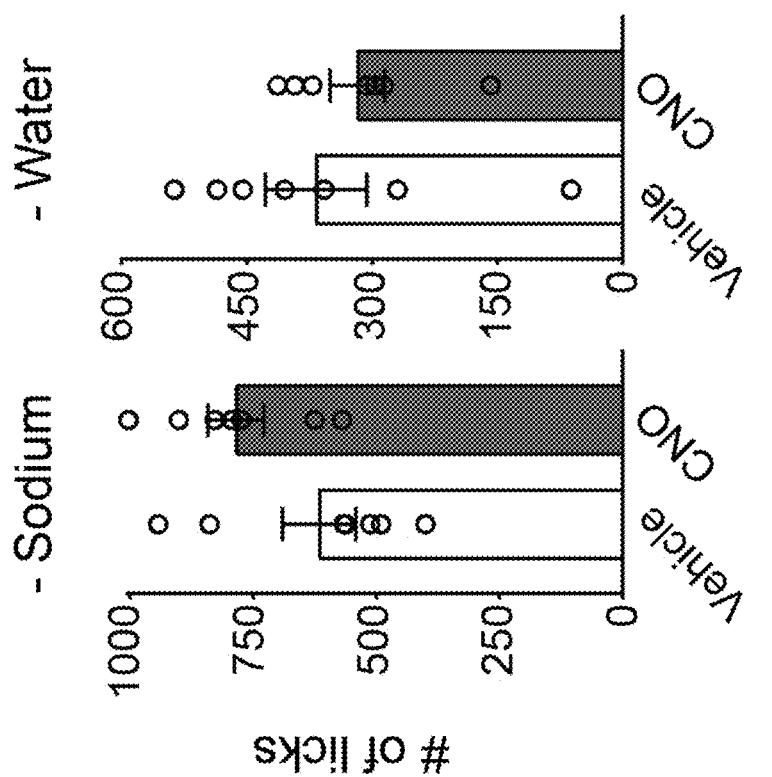
Figure 8G:
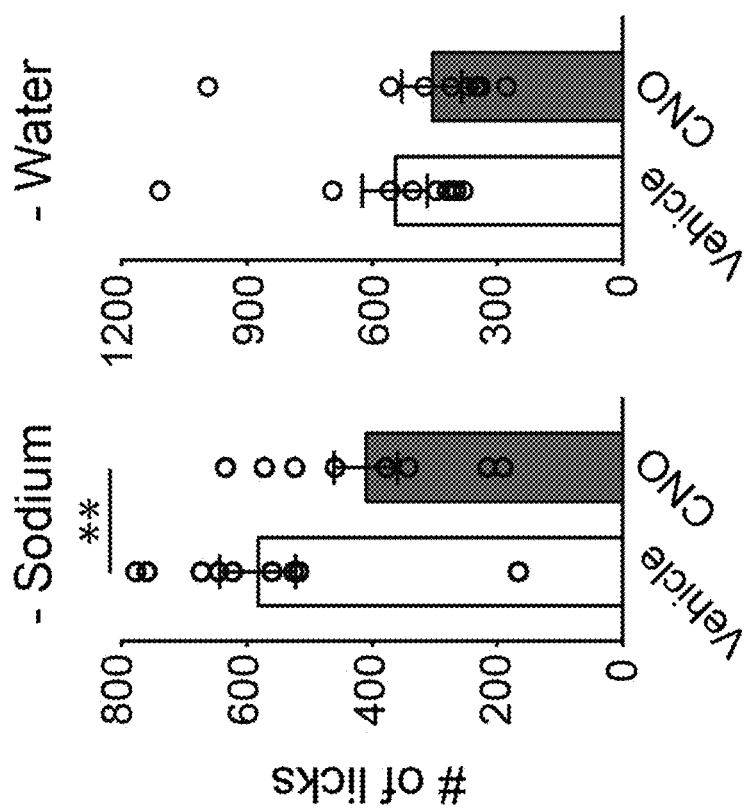

FIGS. 8A-H. Optogenetic and chemogenetic inhibition of pre-LC$^{PDYN}$ neurons. FIG. 8A: Electrophysiological recording in fresh brain slices. Illumination of 473 nm light strongly suppressed firing of pre-LC$^{PDYN}$ neurons expressing iC++ (10 out of 10 neurons from 2 mice). FIG. 8B: A representative image of AAV-DIO-iC++-eYFP expression in the pre-LC of a PDYN-Cre animal (one out of 7 mice). FIG. 8C: Suppression of pre-LC$^{PDYN}$ did not affect water intake in water-deprived animals (n=5 mice). FIG. 8D: AAV-DIO-eYFP controls for optogenetic inhibition (n=5 mice). FIG. 8E: AAV-DIO-hM4Di-mCherry was bilateral injected into the pre-LC. A representative recording demonstrates chemogenetic inhibition of pre-LC$^{PDYN}$ neuron by CNO (13 out of 14 neurons from 2 mice). FIG. 8F: A representative image of AAV-DIO-hM4Di-mCherry expression in the pre-LC (one out of 9 mice). FIG. 8G: Chemogenetic inhibition of pre-LC$^{PDYN}$ neurons reduced sodium intake in sodium-depleted animals. The same manipulation did not affect thirst (n=9 mice). FIG. 8H: CNO administration did not affect thirst or sodium appetite in AAV-DIO-mCherry injected animals (n=7 mice). Scale bar, 50 µm. **$P<0.01$ by two-tailed Wilcoxon test. Data presented as mean±s.e.m.

Figure 9A:
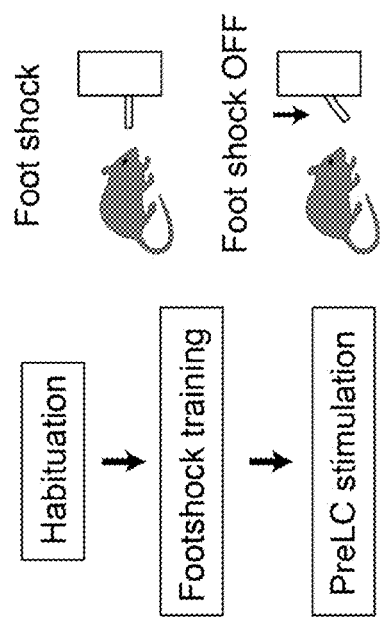
Figure 9C:
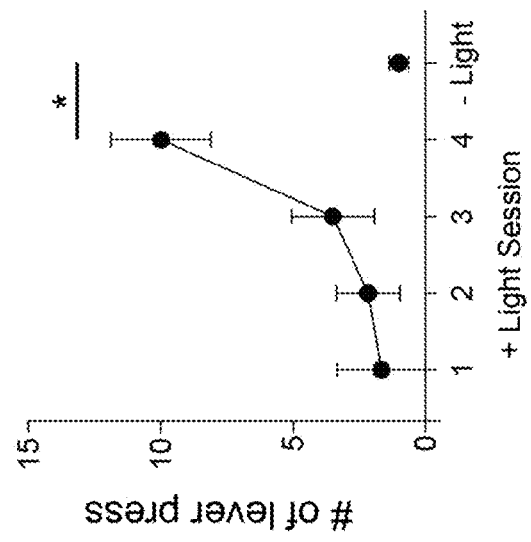
Figure 9B:
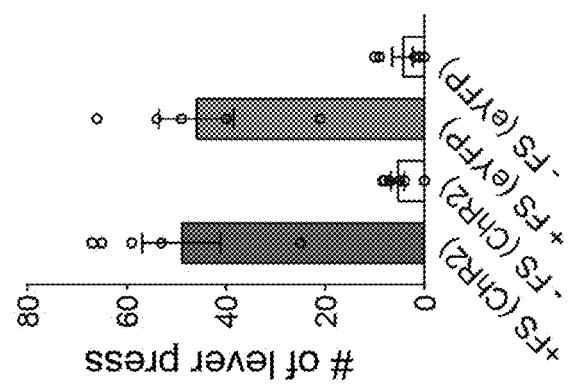

FIGS. 9A-C. Training paradigm for negative reinforcement assay. FIG. 9A: A diagram of training paradigm using foot shock. Each lever press pauses continuous foot shock for 20 sec. FIG. 9B: A total number of lever press in each condition during the 30-min session (n=5 for eYFP and n=6 mice for ChR2). FIG. 9C: Animals were conditioned to perform lever press without foot shock pre-training sessions (n=6 mice). *$P<0.05$ by two-tailed Wilcoxon test. Data presented as mean±s.e.m.

Figure 10E:
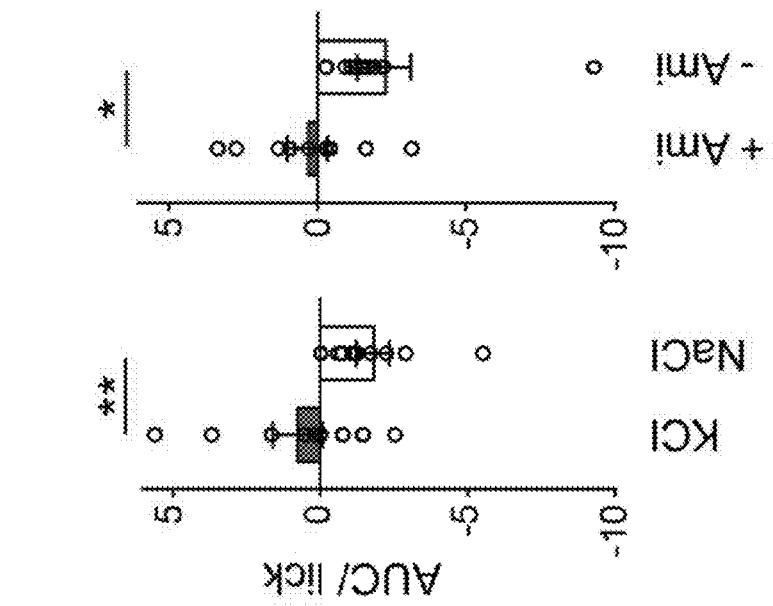
Figure 10D:
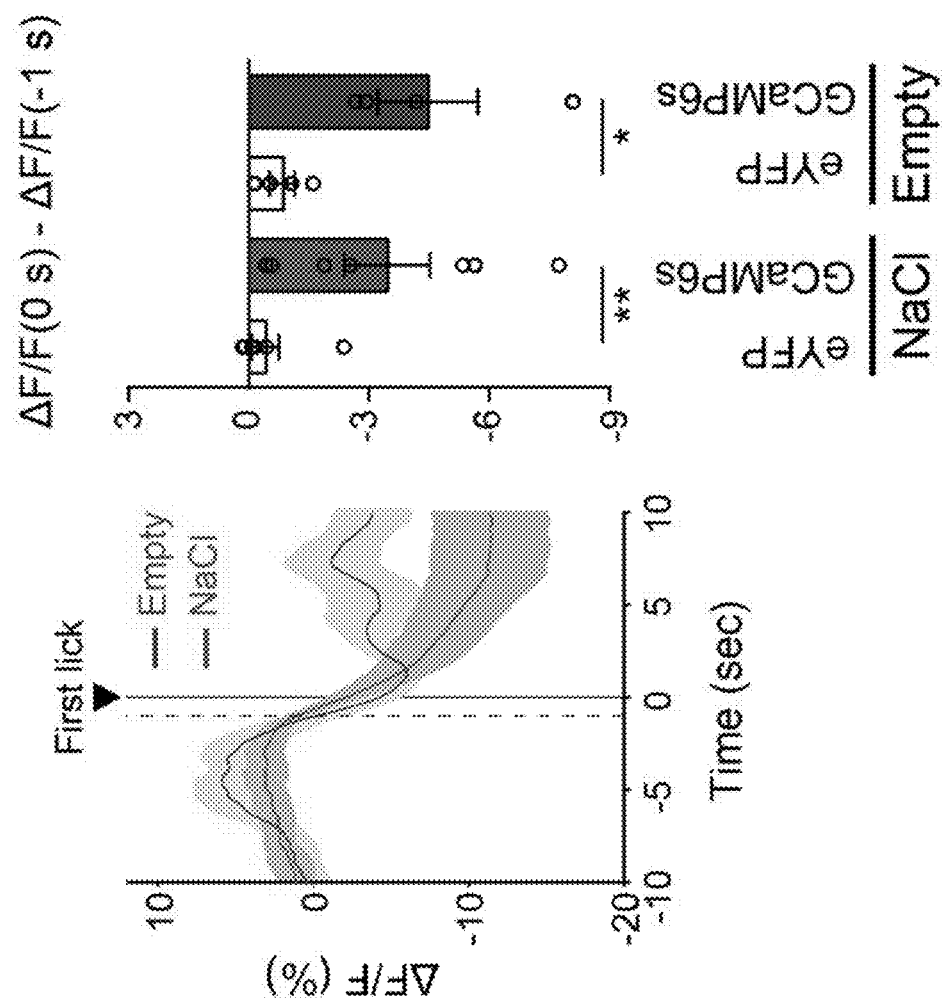

FIGS. 10A-E. In vivo activity of pre-LC$^{PDYN}$ neurons upon ingestive behaviors. FIG. 10A: Placement of an implanted optic fiber and GCaMP6s expression in the pre-LC. Scale bar, 50 µm. FIG. 10B: A low concentration of NaCl exhibited inhibitory effects on pre-LC$^{PDYN}$ neurons (0.06 M, n=7 mice). FIG. 10C: Licking empty spout had no inhibitory effect on pre-LC$^{PDYN}$ neurons (n=4 mice for eYFP, n=4 mice for GCaMP6s). FIG. 10D: Peristimulus time histogram of GCaMP signals around the start of sodium ingestion. Data were magnified from FIG. 10C and FIG. 3A. Fluorescence changes (ΔF/F) from −1 to 0 sec was calculated. FIG. 10E: Activity change per lick was quantified for FIGS. 3D and 3E. *$P<0.05$, **$P<0.01$ by two-tailed Wilcoxon or two-tailed Mann-Whitney test. Data presented as mean±s.e.m.

Figure 11A:
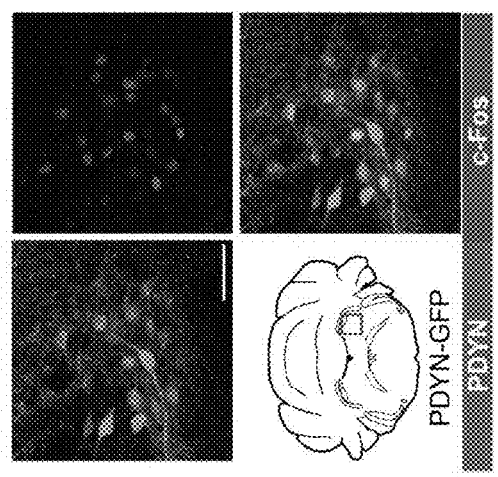
Figure 11B:
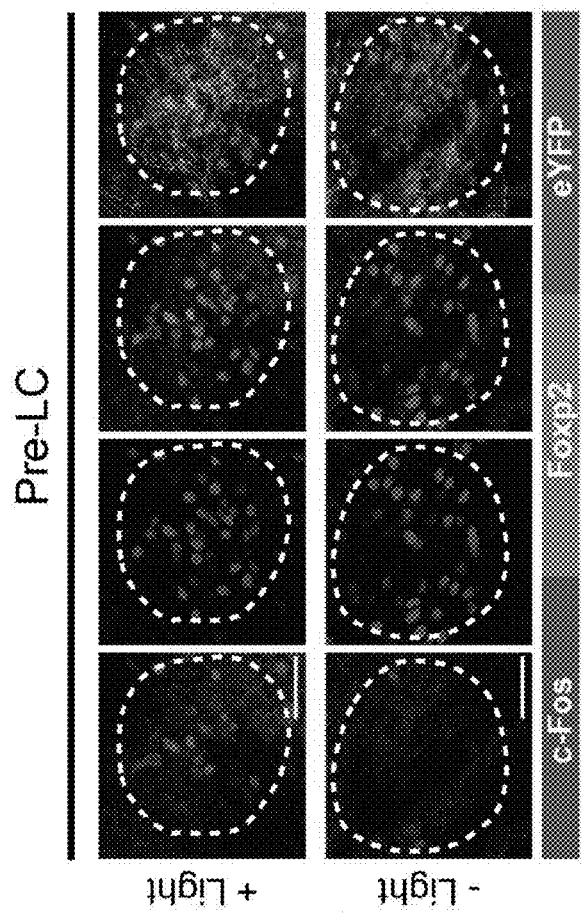
Figure 11B:
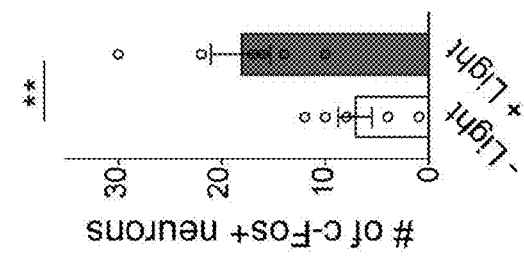
Figure 11B:
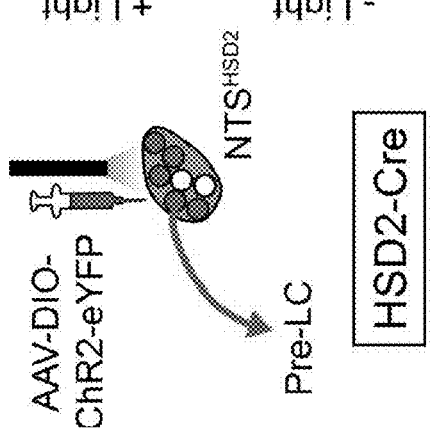
Figure 11D:
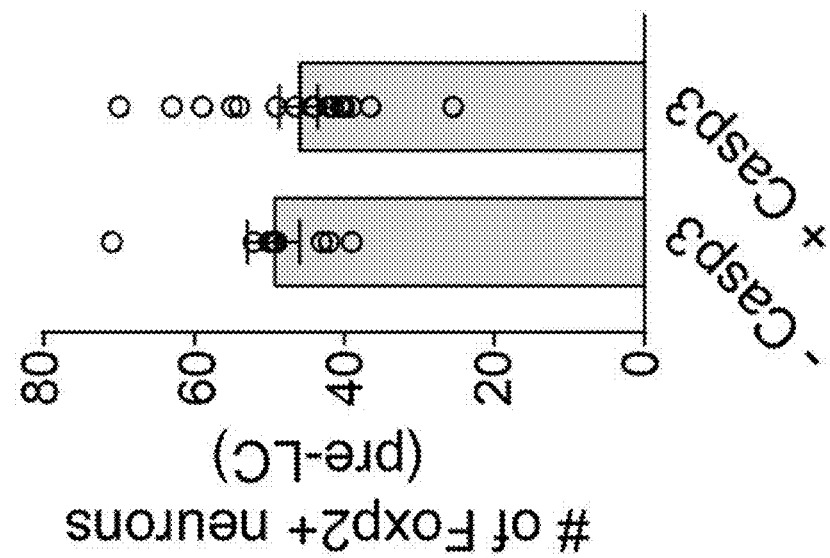
Figure 11C:
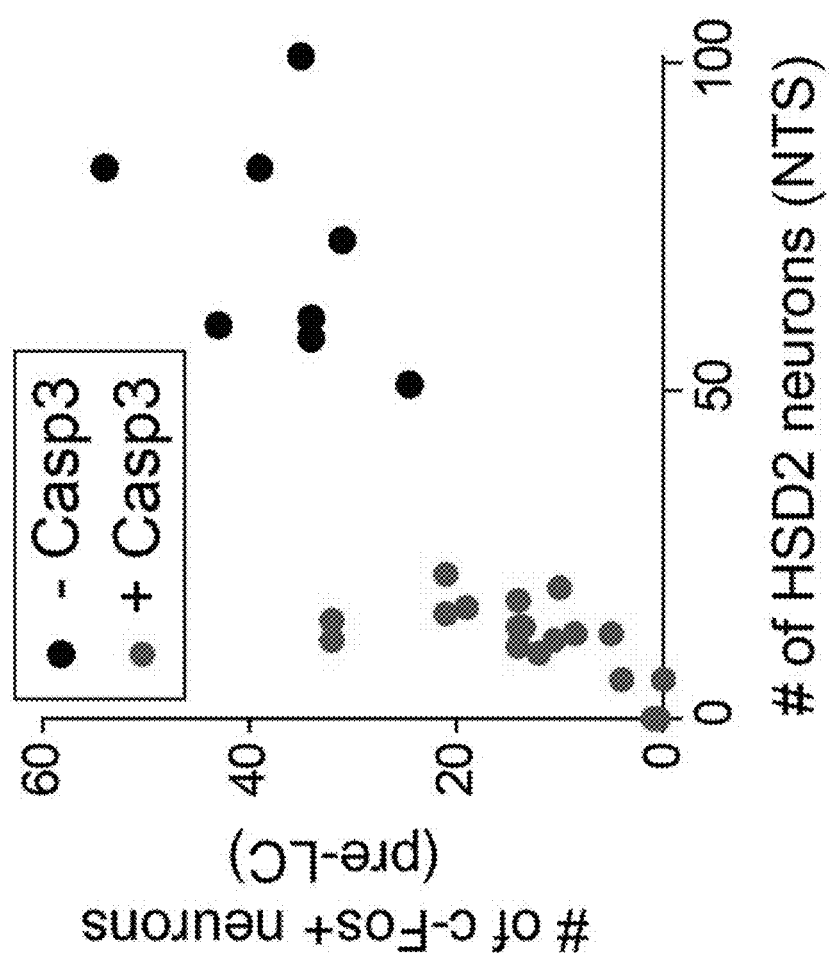

FIGS. 11A-D. Functional analysis of the NTS$^{HSD2}$→pre-LC$^{PDYN}$ connections. FIG. 11A: Functional validation of PDYN-GFP transgenic animals. Similar to PDYN-Cre line, GFP-positive neurons in the pre-LC mice were activated by sodium-depletion in PDYN-GFP mice (One out of 2 mice). FIG. 11B: A diagram of optogenetic stimulation of HSD2 neurons. Foxp2-positive pre-LC neurons express c-Fos after HSD2 stimulation (n=6 hemispheres from 3 mice). FIG. 11C: Relationship between the number of HSD2 neurons in the NTS and c-Fos-positive neurons in the pre-LC.>95% of c-Fos-positive neurons expressed Foxp2. FIG. 11D: Number of Foxp2-positive neurons was not affected by the ablation of HSD2 neurons (n=18 hemispheres from 9 mice for +Casp3, and n=8 hemispheres from 4 mice for −Casp3). Scale bar, 50 µm. **$P<0.01$ by two-tailed Wilcoxon test. Data presented as mean±s.e.m.

Figure 12A:
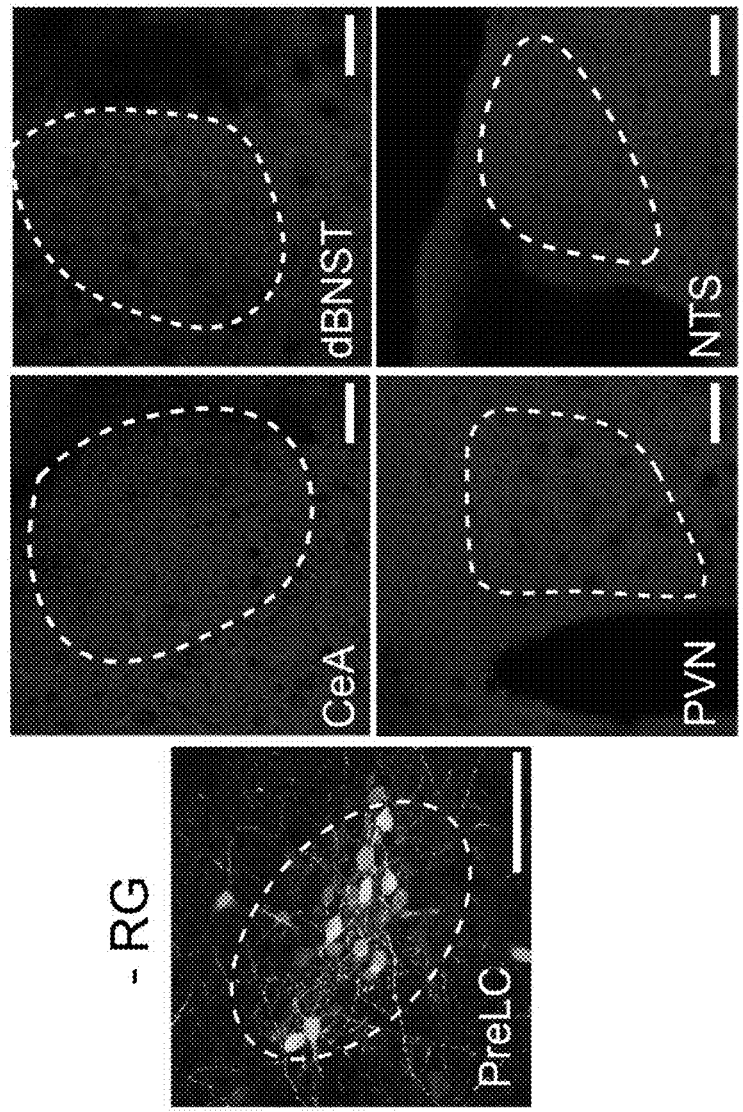
Figure 12C:
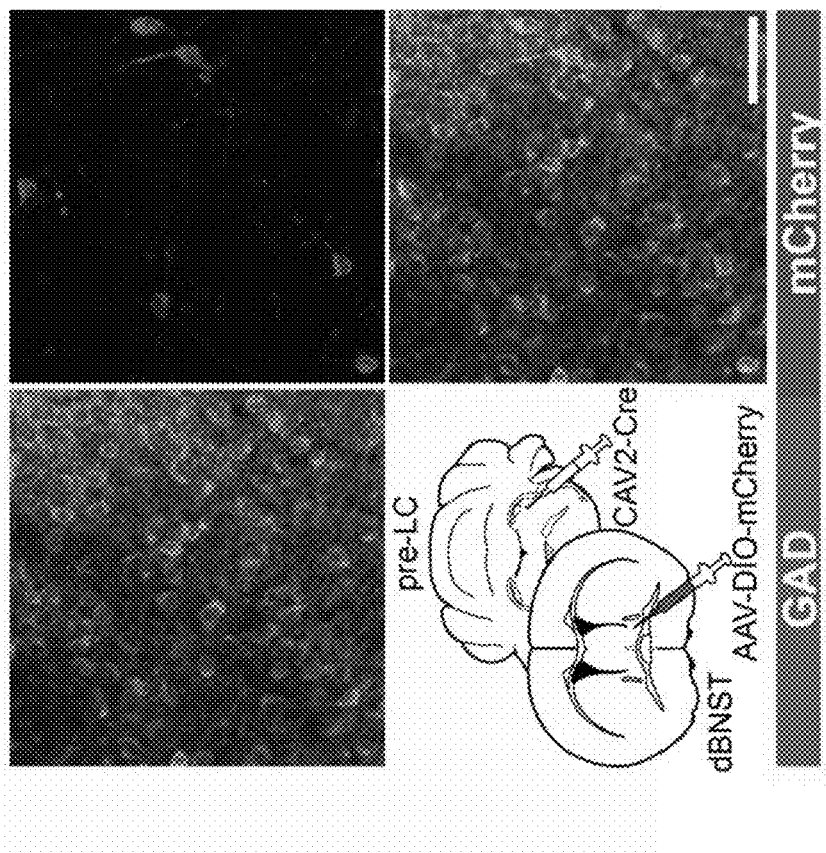
Figure 12B:
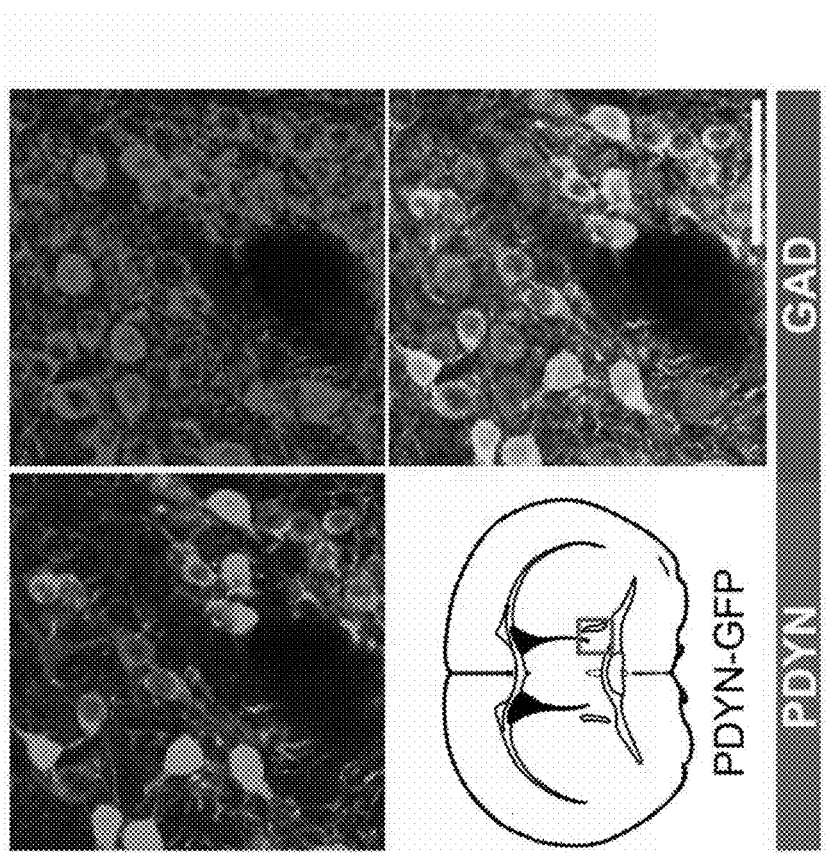

FIGS. 12A-C. Histological analysis of putative upstream brain structures of pre-LC$^{PDYN}$ neurons. FIG. 12A: Control mono synaptic tracing experiments without RG (One out of 3 mice). Scale bar, 100 µm. FIG. 12B: A majority of PDYN neurons in the dBNST (green) are inhibitory neurons (red, 77.3±1.7%, n=3 mice). FIG. 12C: CAV-2 positive neurons in the dBNST retrogradely labeled from the pre-LC (red) were inhibitory neurons (One out of 3 mice). Scale bar, 50 µm. The mouse brain in this figure has been reproduced from the mouse brain atlas.

Figure 13A:
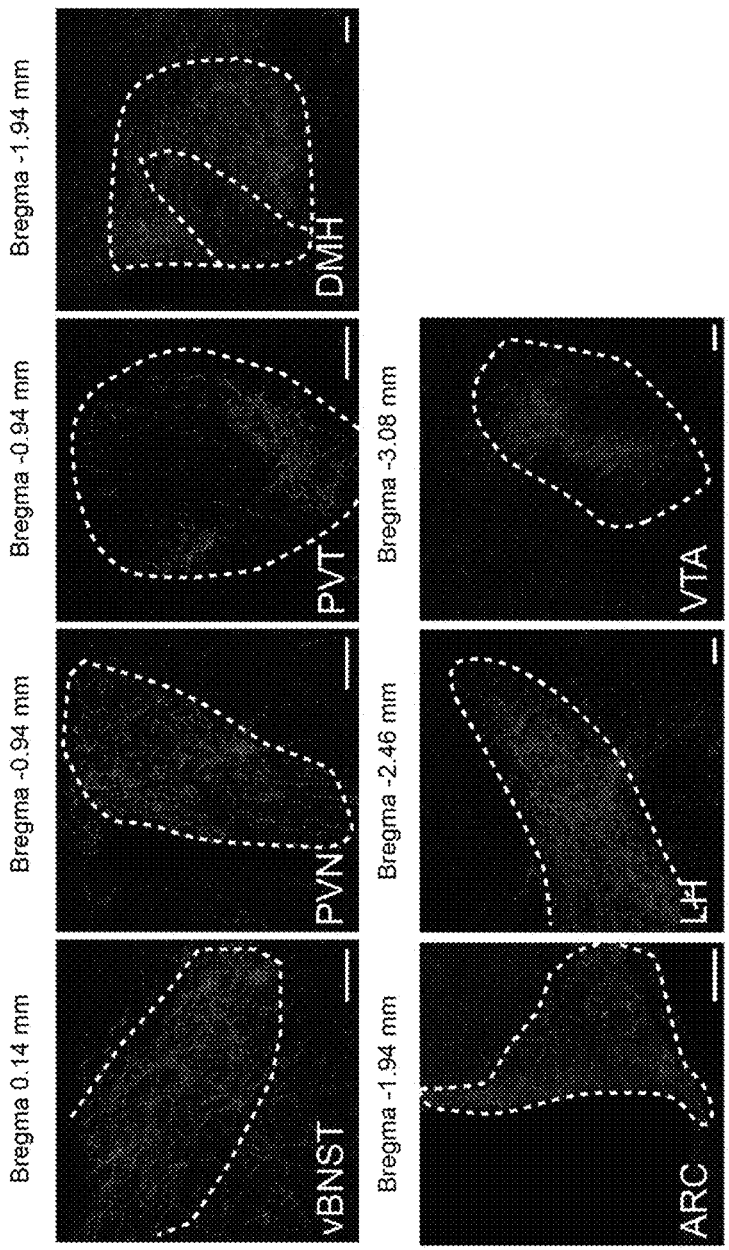
Figure 13A:
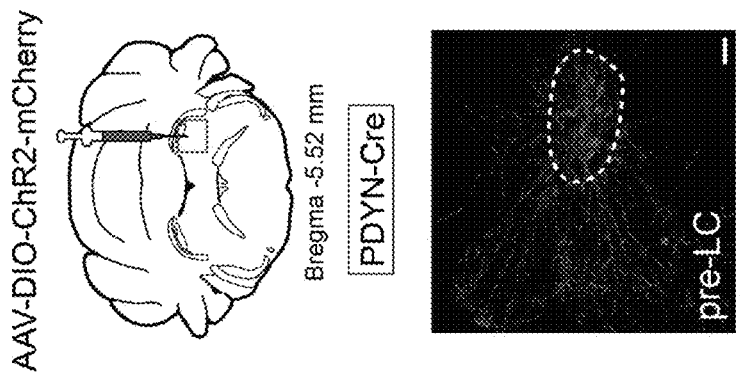
Figure 13B:
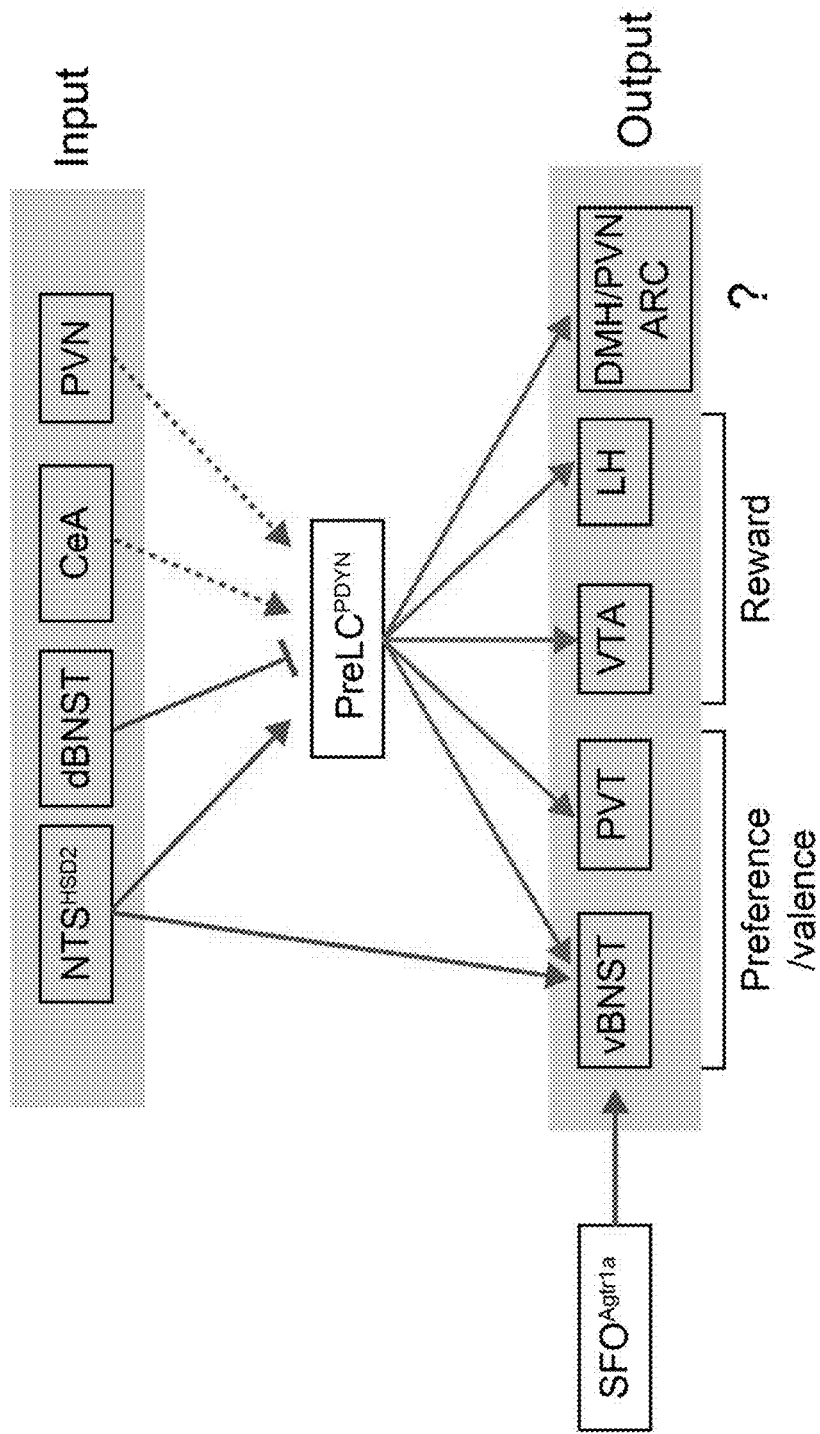

FIGS. 13A-B. Downstream projections of pre-LC$^{PDYN}$ neurons. FIG. 13A: PDYN-Cre mice were injected with AAV-DIO-ChR2-mCherry into the pre-LC. Representative axonal projections are shown (one out of six mice). Arc, arcuate nucleus; vBNST, ventral bed nucleus of the stria terminalis; DMH, dorsomedial hypothalamic nucleus; LH, lateral hypothalamus; PVN, paraventricular hypothalamic nucleus; PVT, paraventricular thalamic nucleus; VTA, ventral tegmental area. Scale bar, 50 µm. FIG. 13B: A wiring diagram of upstream and downstream neural connections of pre-LC$^{PDYN}$ neurons. It is feasible that the VTA and LH process the reward aspect of sodium appetite, while BNST and PVT may regulate preference and valence toward sodium. Besides the hindbrain, the BNST also receive interoceptive information from SFO neurons that express angiotensin receptor.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and make part of this disclosure.

As described herein, prodynorphin (PDYN)-positive neurons in the pre-locus coeruleus (referred to herein as "pre-$LC^{PDYN}$ neurons") selectively control sodium intake and play a critical role in sodium intake. The present disclosure provides methods and compositions for modulating (e.g., reducing or increasing) sodium appetite in subjects in need thereof, as well as identification of modulators for sodium appetite and/or intake.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Springs Harbor Press (Cold Springs Harbor, N Y 1989). For purposes of the present disclosure, the following terms are defined below.

As used herein, the term "neurons" is used to refer to cells found in the nervous system that are specialized to receive, process, and transmit information as nerve signals. Neurons can include a central cell body or soma, and two types of projections: dendrites, by which, in general, the majority of neuronal signals are conveyed to the cell body; and axons, by which, in general, the majority of neuronal signals are conveyed from the cell body to effector cells, such as target neurons or muscle. Neurons can convey information from tissues and organs into the central nervous system (afferent or sensory neurons) and transmit signals from the central nervous systems to effector cells (efferent or motor neurons). Examples of neurons include, but are not limited to, prodynorphin (PDYN)-positive neurons (e.g., the prodynorphin (PDYN)-positive neurons in the pre-locus coeruleus ("pre-$LC^{PDYN}$ neurons" as described herein), HSD2 neurons (e.g., HSD2 neurons in the nucleus of solitary tract ("$NTS^{HSD2}$ neurons") as described herein), GABAergic neurons (e.g., GABAergic neurons in the bed nucleus of the stria terminalis (BNST), central amygdala, or both).

As used herein, the term "modulating" a neuron refers to modulating the activity of a neuron. Modulating a neuron can be, for example, inhibiting the neuron or stimulating the neuron. The neuron can be, for example, photosensitive. In some embodiments, the neuron can be inhibited by electromagnetic radiation (e.g., light). In some embodiments, the neuron can be stimulated by electromagnetic radiation (e.g., light). The methods and compositions disclosed herein can be used to modulate the activity of a neuron for a selected duration, for example, 1 minute, 2 minutes, 3 minutes, 4 minutes, 5 minutes, 10 minutes, 20 minutes, 30 minutes, 40 minutes, 50 minutes, 100 minutes, 150 minutes, 200 minutes, or a range between any two of these values, or more. In some embodiments, the neuron is modulated (inhibited or stimulated) throughout the selected duration. In some embodiments, the neuron is modulated (inhibited or stimulated) with intervals of non-modulating break during the selected duration.

As used herein, the term "inhibiting" a neuron (for example, a prodynorphin (PDYN)-positive neuron as described herein (including pre-$LC^{PDYN}$ neuron) has its customary and ordinary meaning as would be understood by one of skill in the art in view of the present disclosure. It refers to reducing the likelihood of, delaying the onset of, and/or preventing depolarization of the cell membrane of the neuron (which may also be referred to as the plasma membrane), and thus, reducing the likelihood of, delaying the onset of, and/or preventing the neuron from generating an action potential or firing. In some embodiments, an inhibited neuron may not induce an action potential or fire. For example, a neuron can be inhibited by inducing a net efflux of cations from the cytosol and/or by inhibiting, reducing the likelihood of, or preventing a net influx of cations into the cytosol. For example, a neuron can be inhibited by inducing, increasing the likelihood of, or stimulating a net influx of anions into the cytosol. In some embodiments, a net efflux of cations comprises cations leaving the cytosol through a channel or pump in the plasma membrane or the endoplasmic reticulum (ER). In some embodiments, a net influx of anions comprises anions entering the cytosol across the plasma membrane. Non-limiting examples of cations include protons ($H^+$), potassium ($K^+$), calcium ($Ca^{2+}$), and any combination thereof. A non-limiting example of anion is chloride ($Cl^-$). The level by which a neuron is inhibited can vary, depending on, for example, the inhibition mechanism. For example, a neuron can be inhibited when the likelihood of an action potential (compared to an untreated or unaltered neuron over a specified period of time, for example, 0.01, 0.1, 1, or 10 seconds) is reduced by at least, or by at least about, 50%, 60%, 70%, 80%, 85%, 90%, 95%, 99%, 99.5%, 99.9%, or more. In some embodiments, inhibiting a neuron silences that neuron.

As used herein, the terms "decrease," "reduce," "reduced," "reduction," "decrease," and "inhibit" are used generally to refer to a decrease by an amount relative to a reference. The decreased amount relative to the reference can be, for example, a decrease by, by about, by at least, or by at least about, 20%, 25%, 30%, 35%, 40%, 45%, 50%, 55%, 60%, 65%, 70%, 75%, 80%, 85%, 90%, 95%, 98%, 99%, or a range between any two of these values, as compared to the reference.

As used herein, the terms "increase," "stimulate," "enhance" and "activate" are used to generally refer to an increase by an amount relative to a reference. The increased amount relative to the reference can be, for example, an increase by, by about, by at least, or by at least about, 20%, 25%, 30%, 35%, 40%, 45%, 50%, 55%, 60%, 65%, 70%, 75%, 80%, 85%, 90%, 95%, 98%, 99%, or a range between any two of these values, as compared to the reference. In some embodiment, the increase is, or is about, or is at least, or is at least about, a 2-fold, or at least about a 3-fold, or at least about a 4-fold, or at least about a 5-fold or at least about a 10-fold increase, or any increase between 2-fold and 10-fold or greater as compared to the reference.

As used herein, "stimulating" a neuron (e.g., a pre-$LC^{PDYN}$ neuron) has its customary and ordinary meaning as would be understood by one of skill in the art in view of the present disclosure. It refers to increasing the likelihood of, expediting the onset of, and/or inducing depolarization of the cell membrane of the neuron, and thus, increasing the likelihood of, expediting the onset of, and/or inducing an action potential in the neuron. For example, a neuron can be stimulated by a net efflux of anions from the cytosol, and/or a net influx of cations to the cytosol. In some embodiments, a stimulated neuron can be depolarized, inducing an action potential or firing of the neuron. Depolarization can be the result of a net influx of cations into the cytosol of the neuron. Cations can enter the cytosol though a channel in the plasma membrane and/or ER. The cations may comprise protons ($H^+$), sodium (Nat) ions, calcium ($Ca^{2+}$) ions, or a combination thereof. The level by which a neuron is stimulated can vary, depending on, for example, the stimulation mechanism. For example, a neuron can be stimulated when the likelihood of an action potential (compared to an unaltered neuron over a specified period of time, for example 0.01, 0.1, or 1 second) is increased by at least 50%, 60%, 70%, 80%, 85%, 90%, 95%, 99%, 99.5%, 99.9%, or more. In some embodiments, stimulating a neuron activates that neuron.

As used herein, the term "vector," can refer to a vehicle for carrying or transferring a nucleic acid. Non-limiting examples of vectors include viral vectors (for example, adenovirus vectors, adeno-associated virus (AAV) vectors, retrovirus vectors, lentiviral vectors, herpes virus vectors, phages, and proxvirus vectors); non-viral vectors such as liposomes, naked DNA, plasmids, cosmids; and the like. The term "AAV" or "adeno-associated virus" refers to a Dependoparvovirus within the Parvoviridae genus of viruses.

As used herein, the term "construct," refers to a recombinant nucleic acid that has been generated for the purpose of the expression of a specific nucleotide sequence(s), or that is to be used in the construction of other recombinant nucleotide sequences.

As used herein, the term "plasmid" refers to a nucleic acid that can be used to replicate recombinant DNA sequences within a host organism. The sequence can be a double stranded DNA.

As used herein, the terms "nucleic acid" and "polynucleotide" are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages. The terms "nucleic acid" and "polynucleotide" also specifically include nucleic acids composed of bases other than the five biologically occurring bases (adenine, guanine, thymine, cytosine and uracil). Unless specified otherwise, the left-hand end of any single-stranded polynucleotide sequence discussed herein is the 5' end; the left-hand direction of double-stranded polynucleotide sequences is referred to as the 5' direction.

As used herein, the term "subject" refers to an animal that is the object of treatment, observation or experiment. "Animal" includes cold- and warm-blooded vertebrates (e.g., mammals) and invertebrates (e.g., fish, shellfish and reptiles). "Mammal," as used herein, refers to an individual belonging to the class Mammalia and includes, but not limited to, humans, domestic and farm animals, zoo animals, sports and pet animals. Non-limiting examples of mammals include mice; rats; rabbits; guinea pigs; dogs; cats; sheep; goats; cows; horses; primates, such as monkeys, chimpanzees, apes, and humans. In some embodiments, the subject is a human. However, in some embodiments, the subject is not a human.

As used herein, the term "agonist" refers to any molecule or compound that fully or partially activates, stimulates, enhances, or promotes one or more of the biological properties of a biological entity, for example a protein, a nucleic acid, a cell (e.g., a neuron), an organ, or an organism. Agonists can include, but are not limited to, small organic and inorganic molecules, nucleic acids, peptides, peptide mimetics and antibodies.

As used herein, the term "effective amount" refers to an amount sufficient to effect beneficial or desirable biological and/or clinical results. For example, an "effective amount" of a modulator of sodium appetite is an amount of the modulator, alone or in combination with one or more other therapies and/or agents, sufficient to cause an alteration in the sodium appetite of a subject in need thereof.

"Pharmaceutically acceptable" carriers are ones which are nontoxic to the cell or mammal being exposed thereto at the dosages and concentrations employed. "Pharmaceutically acceptable" carriers can be, but not limited to, organic or inorganic, solid or liquid excipients which is suitable for the selected mode of application such as oral application or injection, and administered in the form of a conventional pharmaceutical preparation, such as solid such as tablets, granules, powders, capsules, and liquid such as solution, emulsion, suspension and the like. The physiologically acceptable carrier can be an aqueous pH buffered solution such as phosphate buffer or citrate buffer, and can also comprise one or more of the following: antioxidants including ascorbic acid, low molecular weight (less than about 10 residues) polypeptides, proteins, such as serum albumin, gelatin, immunoglobulins; hydrophilic polymers such as polyvinylpyrrolidone, amino acids, carbohydrates including glucose, mannose, or dextrins, chelating agents such as EDTA, sugar alcohols such as mannitol or sorbitol, salt-forming counterions such as sodium, and nonionic surfactants such as Tween™, polyethylene glycol (PEG), and Pluronics™. Auxiliary, stabilizer, emulsifier, lubricant, binder, pH adjustor controller, isotonic agent and other conventional additives may also be added to the carriers.

Sodium Intake and Appetite

Sodium is the main cation in the extracellular fluid that regulates various physiological functions. Multiple brain sites including the hypothalamus, amygdala, and hindbrain regulate sodium consumption. For example, sodium-depletion stimulates neurons in the lamina terminalis (LT) and hydroxysteroid dehydrogenase (HSD2)-expressing neurons in the nucleus of solitary tract (NTS) through a combinatorial action of angiotensin II or/and aldosterone, two major hormones that regulate body fluid balance. Recent neural manipulation studies described the contribution of LT and HSD2 neurons to sodium intake. In those studies, however, sodium appetite was only observed under water-deprived conditions or with additional signaling, representing complex regulatory mechanisms of the appetite.

As described herein, a subset of excitatory neurons in the pre-locus coeruleus (pre-LC) that express prodynorphin (PDYN) serve as a critical neural substrate for sodium intake behavior. These PDYN-positive neurons are referred herein as "pre-$LC^{PDYN}$ neurons." Sodium intake and appetite can be inhibited or stimulated by modulating pre-$LC^{PDYN}$ neurons. For example, acute stimulation of pre-$LC^{PDYN}$ neurons triggered robust sodium ingestion even from rock salt by transmitting negative valence signals (see Example 1), and inhibition of pre-LC$^{PDYN}$ neurons selectively reduced sodium consumption (see Examples 1 and 2). Also demonstrated herein include that peripheral chemosensory signals rapidly suppressed these sodium appetite neurons (see Example 2). Simultaneous in vivo optical recording and gastric infusion revealed that sensory detection of sodium, but not sodium ingestion per se, is required for the acute modulation of pre-LC PDYN neurons and satiety of sodium appetite (see Examples 1-2). For example, inhibiting pre-LC$^{PDYN}$ neurons can reduce sodium appetite in a subject. As another example, stimulating pre-LC$^{PDYN}$ neurons can enhance sodium appetite in the subject. In some embodiments described herein, optogenetic and/or chemogenetic activation of pre-LC$^{PDYN}$ neurons selectively enhance sodium appetite. In some embodiments, optogenetic and/or chemogenetic inhibition of pre-LC$^{PDYN}$ neurons selectively reduce sodium appetite.

Reducing sodium appetite and/or intake, in some embodiments, comprises inhibiting a plurality of (or a population of) PDYN-positive neurons such as pre-LC$^{PDYN}$ neurons (for example, by inhibiting depolarization of the cell membrane of pre-LC$^{PDYN}$ neurons). In accordance with methods and compositions of some embodiments stimulating sodium appetite and/or intake comprises inhibiting excitatory neurons of the pre-locus coeruleus (pre-LC) such as pre-LC$^{P}$$_{DYN}$ neurons (for example, by inhibiting depolarization of the cell membrane of pre-LC$^{PDYN}$ neurons), or inhibiting neurons in the nucleus of solitary tract (NST) such as HSD2 neurons in NST (referred to herein as "NTS$^{HSD2}$ neurons") (for example by inhibiting depolarization of the cell membrane of NTS$^{HSD2}$ neurons), or both. The inhibition of any of the neurons described herein can comprise inhibiting depolarization of the neuron, a net influx of cations into the cytosol (such as transmembrane migration of sodium cations into the cytosol and/or a release of calcium ions from an endoplasmic reticulum into the cytosol). In some embodiments, a plurality of neurons that is inhibited can comprise, for example, at least 10, $10^2$, $10^3$, $10^4$, $10^5$, $10^6$, $10^7$, $10^7$, and a range between any two of the values, neurons.

Stimulating sodium appetite and/or intake, in some embodiments, comprises stimulating PDYN-positive neurons such as pre-LC$^{PDYN}$ neurons (for example, by stimulating depolarization of the cell membrane of pre-LC$^{PDYN}$ neurons). In accordance with methods and compositions of some embodiments stimulating sodium appetite and/or intake comprises stimulating an excitatory neuron of the pre-locus coeruleus (pre-LC) such as pre-LC$^{PDYN}$ neurons (for example, by stimulating depolarization of the cell membrane of pre-LC$^{PDYN}$ neurons). The stimulation of any of the neurons described herein can comprise depolarization of the neuron, a net influx of cations into the cytosol (such as transmembrane migration of sodium cations into the cytosol, and/or a release of calcium ions from an endoplasmic reticulum into the cytosol). In some embodiments, a plurality of neurons that is stimulated can comprise, for example, at least 10, $10^2$, $10^3$, $10^4$, $10^5$, $10^6$, $10^7$, $10^8$, or a range between any two of the listed values, neurons.

The subjects that the methods and compositions described herein are applicable include, but are not limited to, human subjects and non-human subjects (e.g., non-human mammals). The age and gender of the subject can vary. For example, the subject can an elderly subject, a juvenile, an infant, or an adult. As used herein, an "elderly" subject refers to a human that is at least 50 years old, for example at least 55, 60, 65, 70, 75, 80, 85, 90, or a range between any two of these values, years old. The subject can be, or be about, one-day old, one-month old, six-month old, one-year old, two-year old, five-year old, ten-year old, twenty-year old, thirty-year old, forty-year old, fifty-year old, or a range between any two of these values. Subjects that are in need of the methods and compositions described herein for reducing sodium intake include a subject suffering from, or is at a risk of developing, a kidney disorder, kidney damage, a cardiovascular disease, high blood pressure, overweight, edema, left ventricular hypertrophy, stroke, or a combination thereof. The kidney disorder can be, for example, a chronic kidney disease or kidney failure. It is contemplated that a subject is at a risk of developing heart- and kidney-related diseases can benefit from reducing sodium appetite and/or intake. It is also contemplated that a subject suffering from heart- and kidney-related diseases can benefit from reducing sodium appetite and/or intake. By way of example, in some embodiments, sodium appetite and/or intake in a subject can be reduced compared to the sodium appetite and/or intake of the subject before application of the methods/compositions described herein for reducing sodium appetite and/or intake. In some embodiments, sodium intake in a subject can be reduced to a level of sodium intake recommended as healthy for the subject. In some embodiments, a subject is at a risk of developing high blood pressure or is suffering from high blood pressure. In some embodiments, the subject is at a risk of developing a cardiovascular disease or is suffering from a cardiovascular disease.

Conditional Ion Modulators

As used herein, "conditional ion modulators" refers to chemogenetic receptors and optogenetic actuators. In some embodiments, the conditional ion modulator comprises, or is, a chemogenetic receptor. In some embodiments, the conditional ion modulator comprises, or is, an optogenetic actuator. A "conditional ion modulator nucleic acid" is used herein to refer to a nucleic acid that encodes a conditional ion modulator (e.g., an optogenetic receptor or chemogenetic receptor).

Chemogenetic receptor can be used in the methods and compositions disclosed herein to modulate (e.g., inhibit or enhance) sodium intake and/or appetite, and the methods and compositions disclosed herein for identifying modulators for sodium intake and/or appetite. As used herein, "chemogenetic receptor" refers to a receptor that can be expressed in a cell and modulates movement of ions in or out of the cell when a condition is present, for example binding of an agonist such as a small molecule such as clozapine N-oxide (CNO). For example, the chemogenetic receptor can comprise a G protein coupled receptor and can conditionally induce signaling in the cell that expresses the receptor. Examples of chemogenetic receptors include, but are not limited to, Designer Receptors Exclusively Activated by Designer Drugs (DREADDs). In some embodiment, the DREADD may encode a receptor such as a G protein coupled receptor configured to depolarize or activate a neuron (e.g., a LC$^{PDYN}$ neuron or an NTS$^{HSD2}$ neuron) Non-limiting exemplary chemogenetic receptors are describe in Roth (2016), "DREADDs for Neuroscientists" Neuron. 89: 683-694, which is incorporated by reference in its entirety herein. In some embodiments, the chemogenetic receptor comprise an ion channel or ion pump, or be in signal transduction communication with an ion channel or ion pump. As used herein, a "chemogenetic receptor nucleic acid" refers to a nucleic acid that encodes a chemogenetic receptor. In some embodiments, the optogenetic actuator comprises or is hM3DREADD or hM4Di. hM3DREADD comprises a modified human M3 muscarinic receptor and is activated by the agonist CNO. The CNO can be administered to a subject, for example systemically or directly to the CNS, and can thus bind to the chemogenetic receptor (such as hM3DREADD). Binding of CNO to hM3DREADD induces Gq G-protein coupled signaling, which induces the release of intracellular calcium in neurons, enhancing neuron activation. CNO can be administered to a subject nasally, transcranially, intracranially, orally, intravenously, subcutaneously, transdermally, intreperitoneally, nasally, or any combination thereof.

Optogenetic actuator can be used in the methods and compositions disclosed herein to modulate (e.g., inhibit or enhance) sodium intake and/or appetite, and the methods and compositions disclosed herein for identifying modulators for sodium intake and/or appetite. As used herein, "optogenetic actuator" refers to an ion transporter that can be expressed in a cell, and directly or indirectly transport ions (into or out of the cytosol) when a condition is present, for example upon stimulation with electromagnetic radiation. An optogenetic actuator can comprise, or can be, a passive transporter (such as an ion channel) and/or an active transporter (such as an ion pump). For example, the optogenetic actuator can comprise an ion channel or an ion pump, and can conditionally permit or prevent the passage of ions through the ion channel. In some embodiments, the optogenetic actuator comprises, or is, a channelrhodopsin, halorhodopsin and/or archaeorhodopsin. Non-limiting exemplary optogenetic actuators are described in Lin (2011) "A User's Guide to Channelrhodopsin Variants: Features, Limitations and Future Developments" Exp. Physiol. 96: 19-25, which is incorporated by reference in its entirety herein. As used herein, an "optogenetic actuator nucleic acid" refers to a nucleic acid that encodes an optogenetic actuator.

In some embodiments, the conditional ion modulator comprises an optogenetic actuator such as a channelrhodopsin (e.g., ChR2 or VChR1). Channelrhodopsin comprises an ion channel, the opening of which is stimulated by electromagnetic radiation of a suitable wavelength. For example, ChR2 is stimulated by light in the blue spectrum (e.g., about 450 nm to about 470 nm) and VChR1 is stimulated by light in the green spectrum (e.g., about 550 nm to about 570 nm). In some embodiments of the methods and compositions disclosed herein, the conditional ion modulator comprises an optogenetic receptor, and is stimulated by electromagnetic radiation, thus inducing opening of an ion channel and a change in polarity of the neuron that expresses the conditional ion modulator.

In some embodiments, the conditional ion modulator is configured to inhibit stimulation of a neuron or inhibit a neuron, for example by inducing a net efflux of cations from a cytosol and/or induce a net influx of anions to the cytosol. Such conditional ion modulators are referred to herein as "inhibitory conditional ion modulators." Non-limiting examples of inhibitory conditional ion modulators include hM4Di, halorhodopsin, and archaeorhodopsin. hM4Di receptors can inhibit neurons upon stimulation with their agonist, for example CNO. The hM4Di receptor comprises a modified form of the human M4 muscarinic (hM4) receptor. The hM4Di receptor can be activated by CNO, engaging the Gi signaling pathway. Gi signaling in neurons results in the opening of potassium channels and an influx of potassium ions, decreasing the capacity of the neuron to depolarize. Neurons expressing hM4Di that are treated with CNO can have decreased firing rates. Halorhodopsin comprises a transmembrane chloride channel, which can move chloride channels into the cell in response to electromagnetic radiation in the green to yellow spectrum of visible light. Archaeorhodopsin comprises a transmembrane proton pump, which can pump proteins out of the cell in response to light, thereby hyperpolarizing the neuron, and inhibiting an action potential by the neuron. In some embodiments of the methods and compositions disclosed herein, a conditional ion modulator inhibits a neuron (e.g., a $LC^{PDYN}$ neuron or an $NTS^{HSD2}$ neuron).

In some embodiments, the conditional ion modulator is configured to stimulate a neuron, for example by inducing a net influx of cations into a cytosol and/or induce a net efflux of anions from the cytosol. Such conditional ion modulators are referred to herein as "stimulatory conditional ion modulators." Examples or such stimulatory conditional ion modulators include hM3DREADD and/or channelrhodopsin. In some embodiments, for example methods and compositions in which a conditional ion modulator inhibits a neuron, the conditional ion modulator comprises hM3DREADD and/or channelrhodopsin.

Compositions for Nucleic Acid Delivery to a Subject and Methods of Administration Various systems and methods are known in the art for delivering nucleic acid molecules into a cell, a tissue, an organ, and/or a subject. The delivery can be, for example, target-specific, tissue-specific, cell type specific, organ specific, nonspecific, and/or systematic. In some embodiments, the nucleic acid molecule comprises a coding sequence for one or more proteins, and the delivery is used for expressing the one or more proteins encoded by the nucleic acid molecule in the target cell, tissue, organ, and/or subject.

Disclosed include nucleic acids (e.g., an expression vector) in a composition (e.g., a pharmaceutical composition). The nucleic acids can, for example, comprise a coding sequence for a stimulatory conditional ion modulator, wherein the stimulatory conditional ion modulator is expressed and/or activated in response to a stimulus or agonist. In some embodiments, activation of the stimulatory conditional ion modulator can inhibit (e.g., specifically and/or selectively inhibit) a neuron population, for example pre-$LC^{PDYN}$ neurons. As another example, the nucleic acids can comprise a coding sequence for an inhibitory conditional ion modulator, wherein the inhibitory conditional ion modulator is expressed and/or activated in response to a stimulus or agonist. In some embodiments, expression of the inhibitory conditional ion modulator can stimulate (e.g., specifically and/or selectively stimulate) a neuron population, for example pre-$LC^{PDYN}$ neurons.

Many different viral and non-viral vectors and methods of their delivery, for use in gene delivery (including gene therapy), are known, including adenovirus vectors, adeno-associated virus (AAV) vectors, retrovirus vectors, lentiviral vectors, herpes virus vectors, liposomes, proxviruses, naked DNA administration, plasmids, cosmids, phages, encapsulated cell technology, and the like. A detailed review of possible techniques for transforming genes into desired cells of the eye is taught by Wright (Br J Ophthalmol, 1997; 81: 620-622). The vectors (e.g., an AAV vector) can be used to deliver the coding sequence for the stimulatory conditional ion modulator or the inhibitory conditional ion modulator to a subject in need thereof. The expression of the stimulatory conditional ion modulator or the inhibitory conditional ion modulator from the nucleic acid (e.g., the expression vector) can be controlled by a transcription regulatory element, for example for example, a cell specific promoter to allow expression occurred only in a specific cell type (e.g., neurons), or a promoter selected from Human elongation factor-1 alpha (EF-1 alpha), Human cytomegalovirus promoter (CMV), and CAG promoter. Titers of the viral vector to be administered will vary depending, for example, on the particular viral vector, the mode of administration, the treatment goal, the individual, and the cell type(s) being targeted, and can be determined by methods standard in the art.

Adeno-associated virus (AAV) is a replication-deficient parvovirus, the single-stranded DNA genome of which is about 4.7 kb in length including 145 nucleotides inverted terminal repeat (ITRs). The ITRs play a role in integration of the AAV DNA into the host cell genome. When AAV infects a host cell, the viral genome integrates into the host's chromosome resulting in latent infection of the cell. In a natural system, a helper virus (for example, adenovirus or herpesvirus) provides genes that allow for production of AAV virus in the infected cell. In the case of adenovirus, genes E1A, E1B, E2A, E4 and VA provide helper functions. Upon infection with a helper virus, the AAV provirus is rescued and amplified, and both AAV and adenovirus are produced. In the instances of recombinant AAV vectors having no Rep and/or Cap genes, the AAV can be non-integrating.

AAV vectors that comprise coding sequences of the stimulatory conditional ion modulator or the inhibitory conditional ion modulator are provided. The AAV vector can include a 5' inverted terminal repeat (ITR) of AAV, a 3' AAV ITR, a promoter, and a restriction site downstream of the promoter to allow insertion of a polynucleotide encoding the stimulatory conditional ion modulator or the inhibitory conditional ion modulator, wherein the promoter and the restriction site are located downstream of the 5' AAV ITR and upstream of the 3' AAV ITR. In some embodiments, the AAV vector includes a posttranscriptional regulatory element downstream of the restriction site and upstream of the 3' AAV ITR.

Generation of the viral vector can be accomplished using any suitable genetic engineering techniques well known in the art, including, without limitation, the standard techniques of restriction endonuclease digestion, ligation, transformation, plasmid purification, and DNA sequencing, for example as described in Sambrook et al. (Molecular Cloning: A Laboratory Manual. Cold Spring Harbor Laboratory Press, N.Y. (1989)). The viral vector can incorporate sequences from the genome of any known organism. The sequences can be incorporated in their native form or can be modified in any way to obtain a desired activity. For example, the sequences can comprise insertions, deletions or substitutions.

In some embodiments, the viral vectors can include additional sequences that make the vectors suitable for replication and integration in eukaryotes. In some embodiments, the viral vectors disclosed herein can include a shuttle element that makes the vectors suitable for replication and integration in both prokaryotes and eukaryotes. In some embodiments, the viral vectors can include additional transcription and translation initiation sequences, such as promoters and enhancers; and additional transcription and translation terminators, such as polyadenylation signals. Various regulatory elements that can be included in an AAV vector have been described in detail in US2012/0232133 which is hereby incorporated by reference in its entirety.

The pharmaceutical composition can comprise one or more nucleic acids disclosed herein and one or more pharmaceutically acceptable carriers. The composition can also comprise additional ingredients such as diluents, stabilizers, excipients, and adjuvants. As used herein, "pharmaceutically acceptable" carriers, excipients, diluents, adjuvants, or stabilizers are the ones nontoxic to the cell or subject being exposed thereto (preferably inert) at the dosages and concentrations employed or that have an acceptable level of toxicity as determined by the skilled practitioners.

The carriers, diluents and adjuvants can include buffers such as phosphate, citrate, or other organic acids; antioxidants such as ascorbic acid; low molecular weight polypeptides (e.g., less than about 10 residues); proteins such as serum albumin, gelatin or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, Pluronics™ or polyethylene glycol (PEG). In some embodiments, the physiologically acceptable carrier is an aqueous pH buffered solution.

As will be readily apparent to one of skill in the art, the useful in vivo dosage of the recombinant virus to be administered and the particular mode of administration will vary depending upon the age, weight, the severity of the affliction, and animal species treated, the particular recombinant virus expressing the protein of interest that is used, and the specific use for which the recombinant virus is employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

Although the exact dosage will be determined on a drug-by-drug basis, in most cases, some generalizations regarding the dosage can be made. In some embodiments, the viral vector for delivery a nucleic acid to a subject (e.g., systematic delivery, or delivery to the brain tissue of the subject) can be administered, for example via injection, to a subject at a dose of between $1 \times 10^{10}$ genome copies (GC) of the recombinant virus per kg of the subject and $2 \times 10^{14}$ GC per kg, for example between $5 \times 10^{11}$ GC/kg and $5 \times 10^{12}$ GC/kg. In some embodiments, the dose of the viral vector (e.g., AAV vectors) administered to the subject is no more than $2 \times 10^{14}$ GC per kg. In some embodiments, the dose of the viral vector administered to the subject is no more than $5 \times 10^{12}$ GC per kg. In some embodiments, the dose of the viral vector administered to the subject is no more than $5 \times 10^{11}$ GC per kg.

The nucleic acid molecule, for example, a vector (e.g., a viral vector)) comprising a coding sequence of a stimulatory conditional ion modulator or an inhibitory conditional ion modulator can be administered to a subject (e.g., a human) in need thereof. The route of the administration is not particularly limited. For example, a therapeutically effective amount of the nucleic acid molecule can be administered to the subject by via routes standard in the art. Non-limiting examples of the route include intravitreal, intravenous, intraocular, or subretinal administration (e.g., intravitreal, intravenous, intraocular, or subretinal injection), depending on the retinal layer being targeted. In some embodiments, the nucleic acid molecule is administered to the subject by systematic transduction. In some embodiments, the nucleic acid molecule is administered to the subject by intravenous injection. In some embodiments, the nucleic acid molecule is administered to the subject by subretinal injection. In some embodiments, the administration of the nucleic acid molecule targeting of retinal pigment epithelium—the most distal layer from the vitreal space. In some embodiments, the delivery of the nucleic acid molecule is targeted to retinal ganglion cells, bipolar cells, or both. The ganglion cells are, in some embodiments, accessible to intravitreal injection as disclosed herein. Intravitreal and/or subretinal injection can be used, in some embodiments to target the bipolar cells, for example in circumstances in which the photoreceptor cell layer is absent due to degeneration.

Actual administration of the expression vectors for the stimulatory conditional ion modulator or the inhibitory conditional ion modulator can be accomplished by using any physical method that will transport the vectors (e.g., viral vectors) into the target tissue(s) (e.g., brain) of the subject. In some embodiments, the vectors can be administered systematically, e.g., by intravenous injection. Pharmaceutical compositions can be prepared, for example, as injectable formulations. The recombinant virus to be used can be utilized in liquid or freeze-dried form (in combination with one or more suitable preservatives and/or protective agents to protect the virus during the freeze-drying process). For gene therapy (e.g., of neuronal and ocular disorders which may be ameliorated by a specific gene product) a therapeutically effective dose of the recombinant virus expressing the therapeutic protein is administered to a host in need of such treatment. The use of the recombinant virus disclosed herein in the manufacture of a medicament for inducing immunity in, or providing gene therapy to, a host is within the scope of the present application.

In instances where human dosages for the viral vector (e.g., AAV vector) have been established for at least some condition, those same dosages, or dosages that are between about 0.1% and 500%, more preferably between about 25% and 250% of the established human dosage can be used. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

A therapeutically effective amount of the expression vector (e.g., AAV vector) can be administered to a subject at various points of time. For example, the expression vector can be administered to the subject prior to, during, or after the subject has developed a disease or disorder. The expression vector can also be administered to the subject prior to, during, or after the occurrence of a disease or disorder (e.g., neuronal disorders, ocular disorders, or a combination thereof). In some embodiments, the expression vector is administered to the subject during remission of the disease or disorder. In some embodiments, the expression vector is administered prior to the onset of the disease or disorder in the subject. In some embodiments, the expression vector is administered to a subject at a risk of developing the disease or disorder.

The dosing frequency of the expression vector (e.g., viral vector) can vary. For example, the viral vector can be administered to the subject about once every week, about once every two weeks, about once every month, about one every six months, about once every year, about once every two years, about once every three years, about once every four years, about once every five years, about once every six years, about once every seven years, about once every eight years, about once every nine years, about once every ten years, or about once every fifteen years. In some embodiments, the viral vector is administered to the subject at most about once every week, at most about once every two weeks, at most about once every month, at most about one every six months, at most about once every year, at most about once every two years, at most about once every three years, at most about once every four years, at most about once every five years, at most about once every six years, at most about once every seven years, at most about once every eight years, at most about once every nine years, at most about once every ten years, or at most about once every fifteen years.

Methods of Reducing Sodium Intake and/or Appetite

In some embodiments, a method of reducing sodium intake and/or appetite in a subject in need thereof is described. The method can comprise, inhibiting a plurality of pre-$LC^{PDYN}$ neurons of the subject, thereby reducing sodium appetite in the subject. In some embodiments, the method comprises inhibiting depolarization of the cell membranes of the plurality pre-$LC^{PDYN}$ neurons. Thus, stimulation of the plurality of pre-$LC^{PDYN}$ neurons can be inhibited, thus inhibiting sodium intake and/or appetite in the subject. In some embodiments, the method comprises at least one of inhibiting cation influx into a cytosol of the plurality of pre-$LC^{PDYN}$ neurons, inducing anion influx into the cytosol of the plurality of pre-$LC^{PDYN}$ neurons, and inducing cation efflux from the cytosol of the plurality of pre-$LC^{PDYN}$ neurons. In some embodiments, the method comprises administering a vector encoding a conditional ion modulator to the subject as described herein.

The method comprises, in some embodiments, determining sodium intake and/or appetite in the subject before inhibiting the plurality of pre-$LC^{PDYN}$ neurons of the subject, determining sodium intake and/or appetite in the subject after inhibiting the plurality of pre-$LC^{PDYN}$ neurons of the subject, or both. The extent to which the sodium intake and/or appetite is reduced in the subject can vary. For example, the sodium intake and/or appetite of the subject is reduced by, by about, by at least, or by at least about, 10%, 20%, 30%, 40%, 50%, 60%, 70%, 80%, 90%, 95%, 98%, or a range between any two of these values, as compared to the sodium and/or appetite of the subject before application of the method. In some embodiments, reducing sodium appetite in the subject comprises reducing sodium ingestion for the subject. Some of the plurality of pre-$LC^{PDYN}$ neurons can express, for example, forkhead box protein P2 (FOXP2). For example, at least 10%, 20%, 30%, 40%, 50%, 60%, 70%, 80%, 90%, 95%, 98%, or a range of any two of these values, of the plurality of pre-$LC^{PDYN}$ neurons express FOXP2.

In some embodiments, inhibiting the plurality of pre-$LC^{PDYN}$ neurons of the subject comprises oral contact of sodium without sodium ingestion in the subject. In some embodiments, inhibiting the plurality of pre-$LC^{PDYN}$ neurons of the subject comprises stimulating a plurality of GABAergic neurons in the bed nucleus of the stria terminalis (BNST), central amygdala, or both of the subject. For example, the plurality of GABAergic neurons in BNST, central amygdala, or both of the subject can comprise PDYN-positive neurons. In some embodiments, inhibiting the plurality of pre-$LC^{PDYN}$ neurons of the subject comprises inhibiting a plurality of HSD2 neurons in the nucleus of solitary tract ($NTS^{HSD2}$ neurons) in the subject.

Various inhibition methods/techniques can be used to inhibit pre-$LC^{PDYN}$ neurons. For example, the inhibition can comprise optogenetic inhibition, chemogenetic inhibition, or both. In some embodiments, inhibiting the plurality of pre-$LC^{PDYN}$ neurons of the subject comprises inhibiting the plurality of pre-$LC^{PDYN}$ neurons by a stimulatory conditional ion modulator. For example, inhibiting the plurality of pre-LC$^{PDYN}$ neurons can comprise: administering a nucleic acid encoding a stimulatory conditional ion modulator to the subject, wherein the stimulatory conditional ion modulator is activated in response to a stimulus or agonist; and applying an agonist or stimulus of the stimulatory conditional ion modulator to the subject, causing the activation of the stimulatory conditional ion modulator, thereby inhibit the pre-LC$^{PDYN}$ neurons. In some embodiments, the stimulatory conditional ion modulator comprises a chloride conducting channelrhodopsin (ChloC), and the stimulus comprises an optical stimulus. the agonist is clozapine-N-oxide. In some embodiments, the nucleic acid is administered to the subject in an adeno-associated viral (AAV) vector.

The duration in which the plurality of pre-LC$^{PDYN}$ neurons is inhibited can vary. For example, a duration can be, 1 minute, 2 minutes, 3 minutes, 4 minutes, 5 minutes, 10 minutes, 20 minutes, 30 minutes, 40 minutes, 50 minutes, 100 minutes, 150 minutes, 200 minutes, or a range between any two of these values, or more. In some embodiments, the neuron is inhibited throughout the selected duration. In some embodiments, the neuron is inhibited with intervals of non-modulating break during the selected duration. In some embodiments, inhibiting the plurality of pre-LC$^{PDYN}$ neurons lasts for at least five minutes in total.

In some embodiments, the method comprises identifying the subject as in need of reducing sodium intake and/or appetite. For example, the subject can be identified as suffering from or at a risk of developing a kidney disorder, kidney damage, a cardiovascular disease, high blood pressure, overweight, edema, left ventricular hypertrophy, stroke, or a combination thereof. The subject, in some embodiments, is at the risk of developing, or is suffering from, a kidney disorder, kidney damage, a cardiovascular disease, high blood pressure, overweight, edema, left ventricular hypertrophy, stroke, or a combination thereof. In some embodiments, the subject is at the risk of developing, or is suffering from, a chronic kidney disease or kidney failure. In some embodiments, the subject is a human or a non-human mammal. In some embodiments, the subject is an elderly subject. In some embodiments, the method of reducing sodium intake and appetite is a method of ameliorating, inhibiting, delaying the onset of, reducing the severity of, or preventing a kidney disorder, kidney damage, a cardiovascular disease, high blood pressure, overweight, edema, left ventricular hypertrophy, stroke, or a combination thereof.

In some embodiments, the cations comprise protons, sodium cations, calcium cations, or a combination thereof. It will be appreciated that since the cytosol of a neuron (such as a pre-LC$^{PDYN}$ neuron) comprises cations, a net efflux of cations into the cytosol refers to a decrease in the quantity of cations in the cytosol compared to prior to the efflux. In some embodiments, the quantity of cations in the cytosol is decreased by at least 1%, for example at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 90%, 95%, 96%, 97%, 98%, 99%, or 99.9%, including ranges between any two of the listed values compared to prior to the efflux. In some embodiments, the net efflux of cations is effective to prevent an action potential in the neuron. In some embodiments, anions (such as those that exhibit a net influx into the cytosol of a neuron) comprise chloride anions (CO. Similarly, it will be appreciated that since the cytosol of a neuron (such as a pre-LC$^{PDYN}$ neuron) comprises anions, a net influx of anions from the cytosol refers to an increase in the quantity of anions in the cytosol compared to prior to the efflux. In some embodiments, the quantity of anions in the cytosol is increased by at least 1%, for example at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 90%, 95%, 100%, 150%, 200%, 300%, 400%, or 500%, including ranges between any two of these values compared to prior to the efflux. In some embodiments, the net influx of anions is effective to prevent an action potential in the neuron.

Methods of Enhancing Sodium Intake and/or Appetite

In some embodiments, a method of enhancing sodium intake and/or appetite in a subject in need thereof is described. The method can comprise, stimulating a plurality of pre-LC$^{PDYN}$ neurons of the subject, thereby enhancing sodium appetite in the subject. In some embodiments, the method comprises enhancing depolarization of the cell membranes of the plurality pre-LC$^{PDYN}$ neurons. Thus, stimulation of the plurality of pre-LC$^{PDYN}$ neurons can be enhanced, thus enhanced sodium intake and/or appetite in the subject. In some embodiments, the method comprises at least one of enhancing cation influx into a cytosol of the plurality of pre-LC$^{PDYN}$ neurons, inhibiting anion influx into the cytosol of the plurality of pre-LC$^{PDYN}$ neurons, and inhibiting cation efflux from the cytosol of the plurality of pre-LC$^{PDYN}$ neurons. In some embodiments, the method comprises administering a vector encoding an inhibitory ion modulator to the subject as described herein.

The method comprises, in some embodiments, determining sodium intake and/or appetite in the subject before stimulating the plurality of pre-LC$^{PDYN}$ neurons of the subject, determining sodium intake and/or appetite in the subject after stimulating the plurality of pre-LC$^{PDYN}$ neurons of the subject, or both. The extent to which the sodium intake and/or appetite is enhanced in the subject can vary. For example, the sodium intake and/or appetite of the subject is enhanced by, by about, by at least, or by at least about, 10%, 20%, 30%, 40%, 50%, 60%, 70%, 80%, 90%, 95%, 98%, or a range between any two of these values, as compared to the sodium and/or appetite of the subject before application of the method. In some embodiments, enhancing sodium appetite in the subject comprises reducing sodium ingestion for the subject. Some of the plurality of pre-LC$^{PDYN}$ neurons can express, for example, forkhead box protein P2 (FOXP2). For example, at least 10%, 20%, 30%, 40%, 50%, 60%, 70%, 80%, 90%, 95%, 98%, or a range of any two of these values, of the plurality of pre-LC$^{PDYN}$ neurons express FOXP2.

In some embodiments, stimulating the plurality of pre-LC$^{PDYN}$ neurons of the subject comprises inhibiting a plurality of GABAergic neurons in the bed nucleus of the stria terminalis (BNST), central amygdala, or both of the subject. For example, the plurality of GABAergic neurons in BNST, central amygdala, or both of the subject can comprise PDYN-positive neurons. In some embodiments, stimulating the plurality of pre-LC$^{PDYN}$ neurons of the subject comprises stimulating a plurality of HSD2 neurons in the nucleus of solitary tract (NTS$^{HSD2}$ neurons) in the subject.

Various methods/techniques can be used to stimulating pre-LC$^{PDYN}$ neurons. For example, the inhibition can comprise optogenetic stimulation, chemogenetic stimulation, or both. In some embodiments, stimulating the plurality of pre-LC$^{PDYN}$ neurons of the subject comprises stimulating the plurality of pre-LC$^{PDYN}$ neurons by an inhibitory conditional ion modulator.

The duration in which the plurality of pre-LC$^{PDYN}$ neurons is stimulated can vary. For example, a duration can be, 1 minute, 2 minutes, 3 minutes, 4 minutes, 5 minutes, 10 minutes, 20 minutes, 30 minutes, 40 minutes, 50 minutes, 100 minutes, 150 minutes, 200 minutes, or a range between any two of these values, or more. In some embodiments, the neuron is stimulated throughout the selected duration. In some embodiments, the neuron is stimulated with intervals of non-modulating break during the selected duration. In some embodiments, stimulating the plurality of pre-$LC^{PDYN}$ neurons lasts for at least five minutes in total.

In some embodiments, the method comprises identifying the subject as in need of enhancing sodium intake and/or appetite. For example, the subject can be identified as suffering from or at a risk of developing hyponatremia, excessive sweating, or a combination thereof. In some embodiments, the subject is a human or a non-human mammal. In some embodiments, the subject is an elderly subject. In some embodiments, the method of enhancing sodium intake and appetite is a method of ameliorating, inhibiting, delaying the onset of, reducing the severity of, or preventing hyponatremia, excessive sweating, or a combination thereof.

Identification of Modulators of Sodium Appetite and/or Intake

As used herein, a modulator of sodium appetite and/or intake refers to a compound (e.g., a small molecule compound, a nucleic acid, a protein, a lipid, a carbohydrate, or any combination thereof) that can partially or fully inhibit sodium appetite and/or intake; or a compound (e.g., a small molecule compound, a nucleic acid, a protein, a lipid, a carbohydrate, or any combination thereof) that can partially or fully enhance sodium appetite and/or intake. A modulator of sodium appetite and/or intake can be, for example, a modulator of pre-$LC^{PDYN}$ neurons, a modulator of $NTS^{HSD2}$ neurons, a modulator of GABAergic neurons in the bed nucleus of the stria terminalis (BNST) and/or central amygdala, or any combination thereof. A modulator of neurons (including, but not limited to, pre-$LC^{PDYN}$ neurons, $NTS^{HSD2}$ neurons, and GABAergic neurons) can be a compound (e.g., a small molecule compound, a nucleic acid, a protein, a lipid, a carbohydrate, or any combination thereof) that can partially or fully inhibit the neurons; or a compound (e.g., a small molecule compound, a nucleic acid, a protein, a lipid, a carbohydrate, or any combination thereof) that can partially or fully stimulate the neurons.

The modulator of a neuron can be, for example, an activator (or stimulator) of the neuron which can partially or fully activate the neuron. For example, the activator can activate the neuron activity by, or by at least, 10%, 20%, 30%, 40%, 50%, 60%, 70%, 80%, 90%, 95%, 98%, 99%, or a range between any two of these values. In some embodiments, the activator can activate the neuron activity by, or by at least, 0.5-fold, 1-fold, 1.5-fold, 2-fold, 2.5-fold, 3-fold, or more, or a range between any two of these values.

The modulator of a neuron can also be, for example, an inhibitor of the neuron which can partially or fully inhibit the neuron. For example, the inhibitor can reduce the neuron activity by, or by at least, 10%, 20%, 30%, 40%, 50%, 60%, 70%, 80%, 90%, 95%, 98%, 99%, or a range between any two of these values. In some embodiments, the inhibitor can reduce the neuron activity by, or by at least, 0.5-fold, 1-fold, 1.5-fold, 2-fold, 2.5-fold, 3-fold, or more, or a range between any two of these values.

In some embodiments, identification of inhibitors of neurons of interest comprises screening compounds for their ability to act as antagonists to activate the neurons. The neurons of interest comprise, pre-$LC^{PDYN}$ neurons, $NTS^{HSD2}$ neurons, GABAergic neurons, or a combination thereof. In some embodiments, compounds are also screened to determine whether or not they inhibit one or more known agonists for the neurons of interest, or whether or not they activate one or more known antagonists for the neurons of interest. Screening assays are well known in the art and can readily be adapted to identify antagonists of neurons, such as pre-$LC^{PDYN}$ neurons, $NTS^{HSD2}$ neurons, and GABAergic neurons. Antagonists of a neuron, for example pre-$LC^{PDYN}$ neuron, may include compounds that interact with (e.g., bind to) a pre-$LC^{PDYN}$ neuron (e.g., a synaptic receptor on the neuron); compounds that binds to and block neurotransmitters from binding or by decreasing the amount of time neurotransmitters are in the synaptic cleft; compounds that block the synaptic connection of a pre-$LC^{PDYN}$ neuron with a neuron that is capable of being synaptically connected with the pre-$LC^{PDYN}$ neuron; or a combination thereof. In some embodiments, the modulator is a suppressor for sodium appetite. The method disclosed herein, in some embodiments, comprises identifying the candidate compound as a suppressor for sodium appetite if the candidate compound reduces valence toward sodium of the subject compared to a control.

In some embodiments, identification of activators of neurons of interest (e.g., pre-$LC^{PDYN}$ neurons, $NTS^{HSD2}$ neurons, and GABAergic neurons) comprises screening compounds for their ability to act as agonists to activate the neurons. In some embodiments, compounds are also screened to determine whether or not they activate one or more known agonists for the neurons, or whether or not they inhibit one or more antagonists for the neurons. Screening assays are well known in the art and can readily be adapted to identify agonists of neurons, such as pre-$LC^{PDYN}$ neurons, $NTS^{HSD2}$ neurons, and GABAergic neurons. Agonists of a neuron, for example pre-$LC^{PDYN}$ neuron, may include compounds that interact with (e.g., bind to) a pre-$LC^{PDYN}$ neuron; compounds that block neurotransmitters from reentering the pre-synaptic axon terminal; compounds that enhance the synaptic connection of a pre-$LC^{PDYN}$ neuron with a neuron that is capable of being synaptically connected with the pre-$LC^{PDYN}$ neuron; or a combination thereof. In some embodiments, the modulator is an enhancer for sodium appetite. The method disclosed herein, in some embodiments, comprises identifying the candidate compound as an enhancer for sodium appetite if the candidate compound enhances valence toward sodium of the subject compared to a control.

As disclosed herein, a method of identifying a modulator for sodium appetite can comprises: (a) contacting a candidate compound with a plurality of pre-$LC^{PDYN}$ neurons of a subject; (b) selecting the candidate compound as a modulator of the pre-$LC^{PDYN}$ neurons if the candidate compound alters an electrophysiological response in the pre-$LC^{PDYN}$ neurons; (c) assessing the change in valence toward sodium of the subject in response to the administration of the selected candidate compound; and (d) identifying the candidate compound as a modulator for sodium appetite if the candidate compound changes the valence toward sodium of the subject compared to a control. Many assays are known in the art to measure the electrophysiological response of a plurality of neurons. Examples of assays that can be used in the methods disclosed herein to measure, and thus determine alteration in an electrophysiological response in the pre-$LC^{PDYN}$ neurons, include, but are not limited to, a $Ca^{2+}$ influx assay, a patch clamp assay, a calcium mobilization assay, a calcium imaging assay, an electrical signal detection assay, an assay based on fluorescent calcium sensor GCaMP6s, or a combination thereof.

Contacting the candidate compound with the plurality of pre-LC$^{PDYN}$ neurons comprises administering the candidate compound to the subject via injection. The candidate compound can be, for example, a small molecule, peptide, a nucleic acid, or a combination thereof. The compounds that can be screened include, but are not limited to, small molecules (including both organic and inorganic molecules); peptides, proteins, antibodies and fragments thereof, and other organic compounds (e.g., peptidomimetics); nucleic acids; lipids; carbohydrates, or a combination thereof. For example, the candidate compounds can include, but are not limited to, soluble peptides, including members of random peptide libraries (see e.g., Lam, K. S. et al., 1991, Nature 354:82-84; Houghten, R. et al., 1991, Nature 354:84-86), and combinatorial chemistry-derived molecular libraries made of D- and/or L-configuration amino acids, phosphopeptides (including, but not limited to members of random or partially degenerate, directed phosphopeptide libraries; see e.g., Songyang, Z. et al., 1993, Cell 72:767-778), antibodies (including, but not limited to, polyclonal, monoclonal, humanized, anti-idiotypic, chimeric or single chain antibodies, and FAb, F(abN).sub.2 and FAb expression library fragments, and epitope-binding fragments thereof), and small organic or inorganic molecules, including libraries thereof. Other compounds that can be screened in accordance with the present application include, but are not limited to, small organic molecules, for example, those that are able to cross the blood-brain barrier.

Many methods are available for generating random or directed synthesis (e.g., semi-synthesis or total synthesis) of any number of polypeptides, chemical compounds, including, but not limited to, saccharide-, lipid-, peptide-, and nucleic acid-based compounds. Synthetic compound libraries are commercially available from Brandon Associates (Merrimack, N. H.) and Aldrich Chemical (Milwaukee, Wis.). In some embodiments, chemical compounds to be used as candidate compounds can be synthesized from readily available starting materials using standard synthetic techniques and methodologies known to those of skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Libraries of known compounds, including natural products or synthetic chemicals, and biologically active materials, including proteins, can be screened for compounds which can activate or inhibit neurons of interest, for example pre-LC$^{PDYN}$ neurons, NTS$^{HSD2}$ neurons, and GABAergic neurons. The molecular weight of the small molecule candidate compounds that can be screened for such activity can vary. For example, the small molecule can have a molecular weight of less than about 10 kD, about 8 kD, about 5 kD, about 2 kD, or a range between any two of these values. The small molecules can be, for example, naturally-occurring small molecules, synthetic organic or inorganic compounds, peptides and peptide mimetics. Small molecules in the present application are not limited to these forms. Extensive libraries of small molecules are commercially available, and a wide variety of assays are well known in the art to screen these molecules for the desired activity.

In some embodiments, modulators for sodium intake and/or appetite are identified from large libraries of natural product or synthetic (or semisynthetic) extracts or chemical libraries or from polypeptide or nucleic acid libraries, according to methods known in the art. Those of skill in the field of drug discovery and development will understand that the precise source of test extracts or compounds is not critical to the screening procedure(s) disclosed herein. Agents used in screens can include those known as therapeutics for the treatment of conditions such as anxiety, stress, itching, and/or pain. Virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as the modification of existing polypeptides.

Libraries of natural polypeptides in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). Such polypeptides can be modified to include a protein transduction domain using methods known in the art and described herein. In addition, natural and synthetically produced libraries are produced, if desired, according to methods known in the art, e.g., by standard extraction and fractionation methods. Examples of methods for the synthesis of molecular libraries can be found in the art, for example in: DeWitt et al, Proc. Natl. Acad. Set U.S.A. 90:6909, 1993; Erb et al, Proc. Natl. Acad. Sci. USA 91:11422, 1994; Zuckermann et al, J. Med. Chem. 37:2678, 1994; Cho et al, Science 261:1303, 1993; Carrell et al, Angew. Chem. Int. Ed. Engl. 33:2059, 1994; Carell et al, Angew. Chem. Int. Ed. Engl. 33:2061, 1994; and Gallop et al, J. Med. Chem. 37:1233, 1994. Furthermore, if desired, any library or compound is readily modified using standard chemical, physical, or biochemical methods.

EXAMPLES

Some aspects of the embodiments discussed above are disclosed in further detail in the following examples, which are not in any way intended to limit the scope of the present disclosure.

Experimental Material and Methods

The following experimental materials and methods were used for Examples 1 and 2 described below.

Animals

All procedures followed animal care guidelines from NIH for the care and use of laboratory animals and California Institute of Technology Institutional Animal Care and Use Committee (1694-14). Animals at least six weeks old were used for experiments. The following mice were purchased from the Jackson Laboratory: C57BL/6J, stock number 00064. Slc17a6-Cre, stock number 016963. Ai75D, stock number 025106, Ai3, stock number 007903. HSD2-Cre mice were provided by A. and G. Fejes-Toth (Dartmouth Medical School). PDYN-GFP mice were provided by D. Kong (Tufts University School of Medicine). PDYN-Cre mice were provided by B. Lowell (Harvard Medical School) and M. Krashes (NIH). Ail 10 line was provided by D. Anderson (Caltech). Mice were housed on a 13 h: 11 h light: dark cycle with ad libitum access to food and water except for specific depletion experiments (water, food, sodium). Male and female mice were used for experiments.

Viral Constructs

The following AAV viruses were purchased from the UNC Vector Core AAV1-CAG-flex-RG ($3.0 \times 10^{12}$ genome copies per ml), AAV1-EF1a-flex-TVA-mCherry ($6.0 \times 10^{12}$ genome copies per ml), AAV2-EF1a-DIO-eYFP ($4.6 \times 10^{12}$ genome copies per ml), AAV1-EF1a-DIO-ChR2-mCherry ($5.1 \times 10^{12}$ genome copies per ml), AAV5-Ef1a-DIO iC++-eYFP ($4.5 \times 10^{12}$ genome copies per ml), AAV5-flex-ta-Casp3-TEVp ($4.5 \times 10^{12}$ genome copies per ml). The following AAV viruses were purchased from the UPenn virus core, AAV1-hSyn1-flex-GCaMP6s-WPRE-SV40 ($2.28 \times 10^{13}$ genome copies per ml), AAV5-EF1a-DIO-ChR2-eYFP ($3.3 \times 10^{13}$ genome copies per ml), AAV1-EF1a-DIO-ChR2-mCherry ($2.0 \times 10^{13}$ genome copies per ml). The following AAV viruses were purchased from Addgene, AAV8-hSyn-DIO-hM4D(Gi)-mCherry ($1.9 \times 10^{13}$ genome copies per ml), AAV5-hSyn-DIO-mCherry ($1 \times 10^{13}$ genome copies per ml), AAV8-Ef1a-DIO-iC++-eYFP ($8.5 \times 10^{13}$ genome copies per ml) was purchased from the Stanford Virus vector core. SAD-ΔG-BFP ($1.7 \times 10^{9}$ genome copies per ml) was purchased from Salk. CAV-Cre ($1.5 \times 10^{13}$ genome copies per ml) was purchased from Plateforme de Vectorologie de Montpellier (PVM).

Surgery

Mice were anaesthetized with a mixture of ketamine (1 mg/mL) and xylazine (10 mg/mL) in isotonic saline, intraperitoneally injected at 10 µl/g body weight. Ketoprofen was subcutaneously administered at 5 µl/g body weight. The animal was placed in a stereotaxic apparatus (Narishige Apparatus) with a heating pad. Surgery was performed as previously described. The three-dimensional MRI coordinate system was used as a reference for the injection site coordinates. Viral constructs were injected using a microprocessor-controlled injection system (Nanoliter 2000, WPI) at 100 nl/min. The coordinates for pre-LC are AP: −9000, ML: ±1000, DV: −3900 (60-100 nl injection), for dBNST are AP: −3100 ML: 1100 DV: −3600 (100 nl injection), for NTS are AP: −10800 ML: ±150 DV: −5100, −5300 (100-300 nl injection each).

For optogenetic experiments, implants were made with a 200 µm fiber bundle (FT200EMT, Thorlabs) glued to a ceramic ferrule (CF230 or CFLC230, Thorlabs). For photometry, customized implants (400 µm diameter, Doric Lenses) were used. A fiber implant was placed 200-300 µm (for optogenetic) or 0-50 µm (for photometry) above the virus injection site. Histology position of fiber implant was confirmed after data collection. Data from implant disposition was not included. For IG infusion, catheter construction and implantation closely followed as described previously. IG catheters were custom made using silastic tubing (Dow Corning, 508-002), tygon tubing (Instech, BTPE-25) and pinport (Instech, PNP3F25-50). For photometry recording, IG surgery was performed after animals recovered from the initial implantation of an optic fiber. After surgery, all animals were placed in a clean cage placed on a heating pad overnight and then were housed in the animal facility. Behavioral and histological assays were performed after at least 10 days of recovery. For ablation experiments, AAV-flex-taCasp3-TEVp or AAV-hSyn-DIO-mCherry (control) was injected. These animals were sodium-depleted after 2-3 weeks of recovery. At the end of experiments, all animals were sacrificed for histological examination. For fiber implantation experiments, it was occasionally observed that the position of an implanted fiber shifted in the hindbrain due to cranial deformation.

Optogenetic and Chemogenetic Manipulations

For ChR2 photostimulation. 473 nm laser pulses (20 ms, 20 Hz) were delivered via an optic cable (MFP-FC-ZF, Doric Lenses) using a pulse generator (Sapphire 9200 from Quantum composers or SYS-A310 from WPI). The laser intensity was maintained at 5-10 mW at the tip of the fiber. Unless otherwise noted, photostimulation was delivered for 1 s at 3 s intervals throughout the behavior session. For iC++ photoinhibition, 473 nm laser was continuously turned on throughout the session at 3 mW at the tip of the fiber. For chemogenetic manipulation (FIGS. 8E-H), CNO (Sigma, 10 mg/kg) or vehicle (water) was administered intraperitoneal 20 min before the sodium consumption experiment.

Preference Assay

To induce sodium appetite, animals were injected with furosemide (Sigma) at a dose of 50 mg/kg body weight. Low sodium diet (TD. 90228, ENVIGO) was provided for 2 days after the injection of furosemide. For water-restriction experiments, animals were kept in their home cage without water, and were provided with 1 mL of water daily. For food restriction experiments, animals were deprived of food up to 24 hrs with normal water provided. All assays were performed in a custom gustometer (Dialog Instruments) or Biodaq monitoring system (Research Diets Inc). All sodium-depleted animals were trained in a gustometer before experiments. Animals which licked at least 150 licks during the 30-min session were used for further behavioral assays. After every sodium-depletion round, animals were recovered for at least 4 days with the normal diet.

For appetite specificity assay (FIG. 7C), three different solutions were presented to animals during the same session, and their preference was measured as a lick number. For each trial, 20 sec of photostimulation was delivered to the animal with an inter-trial-interval of 60 secs. Water, 0.5 M KCl, 0.5 M NaCl, or 0.5 M NaCl+30 µM amiloride was used for preference assay. For sodium consumption assay (FIGS. 1E, 1G, and 1H), animals were given ad libitum access to 0.5 M NaCl, water or an empty spout for either 7.5 or 30 min.

For photometry recording, animals were given either 5- or 10-minutes access to stimuli. To examine sodium specific responses of pre-LC$^{PDYN}$ neurons (FIGS. 3D, 3E), animals were presented with three solutions during the session. First, animals were given 5 min access to 0.5 M KCl (FIG. 3D) or 0.5 M NaCl+0.1 mM amiloride (FIG. 3E). Then animals had 5 min access to water. Finally, animals were given 5 min access to 0.5 M NaCl. The interval between trials was 5 min.

Rock Salt Intake Behavioral Assay

Sodium-depleted animals were acclimatized for 1 hour in an acrylic box (50 cm×25 cm×25 cm) with a rock salt (Halite Himalayan Crystal Salt). Then the lick events of rock salt were monitored for 30 min using a webcam under sated, sodium depleted, or photostimulated conditions. The start and end of bouts were manually annotated and quantified.

Real-Time Place Preference

Real-time place preference was performed in a two-chamber acrylic box (50 cm×25 cm×25 cm) as described previously. Each side of the chamber had distinct visual and textural cues (different size and shape of holes of plastic bin). A custom MATLAB code was used for real-time optogenetic stimulation and analyzing the place preference. The initial preference for each animal was determined during the initial 30-min session without photostimulation, which was followed by three test sessions with photostimulation. Light (20 Hz, 5s ON 5s OFF) was delivered through an optic fiber in the initially-preferred side.

Negative Reinforcement Assay

To examine if appetite neurons transmit negative valence, animals were first acclimatized in the operant conditioning chamber (MedAssociate). After acclimatization, the animals were trained to press the lever to avoid negative stimulus (foot shock at 0.15-0.18 mV). Each lever press paused the foot shock for 20 sec. Training was completed when an animal pushed the lever more than 20 times during the 30-min session. In a test session, animals were given continuous 20 Hz photostimulation to the pre-LC, which was paused for 20 sec by each lever press. The number of lever presses during the session was quantified.

Intragastric Infusion

In FIG. 4B, 0.5 M NaCl, deionized water, or glucose solution (5 M) was infused via an intragastric catheter. Solutions were delivered at 0.1 ml/min for 5 min (water and sodium) or 10 min (food) using an infusion syringe pump (NE-300, New Era Pump Systems Inc). 10 min after gastric infusion, animals were given access to nutrients and their consumption was quantified for 10 min (for water and 0.5 M NaCl), or 30 min (for normal chow). Either air infusion (for water), or water infusion (for sodium and food) was used as a control stimulus. In FIG. 4D, either 0.15 M NaCl, water, or air was infused at a rate of 0.1 ml/min while recording the neural activity by photometry. For control, oral ingestion (FIG. 4C), the same set of animals were given access to 0.15 M NaCl.

Fibre Photometry

For all photometry assays, animals were acclimatized for 10-15 min in the chamber before stimuli were presented. Bulk fluorescence signals were collected using fibre photometry as previously described. Briefly, data were extracted and subjected to a low-pass filter at 1.8 Hz. A linear function was used to scale up the 405-nm channel signal to the 490-nm channel signal to obtain the fitted 405-nm signal. The resultant $\Delta F/F$ was calculated as (raw 490 nm signal−fitted 405 nm signal)/(fitted 405 nm signal). $\Delta F/F$ was then time-binned by a factor of 2.5 times the sampling frequency and down-sampled to 10 Hz. For all bouts, the mean fluorescence for 5 min before the first lick was calculated and subtracted from the entire session. The licks from the lickometer were simultaneously recorded. The area under the curve (AUC) was quantified by integrating the baseline-subtracted fluorescence signals for 30 sec after the start of the bout. For FIG. 10D, the data were quantified as $\Delta F/F$ change between 1 sec prior to, and at the first lick (0 sec). For IG infusion experiments (FIG. 4E), AUC was quantified during the 5-min of infusion.

Retrograde Viral Tracing

For monosynaptic rabies tracing of pre-LC$^{PDYN}$, 100 nl of a mixture of AAV1-CAG-flex-RG and AAV1-EF1a-flex-TVA-mCherry (4:1 ratio) was injected to the pre-LC. Two weeks later, 200 nl of SAD-AG-BFP was injected into the pre-LC. The mice were euthanized a week later.

To label the dBNST→pre-LC circuit, 100 nl of CAV-Cre was injected into the pre-LC followed by the injection of AAV5-DIO-mCherry or AAV1-flex-GCaMP6S into the dBNST. These animals were used for experiments at least two weeks after the injection.

Histology

Mice were anaesthetized and were perfused with PBS followed by 4% PFA in PBS (pH 7.4). The brain was dissected and fixed in 4% PFA at 4° C. for overnight. Fixed samples were sectioned into 100 μm coronal sections using a vibratome (Leica, VT-1000 s). For immunohistochemistry (IHC), brain sections were incubated in a blocking buffer (10% Donkey serum, 0.2% Triton-X) for 1-2 hrs. Then sections were incubated with primary antibodies diluted in blocking buffer: goat anti-c-Fos (1:500, Santa Cruz, SC-52G), rabbit anti-c-Fos (1:1000, Millipore ABE457), rabbit anti-GAD65+GAD67 (1:500, Abcam, ab183999), chicken anti-GFP (1:1000, Abcam, ab13970), rat anti-mCherry (1:500, Thermo Fisher, M11217), sheep anti-Foxp2 (1:2000, R&D systems, AF5647), and rabbit anti-HSD211β2 (1:300, proteintech, 14192-1-AP). Samples were incubated with primary antibodies overnight. After washing three times with PBS, the sections were incubated with secondary antibodies (1:500 dilutions, Jackson laboratory) in blocking buffer for 4 h. For an exception, GAD65+GAD67 staining was performed without Triton-X. Fluorescence in situ hybridization (FISH) was carried out in frozen brain sections using the RNAscope fluorescent multiplex kit (Advanced Cell Diagnostics) following the manufacturer's instructions. IHC staining was applied for eYFP after FISH.

Slice Electrophysiology

250-μm coronal slices were obtained using a vibratome (VT-1000s, Leica) in ice-cold sucrose-aCSF (artificial cerebrospinal fluid) solution (Sucrose 213, KCl 2.5, NaH$_2$PO$_4$ 1.2, NaHCO$_3$ 25, glucose 10, MgSO$_4$ 7, CaCl$_2$ 1, in mM at pH 7.3), and then incubated in HEPES-holding aCSF (NaCl 92, KCl 2.5, NaH$_2$PO$_4$ 1.2, NaHCO$_3$ 30, HEPES 20, glucose 25, Na-ascorbate 5, thiourea 2, Na-pyruvate 3, MgSO$_4$ 2, CaCl$_2$ 2, in mM at pH 7.3-7.4). Slices were recovered at 34.5° C. for 45 min and then held at room temperature until use.

For patch-clamp recording, slices were placed in a recording chamber perfused with aCSF (NaCl 124, KCl 2.5, NaH$_2$PO$_4$ 1.2, NaHCO$_3$ 25, glucose 10, MgSO$_4$ 1, CaCl$_2$ 2, in mM, at pH 7.3) on an upright microscope (Examiner.D1, Zeiss). Whole-cell recordings were achieved using glass pipettes (5-8 MΩ) filled with intracellular solution (for DREADD and iC++ experiments, K-gluconate 145, NaCl 2, KCl 4, HEPES 10, EGTA 0.2, Mg-ATP 4, Na-GTP 0.3; for GABAergic postsynaptic currents, CsCl 145, NaCl 2, HEPES 10, EGTA 0.2, QX-314 bromide 5, Mg-ATP 4, Na-GTP 0.3, in mM at pH 7.25; for glutamatergic postsynaptic currents, Cs(CH$_3$)SO$_3$ 145, NaCl 2, HEPES 10, EGTA 0.2, QX-314 bromide 5, Mg-ATP 4, Na-GTP 0.3, in mM, at pH 7.25). Electrical signals were filtered at 3 k Hz with Axon MultiClamp 700B (Molecular Devices) and collected at 20 kHz with Axon Digidata 1550A (Molecular Devices).

To obtain light-evoked responses, the light beam from an LED light source (X-Cite 120LED, Excelitas Technologies) was delivered through an optical filter (475/30) and then 40× water-immersion objective (Zeiss) onto neurons. For iC++ experiments, the light was turned on continuously for 10s, while for DREADD experiments, 10 μM CNO was puffed (10 sec) using a glass pipette. For CRACM experiments, 2-msec light pulses were given either 5 times at 1 Hz for 4 cycles or 1 time for 20 cycles. To verify GABAergic connections, picrotoxin (PTX, 100 μM) was applied through perfusion, whereas for glutamatergic connections, 6-Cyano-7-nitroquinoxaline-2,3-dione (CNQX, 10 μM) and DL-2-Amino-5-phosphonopentanoic acid (APV, 25 μM) were used.

Statistics for various figures included in the present disclosure are shown in Table 1.

TABLE 1

| | Statistics | | |
|---|---|---|---|
| Figure Number | Sample size (n = mice otherwise stated) | Test | P value |
| 1a; Control vs −Sodium | 5.5 | Kruskal-Wallis test (Dunn's multiple comparisons test) | 0.0015 |
| 1e; Empty vs NaCl | 4.10 | Kruskal-Wallis test (Dunn's multiple comparisons test) | 0.0204 |
| 1e; Water vs NaCl | 10.10 | Kruskal-Wallis test (Dunn's multiple comparisons test) | 0.0002 |
| 1f Total bout duration (s); −Sodium vs −Light | 4.8 | Kruskal-Wallis test (Dunn's multiple comparisons test) | 0.0038 |
| 1f Total bout duration (s); −Light vs +Light | 8.8 | Kruskal-Wallis test (Dunn's multiple comparisons test) | 0.0031 |
| 1f # of bout; −Sodium vs −Light | 4.8 | Kruskal-Wallis test (Dunn's multiple comparisons test) | 0.0018 |
| 1f # of bout; −Light vs +Light | 8.8 | Kruskal-Wallis test (Dunn's multiple comparisons test) | 0.0046 |
| 1g; Non-stim vs co-stim | 8.8 | Friedman test (Dunn's multiple comparisons test) | 0.0009 |
| 1h; −Light vs +Light | 7.7 | two-tailed Wilcoxon test | 0.0156 |
| 2a, Session 1; eYFP vs ChR2 | 8.10 | two-way repeated measure ANOVA (Sidak's multiple comparisons test) | 0.0016 |
| 2a, Session 2; eYFP vs ChR2 | 8.10 | two-way repeated measure ANOVA (Sidak's multiple comparisons test) | 0.0117 |
| 2a, Session 3; eYFP vs ChR2 | 8.10 | two-way repeated measure ANOVA (Sidak's multiple comparisons test) | <0.0001 |
| 2b, ChR2; +light vs −light | 6.6 | two-tailed Wilcoxon test | 0.0313 |
| 3c left; water vs 0.06M NaCl | 8.7 | Kruskal-Wallis test (Dunn's multiple comparisons test) | 0.0041 |
| 3c left; water vs 0.15M NaCl | 8.7 | Kruskal-Wallis test (Dunn's multiple comparisons test) | 0.0088 |
| 3c left; water vs 0.5M NaCl | 8.7 | Kruskal-Wallis test (Dunn's multiple comparisons test) | 0.0016 |
| 3d; KCl vs NaCl | 9.9 | two-tailed Wilcoxon test | 0.0039 |
| 3e; +Ami vs −Ami | 9.9 | two-tailed Wilcoxon test | 0.0039 |
| 4b left; Control vs NaCl Oral | 7.7 | Friedman test (Dunn's multiple comparisons test) | 0.0323 |
| 4b middle; Control vs Water IG | 8.8 | Kruskal-Wallis test (Dunn's multiple comparisons test) | 0.0221 |
| 4b middle; Control vs Water oral | 8.6 | Kruskal-Wallis test (Dunn's multiple comparisons test) | 0.0003 |
| 4b right; Control vs Glucose IG | 8.8 | two-tailed Wilcoxon test | 0.0078 |
| 4e left; NaCl IG vs NaCl Oral | 7.7 | Friedman test (Dunn's multiple comparisons test) | 0.0113 |
| 4e left; Water IG vs NaCl Oral | 7.7 | Friedman test (Dunn's multiple comparisons test) | 0.0214 |
| 4e left; Air IG vs NaCl Oral | 7.7 | Friedman test (Dunn's multiple comparisons test) | 0.0057 |
| 5b left; +Casp3 vs −Casp3 | 18.8 | two-tailed Mann-Whitney test | <0.0001 |
| 5b right; +Casp3 vs −Casp3 | 18.8 | two-tailed Mann-Whitney test | <0.0001 |
| 5f; +Ami vs −Ami | 7.7 | two-tailed Wilcoxon test | 0.0469 |
| 6b −Water; Water vs 0.5M NaCl | 9.9 | two-tailed Wilcoxon test | 0.0039 |
| 6b −Sodium; Water vs 0.5M NaCl | 9.9 | two-tailed Wilcoxon test | 0.0039 |
| 7a left, 0.06M NaCl; eYFP vs ChR2 | 5.4 | two-tailed Mann-Whitney test | 0.0159 |
| 7a right, 0.15M NaCl; eYFP vs ChR2 | 5.4 | two-tailed Mann-Whitney test | 0.0159 |
| 7c left, KCl; NaCl vs KCl | 9.9 | Friedman test (Dunn's multiple comparisons test) | 0.0044 |
| 7c left, KCl; KCl vs NaCl | 9.9 | Friedman test (Dunn's multiple comparisons test) | 0.0019 |
| 7c right, Ami; −Ami vs +Ami | 8.8 | Friedman test (Dunn's multiple comparisons test) | 0.0009 |
| 7c right, Ami; −Ami vs +Ami | 8.8 | Friedman test (Dunn's multiple comparisons test) | 0.0248 |
| 8g left, −Sodium; Vehicle vs CNO | 9.9 | two-tailed Wilcoxon test | 0.0078 |
| 9c; −Light vs +Light of Session 4 | 6.6 | two-tailed Wilcoxon test | 0.0313 |
| 10d right, NaCl; eYFP vs GCaMP6s | 7.7 | two-tailed Mann-Whitney test | 0.007 |
| 10d right, Empty; eYFP vs GCaMP6s | 4.4 | two-tailed Mann-Whitney test | 0.0286 |
| 10e left, KCl; KCl vs NaCl | 9.9 | two-tailed Wilcoxon test | 0.0039 |
| 10e left, Ami; +Ami vs −Ami | 9.9 | two-tailed Wilcoxon test | 0.0273 |
| 11b; −Light vs +Light | 6.6 | two-tailed Mann-Whitney test | 0.0065 |

Example 1

Identification of Pre-LC$^{PDYN}$ Neurons as Neurons Selectively Controls Sodium Intake This example describes a study for identifying a neural population that selectively controls sodium intake for gaining a circuit-level understanding of sodium appetite.

Figure 1A:
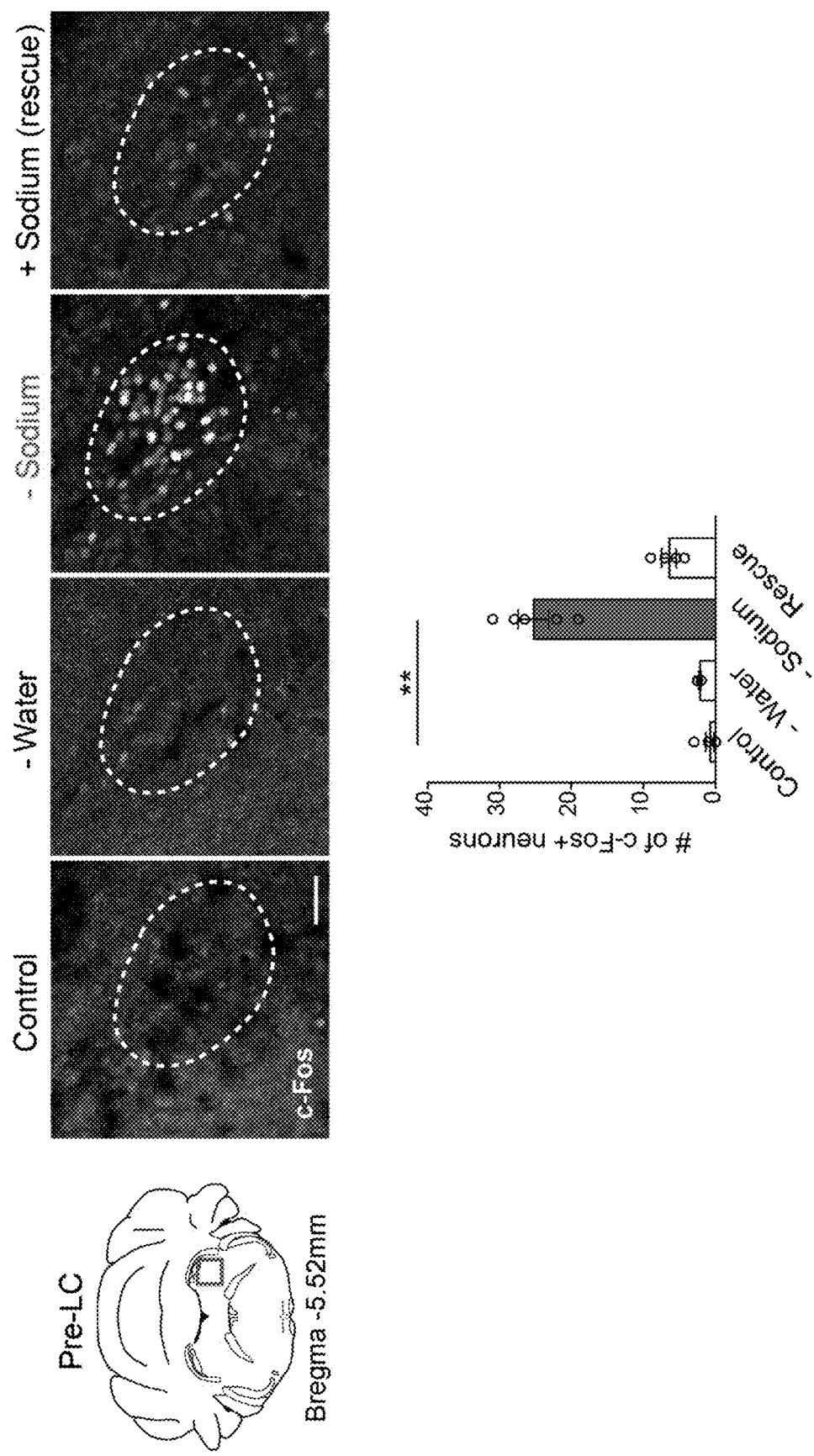
FIGS. 1A-H. Genetic and functional identification of sodium appetite neurons in the pre-LC.
Figure 1B:
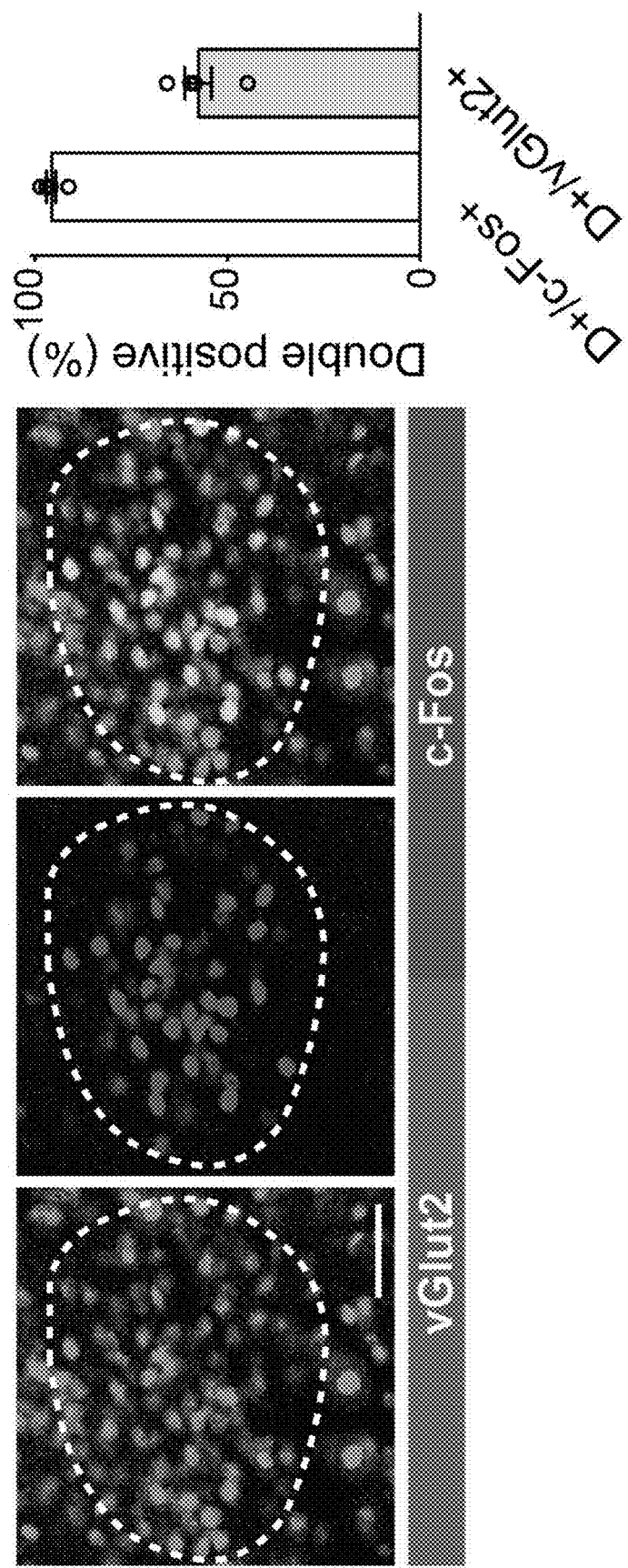
Figure 1C:
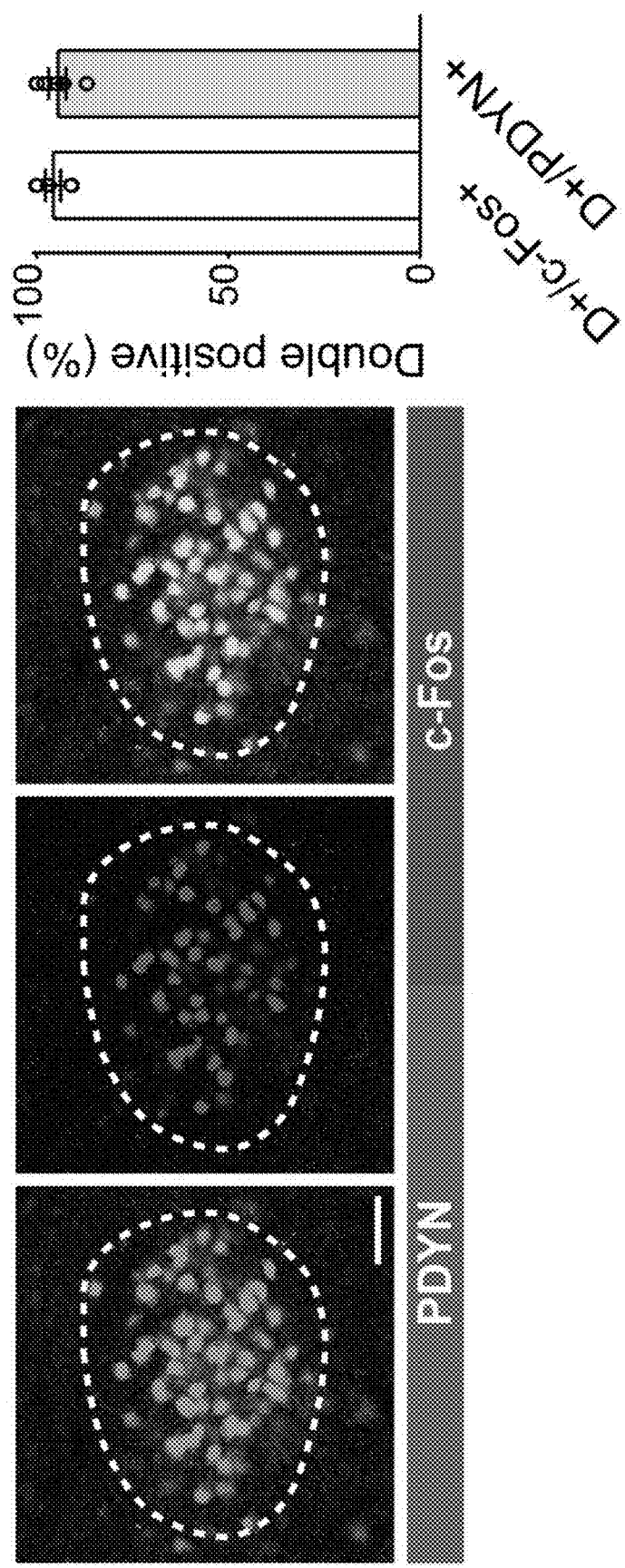
Figure 1E:
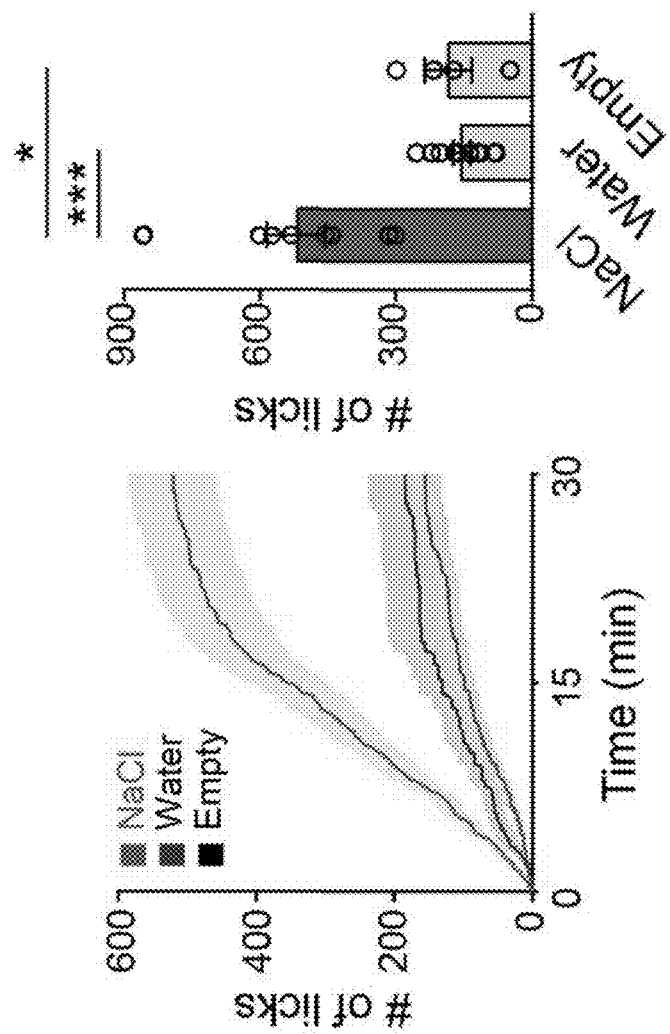
Figure 1D:
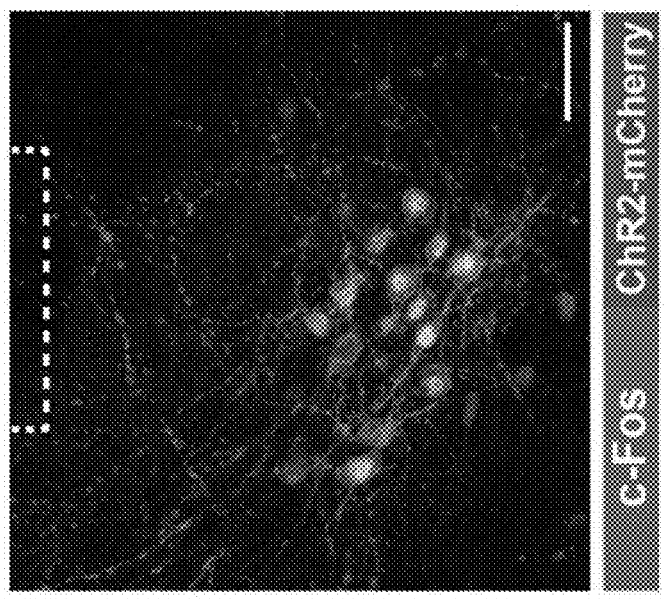
Figure 1F:
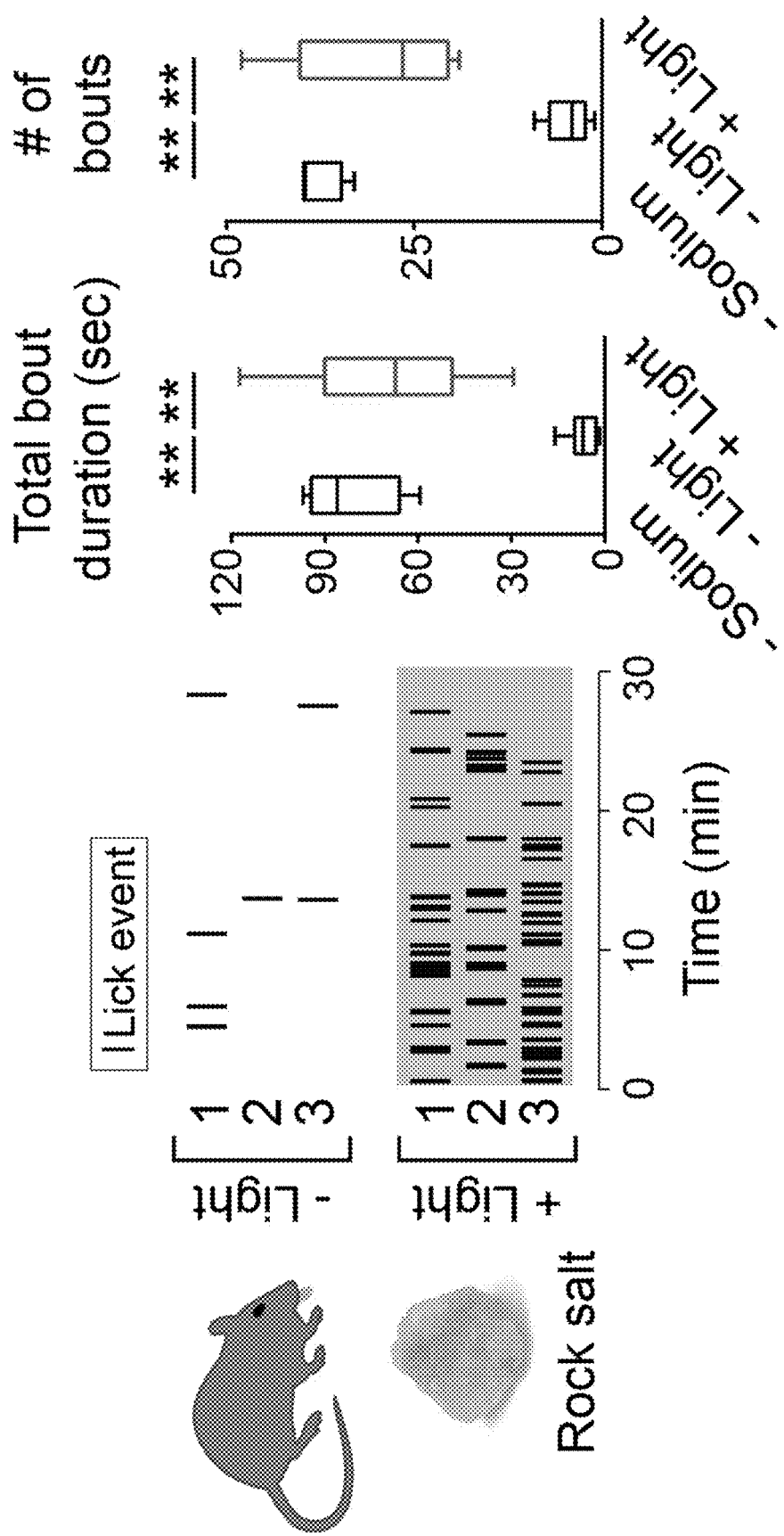
Figures 1G, 1H:
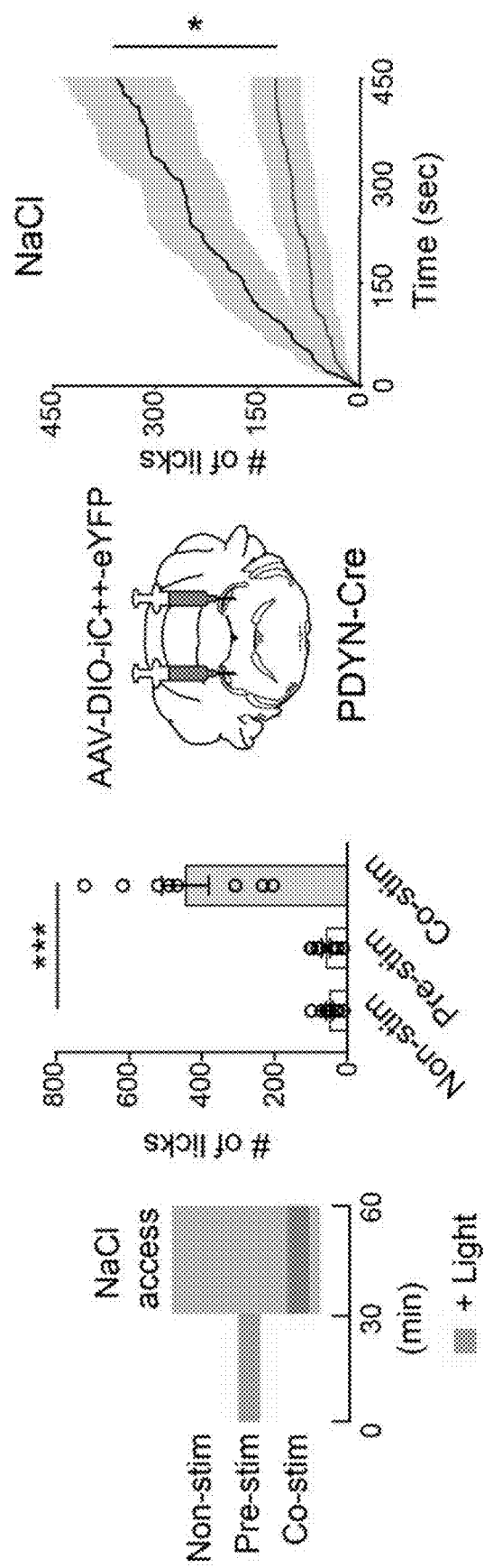

The pre-LC is a hindbrain nucleus that receives interoceptive information from the NTS, integrates inputs from other nuclei, and relays them to the forebrain structures. Because pre-LC neurons are activated under sodium-depletion, without being bound by any particular theory, it is believed that this nucleus serves as a central node that controls the drive for sodium consumption. Consistent with this notion, neurons in the pre-LC strongly expressed c-Fos, a neuronal activity marker, under sodium-depletion. The activation was not observed in sated, water-deprived, or sodium-rescued animals after depletion (FIG. 1A, FIGS. 6A-C). The histological analysis revealed that about 60% of pre-LC excitatory neurons are activated under sodium-depleted conditions (FIG. 1B). Genetic markers were further screened, and it was identified that PDYN expression faithfully (>90%) overlaps with sodium-depletion-activated neurons (pre-LC$^{PDYN}$ neurons, FIG. 1C, FIG. 6D). It was observed that pre-LC$^{PDYN}$ neurons co-expressed Foxp2, a genetic marker for sodium depletion-sensitive neurons in the pre-LC (FIG. 6E). The functional significance of these neurons was further investigated for sodium appetite by gain- and loss-of-function approaches. For optogenetic activation of pre-LC$^{PDYN}$ neurons, adeno-associated virus (AAV) encoding Cre-dependent channelrhodopsin (AAV-DIO-ChR2) was infected into the pre-LC of PDYN-Cre animals. This neural manipulation triggered robust sodium ingestion from a high concentration of NaCl solution (0.5 M) that is normally aversive under sated conditions (FIGS. 1D and 1E) or even from rock salt (FIG. 1F). The appetite was found to be sodium specific and was observed regardless of sex or time of the day (FIGS. 2A-B). Sodium consumption required concurrent stimulation of pre-LC$^{PDYN}$ neurons with sodium presentation (FIG. 1G).

The data shown in this example demonstrate that the ongoing activity of pre-LC$^{PDYN}$ neurons is required for driving sodium appetite.

Example 2

Functional Characterization of Pre-LC$^{PDYN}$ Population for Sodium Intake

Loss-of-function studies revealed the functional necessity of pre-LC$^{PDYN}$ neurons for sodium appetite. Photoinhibition of pre-LC$^{PDYN}$ neurons specifically suppressed sodium ingestion under sodium-depleted conditions (FIG. 1H and FIG. 8A-D). Similar results were obtained using chemogenetic inhibition (FIG. 8E-H). These gain-of-function and loss-of-function experiments demonstrate that pre-LC$^{PDYN}$ neurons have a critical role in sodium appetite and intake.

Classical behavioral studies suggest a model that nutrient deficiency evokes negative internal states, which drives animals toward consumption to alleviate such discomfort. To investigate whether sodium appetite neurons encode a specific valence, a two-chamber real-time place preference assay were used. It was found that photostimulation of pre-LC$^{PDYN}$ neurons significantly reduced occupancy time in the compartment paired with light (FIG. 2A). Thus, the activation of pre-LC$^{PDYN}$ neurons is an aversive stimulus to animals.

To determine if animals would perform a task to reduce the aversive state mediated by pre-LC$^{PDYN}$ neurons, an operant assay where each lever-press pauses continuous photostimulation of the pre-LC was used (FIG. 2B, left panel). Indeed, animals exhibited robust lever-press behavior to stop stimulation (FIG. 2B right panel, FIG. 9). Therefore, pre-LC$^{PDYN}$ neurons transmit a negative valence signal upon activation.

Central appetite circuits receive various sensory and behavioral modulations on a real-time basis. To investigate the regulatory mechanisms of sodium appetite neurons in vivo, fiber photometry recording from pre-LC$^{PDYN}$ neurons was utilized in awake animals during sodium consumption (FIG. 3A, FIG. 10A). Sodium-depleted animals were given access to various solutions while recording GCaMP6s fluorescent signals. It was found that the activity of pre-LC$^{PDYN}$ neurons was rapidly and persistently suppressed upon sodium ingestion (FIGS. 3A and 3C, FIG. 10B). This robust inhibition was not observed when animals licked water or an empty bottle (FIGS. 3B and 3C, FIGS. 10C and 10D). It was then examined if the persistent inhibition is selectively driven by chemosensory detection of sodium. In contrast to NaCl, no suppression was observed by KCl (0.5 M, FIG. 3D, FIG. 10E), excluding the possibility that the effect is induced by osmolality changes. Importantly, blocking the sodium taste receptor by amiloride fully abolished NaCl-induced suppression of pre-LC$^{PDYN}$ neurons (FIG. 3E, FIG. 10E). Moreover, a brief contact to NaCl was sufficient to induce robust suppression for several minutes (FIG. 3F). These results suggest that oral chemosensory signals, likely mediated by the taste system, mediate acute modulation of sodium appetite neurons.

Given the functional significance of the pre-LC$^{PDYN}$ population for sodium intake, without being bound by any particular theory, it was expected that inhibition of the pre-LC$^{PDYN}$ neurons contributes to satiety of sodium appetite. Photometry recording combined with intragastric (IG) infusion that allows sodium administration without stimulating orosensory systems was used to detect the inhibition (FIG. 4A). Surprisingly, it was found that gastric preloading of NaCl in sodium-depleted mice did not affect subsequent sodium ingestion, whereas oral NaCl contact quickly quenched the appetite (FIG. 4B left panel). Only after a long period of IG infusion, significant appetite reduction was observed (41.3±6.0% after 2 hrs, n=6 mice). In sharp contrast, IG water and glucose infusion in thirsty and hungry animals, respectively, suppressed water/food consumption shortly after the infusion (FIG. 4B middle and right panels). These results highlight two important aspects of satiety regulation. First, sodium chemosensory inputs are important for rapid satiety of sodium appetite. Second, individual appetite circuits appear to receive temporally-distinct modulations from post-oral signals.

Since pre-LC$^{PDYN}$ neurons are involved in taste-mediated satiety, without being bound any particular theory, it is believed that they should be solely suppressed by oral detection of sodium. Consistently, while oral NaCl consumption drastically reduced the neural activity of pre-LC$^{PDYN}$ neurons (FIGS. 4C and 4E), IG infusion of NaCl in the same set of animals had no inhibitory effect (FIGS. 4D and 4E), suggesting that oral sodium detection facilitates satiety of sodium appetite via persistent suppression of pre-LC$^{PDYN}$ neurons.

The results presented herein indicate a model that the pre-LC integrates the internal sodium need and sensory information to regulate real-time sodium appetite. Next, the neural circuits carrying these signals were dissected. Because HSD2 neurons in the NTS ($NTS^{HSD2}$) project to the pre-LC, it was tested if pre-$LC^{PDYN}$ neurons directly receive the interoceptive information from the NTS. Using ChR2-assisted circuit mapping (FIG. 5A and FIG. 11A), it was found that a majority of recorded pre-$LC^{PDYN}$ neurons received monosynaptic excitatory inputs from $NTS^{HSD2}$ neurons. The functional significance of this connection for pre-LC activity was further examined. Optogenetic stimulation of $NTS^{HSD2}$ neurons activated pre-$LC^{PDYN}$ neurons in sated animals (FIG. 11B). Conversely, ablation of $NTS^{HSD2}$ neurons by caspase greatly attenuated c-Fos expression in pre-$LC^{PDYN}$ neurons after sodium-depletion (FIG. 5B and FIGS. 11C and 11D). These data demonstrate that the excitatory $NTS^{HSD2} \rightarrow$ pre-$LC^{PDYN}$ connections are necessary and sufficient to activate pre-$LC^{PDYN}$ neurons under sodium-depletion.

A monosynaptic rabies tracing technique (SAD-AG-BFP) was also used to search for neural circuits that mediate chemo sensory-dependent inhibition. These tracing experiments identified several brain regions with most prominent inputs from the dorsal area of the bed nucleus of the stria terminalis (dBNST), and the central amygdala (FIG. 5C and FIG. 12A). Because the BNST was previously shown to contribute to sodium consumption, the functional analysis was focused on the dBNST→pre-LC circuit. In dBNST, a majority of RV-positive neurons were the inhibitory population that also expressed PDYN ($dBNST^{PDYN}$, FIG. 5D, FIG. 12B). It was confirmed in slice recording that $dBNST^{PDYN}$ neurons send monosynaptic inhibitory inputs to pre-$LC^{PDYN}$ neurons (FIG. 5E). Without being bound by any particular theory, it is believed that if this dBNST→pre-LC circuit mediates rapid satiety signals, dBNST neurons should be activated upon sodium ingestion. canine adenovirus (CAV2)-Cre were used to infect the pre-LC and AAV-flex-GCaMP6s were used to infect the dBNST in order to label dBNST→pre-LC neurons (FIG. 12C). As anticipated, optical recording from dBNST→pre-LC neurons demonstrated that they responded upon NaCl intake under sodium-depleted conditions, which were strongly inhibited by amiloride (FIG. 5F). Taken together, these results show that pre-$LC^{PDYN}$ neurons integrate sensory and internal information through multiple excitatory and inhibitory inputs.

All references cited herein, including patents, patent applications, papers, text books, and the like, and the references cited therein, to the extent that they are not already, are hereby incorporated herein by reference in their entirety. To the extent that any of the definitions or terms provided in the references incorporated by reference differ from the terms and discussion provided herein, the present terms and definitions control.

The foregoing written specification is considered to be sufficient to enable one skilled in the art to practice the invention. The foregoing description and examples detail certain preferred embodiments of the invention and describe the best mode contemplated by the inventors. It will be appreciated, however, that no matter how detailed the foregoing may appear in text, the invention may be practiced in many ways and the invention should be construed in accordance with the appended claims and any equivalents thereof.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of reducing sodium appetite in a subject in need thereof, the method comprising: inhibiting a plurality of prodynorphin (PDYN)-positive neurons in the pre-locus coeruleus (pre-$LC^{PDYN}$ neurons) of the subject, wherein inhibiting the plurality of pre-$LC^{PDYN}$ neurons of the subject comprises chemogenetically inhibiting the plurality of pre-$LC^{PDYN}$ neurons, thereby reducing sodium ingestion of the subject; and wherein sodium ingestion of the subject is reduced within 50 minutes or less relative to a subject wherein the pre-$LC^{PDYN}$ neurons have not been chemogenetically inhibited, following the chemogenetic inhibition of neurons in the pre-LC that express PDYN.

2. The method of claim 1, comprising determining sodium intake in the subject before inhibiting the plurality of pre-$LC^{PDYN}$ neurons of the subject.

3. The method of claim 1, comprising determining sodium intake in the subject after inhibiting the plurality of pre-$LC^{PDYN}$ neurons of the subject.

4. The method of claim 1, wherein the sodium ingestion of the subject is reduced by at least 50%.

5. The method of claim 1, wherein at least 50% of the plurality of pre-$LC^{PDYN}$ neurons express forkhead box protein P2 (FOXP2).

6. The method of claim 1, wherein the subject is a subject suffering from a kidney disorder, kidney damage, a cardiovascular disease, high blood pressure, overweight, edema, left ventricular hypertrophy, stroke, or a combination thereof; and optionally the kidney disorder is a chronic kidney disease or kidney failure.

\* \* \* \* \*